(12) United States Patent
Cremonesi et al.

(10) Patent No.: US 9,920,053 B2
(45) Date of Patent: Mar. 20, 2018

(54) N-(HETERO)ARYL-SUBSTITUTED HETEROYCLIC DERIVATIVES USEFUL FOR THE TREATMENT OF DISEASES OR CONDITIONS RELATED TO THE CENTRAL NERVOUS SYSTEM

(71) Applicant: CHRONOS THERAPEUTICS LIMITED, Oxford (GB)

(72) Inventors: Susanna Cremonesi, Verona (IT); Fabrizio Micheli, Verona (IT); Teresa Semeraro, Verona (IT); Luca Tarsi, Verona (IT); Tim Luker, Nottingham (GB); Colin Leslie, Verona (IT)

(73) Assignee: CHRONOS THERAPEUTICS LIMITED, Oxford (GB)

( * ) Notice: Subject to any disclaimer, the term of this patent is extended or adjusted under 35 U.S.C. 154(b) by 0 days.

(21) Appl. No.: 15/511,515

(22) PCT Filed: Sep. 14, 2015

(86) PCT No.: PCT/IB2015/057031
§ 371 (c)(1),
(2) Date: Mar. 15, 2017

(87) PCT Pub. No.: WO2016/042453
PCT Pub. Date: Mar. 24, 2016

(65) Prior Publication Data
US 2017/0253592 A1 Sep. 7, 2017

(30) Foreign Application Priority Data
Sep. 16, 2014 (GB) .................... 1416351.3

(51) Int. Cl.
| | | |
|---|---|---|
| C07D 211/48 | (2006.01) |
| C07D 401/04 | (2006.01) |
| C07D 401/14 | (2006.01) |
| C07D 403/04 | (2006.01) |
| C07D 403/14 | (2006.01) |
| C07D 471/04 | (2006.01) |
| C07D 487/04 | (2006.01) |

(52) U.S. Cl.
CPC .......... *C07D 471/04* (2013.01); *C07D 211/48* (2013.01); *C07D 401/04* (2013.01); *C07D 401/14* (2013.01); *C07D 403/04* (2013.01); *C07D 403/14* (2013.01); *C07D 487/04* (2013.01)

(58) Field of Classification Search
CPC .. C07D 211/48; C07D 401/04; C07D 401/14; C07D 403/04; C07D 403/14; C07D 471/04; C07D 482/04
See application file for complete search history.

(56) References Cited

U.S. PATENT DOCUMENTS 5,698,567 A 12/1997 Guillonneau et al.
6,835,371 B1 12/2004 Elmaleh et al.

FOREIGN PATENT DOCUMENTS

| EP | 1 683 797 A1 | 7/2006 |
| WO | WO-01/49677 A1 | 7/2001 |
| WO | WO-02/18437 A2 | 3/2002 |
| WO | WO-2004/005293 A2 | 1/2004 |
| WO | WO-2006/023630 A2 | 3/2006 |
| WO | WO-2007/050348 A2 | 5/2007 |
| WO | WO-2012/024397 A2 | 2/2012 |
| WO | WO-2015/031036 A1 | 3/2015 |
| WO | WO-2015/140132 A1 | 9/2015 |

OTHER PUBLICATIONS

Database Registry [Online] Chemical Abstracts Service, Columbus, Ohio, US; Jun. 17, 2005, "2,7-Diazaspiro[4.5]decan-1-one, 2-(4-phenoxyphenyl)-," XP002750359, Database accession No. 852432-89-4.
Database Registry [Online] Chemical Abstracts Service, Columbus, Ohio, US; Mar. 30, 2010, "1,7-Diazaspiro[4.4]nonane, 1-methyl-7-(5-phenoxy-3-pyridinyl)-," XP002750360, Database accession No. 1215074-56-8.
Database Registry [Online] Chemical Abstracts Service, Columbus, Ohio, US; Jun. 5, 2013, "2,7-Diazaspiro[4.5]decan-6-one, 2-[5-methyl-6-[(2-methyl-3-pyridinyl)-oxy]-" XP002750362, Database accession No. 1434891-71-0.
Database Registry [Online] Chemical Abstracts Service, Columbus, Ohio, US; Jan. 6, 2014, "2,7-Diazaspiro[4.4]nonane, 2-[I-(phenylmethyl)-IH-pyrazol-4-yl]-," XP002750363, Database accession No. 1512788-53-2.
Database Registry [Online] Chemical Abstracts Service, Columbus, Ohio, US; Mar. 7, 2012, "1-Oxa-3,8-diazaspiro[4.6]undecanone, 3-methyl-8-[5-methyl-6-[(2-methyl-3-pyridinyl)oxy]-4-pyrimidinyl]-", XP002750361, Database accession No. 1360173-11-0.

(Continued)

*Primary Examiner* — Timothy R Rozof
(74) *Attorney, Agent, or Firm* — Foley & Lardner LLP

(57) ABSTRACT

The present invention provides compounds of formula (I): compositions comprising such compounds; the use of such compounds in therapy (for example in the treatment or prevention of a disease, disorder or condition ameliorated by inhibition of a dopamine transporter); and methods of treating patients with such compounds; wherein $R^1$, $R^2$, $R^3$, $R^4$, $R^{9a}$, $R^{9b}$, $R^{9c}$, $R^{9d}$, $R^{9e}$, $R^{9f}$, m, n, A, L and B are as defined herein.

(I)

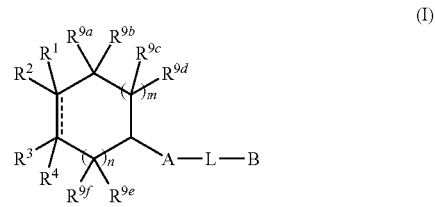

21 Claims, No Drawings

(56) References Cited

OTHER PUBLICATIONS

Fritch, Paul C. et al, "Design, syntheses, and SAR of 2,8-diazaspiro[4.5]decanones as T-type calcium channel antagonists," Bioorganic & Medicinal Chemistry Letters, vol. 20, No. 22, 2010, pp. 6375-6378.
International Search Report & Written Opinion in International Application No. PCT/IB2015/057029, dated Mar. 24, 2016. (11 pages).
International Search Report & Written Opinion in International Application No. PCT/IB2015/057030, dated Mar. 24, 2016. (13 pages).
International Search Report & Written Opinion in International Application No. PCT/IB2015/057031, dated Mar. 24, 2016. (8 pages).
Michela Bettati et al: "Oxa-azaspiro Derivatives: a Novel Class of Triple Re-uptake Inhibitors," Chemmedchem, vol. 5, No. 3, Mar. 1, 2010, pp. 361-366.
Motel, William C et al, "Chlorophenylpiperazine analogues as high affinity dopamine transporter ligands," Bioorganic & Medicinal Chemistry Letters, vol. 23, No. 24, 2013, pp. 6920-6922.
Abler B et al., "Neural Correlates of Antidepressant-Related Sexual Dysfunction: A Placebo-Controlled fMRI Study on Healthy Males Under Subchronic Paroxetine and Bupropion," Neuropsychopharmacology. 2011; 36(9): 1837-1847.
Amsterdam et al., "Greater Striatal Dopamine Transporter Density May Be Associated With Major Depressive Episode," J Affect Disord. 2012; 141(2-3): 425-431.
Auriel et al., "Effects of Methylphenidate on Cognitive Function and Gain in Patients Wth Parkinson's Disease," Clin Neuropharmacol. 2006; 29(1): 15-17.
Baldwin DS et al., "Antidepressant drugs and sexual dysfunction," Br J Psychiatry. 2013; 202: 396-397.
Baumann MH et al., "GBR12909 Attenuates Cocaine-Induced Activation of Mesolimbic Dopamine Neurons in the Rat," J Pharmacol Exp Ther. 1994; 271(3): 1216-1222.
Bello et al., "Acute methylphenidate treatments reduce sucrose intake in restricted-fed bingeing rats," Brain Res Bull. 2006; 70(4-6): 422-429.
Berrios GE, "Feelings of Fatigue and Psychopathology: A Conceptual History," Compr Psychiatry 1990; 31(2): 140-151.
Campbell VC et al., "Assessment of the Influence of Histaminergic Actions on Cocaine-Like Effects of 3α-Diphenylmethoxytropane Analogs," J Pharmacol Exp Ther. 2005; 315(2): 631-640.
Cheon et al., "Dopamine transporter density of the basal ganglia assessed with [123I]IPT SPECT in drug-naive children with Tourette's disorder," Psychiatry Res. 2004; 130(1): 85-95.
Cohen NJ et al., "The Effect of Methylphenidate on Attentive Behavior and Autonomic Activity in Hyperactive Children," Psychopharmacologia. 1971; 22(3): 282-294.
Cook EH Jr et al., "Association of Attention-Deficit Disorder and the Dopamine Transporter Gene," Am J Hum Genet. 1995; 56(4): 993-998.
Cornish RS et al., "Pharmacodynamic Assessment of the Benztropine Analogues AHN-1055 and AHN-2005 Using Intracerebral Microdialysis to Evaluate Brain Dopamine Levels and Pharmacokinetic/Pharmacodynamic Modeling," Pharm Res. 2005; 22(4): 603-612.
Denolle T et al., "Hemodynamic effects of reboxetine in healthy male volunteers," Clin Pharmacol Ther. 1999; 66(3): 282-287.
Devos D et al., "Improvement of gait by chronic, high doses of methylphenidate in patients with advanced Parkinson's disease," J Neurol Neurosurg Psychiatry. 2007; 78(5): 470-475.
Dworkin N, "Letters to the Editor: Increased Blood Pressure and Atomoxetine," J Am Acad Child Adolesc Psychiatry. 2005; 44(6): 510.
Espay et al., "Methylphenidate for gait impairment in Parkinson disease," Neurology. 2011; 76(14): 1256-1262.
Grigorenko EL et al., "Aggressive Behavior, Related Conduct Problems, and Variation in Genes Affecting Dopamine Turnover," Aggress Behav. 2010; 36(3): 158-176.
Harris JD, "Fatigue in chronically ill patients," Curr Opin Support Palliat Care 2008; 2(3): 180-186.
Hartmann E et al.,"Sleep: Effects of d- and l-Amphetamine in Man and in Rat," Psychopharmacology (Berl). 1976 10; 50(2): 171-175.
Hsiao et al., "The interaction between dopamine transporter function, gender differences,and possible laterality in depression," Psychiatry Res. 2013; 211(1): 72-77.
Kim CH et al., "Dopamine transporter density of basal ganglia assessed with [123I]IPT SPET in obsessive-compulsive disorder," Eur J Nucl Med Mol Imaging. 2003; 30(12): 1637-1643.
Lacerda et al., "Vanoxerine: Cellular Mechanism of a New Antiarrhythmic," J Cardiovasc Electrophysiol. 2010; 21(3): 301-310.
Lader MH, "Tolerability and Safety: Essentials in Antidepressant Pharmacotherapy," J Clin Psychiatry. 1996; 57 Suppl 2: 39-44.
Leibowitz SF et al., "Amphetamine: Effects on Meal Patterns and Macronutrient Selection," Brain Res Bull. 1986; 17(5): 681-689.
Li SM et al., "N-Substituted Benztropine Analogs: Selective Dopamine Transporter Ligands with a Fast Onset of Action and Minimal Cocaine-Like Behavioral Effects," J Pharmacol Exp Ther. 2011; 336(2): 575-585.
Michaelides M et al., "Dopamine-related frontostriatal abnormalities in obesity and binge-eating disorder: Emerging evidence for developmental psychopathology," Int Rev Psychiatry. 2012; 24(3): 211-218.
Montejo-González AL et al., "SSRI-Induced Sexual Dysfunction: Fluoxetine, Paroxetine, Sertraline, and Fluvoxamine in a Prospective, Multicenter, and Descriptive Clinical Study of 344 Patients," J Sex Marital Ther. 1997; 23(3): 176-194.
Nieoullon A, "Dopamine and the regulation of cognition and attention," Prog Neurobiol. 2002; 67(1): 53-83.
Olfson M et al., "Antidepressant Drug Therapy and Suicide in Severely Depressed Children and Adults," Arch Gen Psychiatry. Aug. 2006; 63(8): 865-872.
Remy P et al., "The role of dopamine in cognition," Curr Opin Neurol. 2003; 16 Suppl 2: S37-41.
Rothman RB et al., "GBR12909 Antagonizes the Ability of Cocaine to Elevate Extracellular Levels of Dopamine," Pharmacol Biochem Behav. 1991; 40(2): 387-397.
Segman et al., "Association between the dopamine transporter gene and posttraumatic stress disorder," Mol Psychiatry. 2002; 7(8): 903-7.
Shinohara M et al., "Eating disorders with binge-eating behaviour are associated with the s allele of the 3'-UTR VNTR polymorphism of the dopamine transporter gene," J Psychiatry Neurosci. 2004; 29(2): 134-137.
Slama et al., "Double Blind Clinical Trial of Mazindol on Weight Loss Blood Glucose, Plasma Insulin and Serum Lipids in Overweight Diabetic Patients," Diabete Metab. 1978; 4(3): 193-199.
Van Gaalen MM et al., "Critical Involvement of Dopaminergic Neurotransmission in Impulsive Decision Making," Biol Psychiatry. 2006; 60(1): 66-73.
Wang GJ et al., "Enhanced Striatal Dopamine Release During Food Stimulation in Binge Eating Disorder," Obesity (Silver Spring) 2011; 19(8): 1601-1608.
Wise RA, "Addictive Drugs and Brain Stimulation Reward," Annu Rev Neurosci. 1996; 19: 319-340.
Yoon et al., "Frontal dopaminergic abnormality in Tourette syndrome: A postmortem analysis," J Neurol Sci. 2007; 255(1-2): 50-56.
Zou MF et al., "Structure-Activity Relationship Studies on a Novel Series of (S)-2β-Substituted 3α-[Bis(4-fluoro- or 4-chlorophenyl)methoxy]tropane Analogues for in Vivo Investigation," J Med Chem. 2006; 49(21): 6391-6399.
Database Registry [Online] Chemical Abstracts Service, Columbus, Ohio, US; Jun. 13, 2011, "Pyrrolo[3,4-c]pyrazole-1(4H)-ethanol, 5,6-dihydro-5[5-methyl-6-[(2-methyl-3-pyridinyl)oxy]-4-pyrimidinyl]," Database accession No. 1309141-55-6.

N-(HETERO)ARYL-SUBSTITUTED HETEROYCLIC DERIVATIVES USEFUL FOR THE TREATMENT OF DISEASES OR CONDITIONS RELATED TO THE CENTRAL NERVOUS SYSTEM

CROSS-REFERENCE TO RELATED APPLICATIONS

This application is a U.S. National Stage Application under 35 U.S.C. § 371 of International Application No. PCT/IB2015/057031, filed on Sep. 14, 2015, which claims priority to GB Application No. 1416351.3, filed on Sep. 16, 2014, the contents of which are incorporated herein by reference in their entirety.

This invention relates to heterocyclic derivatives that are inhibitors of dopamine active transporter protein (DAT) and to pharmaceutical compositions containing, and the uses of, such derivatives.

BACKGROUND TO THE INVENTION

The spirocyclic derivatives of the present invention are inhibitors of human dopamine active transporter protein (DAT) and have a number of therapeutic applications, particularly in the treatment of sexual dysfunction, affective disorders, anxiety, depression, chronic fatigue, Tourette syndrome, Angelman syndrome, attention deficit disorder (ADD), attention deficit hyperactivity disorder (ADHD), obesity, pain, obsessive-compulsive disorder, movement disorders, CNS disorders, sleep disorders, narcolepsy, conduct disorder, substance abuse (including smoking cessation), eating disorders, and impulse control disorders.

Dopamine (DA) is a neurotransmitter which has a fundamental role in cognitive, affective, motor, motivational and reward-related functions. Following evoked action potentials DA is released into the synaptic cleft and this DA signal is extinguished by reuptake of DA into pre-synaptic neurons by DAT and by amine diffusion and local metabolism via enzymatic degradation. Dysfunction of the dopaminergic system is implicated in numerous CNS disorders and consequently DAT has been the focus of research into a number of these conditions and strong associations exist between abnormal DAT expression and/or function and disease.

Several marketed drugs have pharmacological activity at DAT, but none are selective and potent DAT inhibitors. Stimulants such as amphetamine and methylphenidate have multiple pharmacological activities including effects on synaptic levels of DA, noradrenaline (NE) and serotonin (5-HT). Despite their therapeutic potential in conditions such as ADHD, they also carry unwanted side effects such as abuse potential (1), cardiovascular effects (2), appetite suppression (3) and sleep disturbance (4).

Other non-selective DAT inhibitors are also used to treat CNS disorders. Bupropion which is prescribed as an antidepressant and a smoking cessation aid has a significant DAT component to its pharmacological activity, although it carries an increased seizure risk. Similarly Modafinil which is prescribed as a treatment for narcolepsy, excessive daytime sleepiness and shift work sleep disorder has been shown to inhibit DAT as part of its pharmacological mechanism of action. Multiple compounds have been developed that target the other monoamine transporters either selectively as inhibitors of the serotonin transporter (SERT) (Citalopram, Fluoxetine) or noradrenaline transporter (NET) inhibitors (Atomoxetine, Reboxetine) as well as dual serotonin/noradrenaline reuptake inhibitors (Venlafaxine). Drugs that inhibit SERT and NET have been burdened with multiple adverse side effects such as nausea (5), sexual dysfunction (6), increased suicide risk (7) for drugs that elevate 5-HT levels and elevated heart rate and blood pressure (8, 9) for drugs that increase noradrenaline levels. This makes a selective and potent DAT inhibitor, with a neurochemical profile distinct from that of stimulants, a highly desirable compound for the treatment of CNS disorders.

ADD and ADHD are neurodevelopmental psychiatric, behavioural and cognitive disorders characterised by concentration deficits, inner restlessness/hyperactivity, and impulsivity. These are the most common behavioural disorders amongst children, with a prevalence of 5-10% of the general population. It is widely believed that the symptoms of these disorders result from a dopaminergic and/or noradrenergic hypofunction. There is a wealth of information showing that the core symptoms of ADHD are influenced by changes in dopaminergic function (10) and hence a DAT inhibitor which would raise synaptic DA levels, should be efficacious. Current treatments for ADD/ADHD include the stimulants amphetamine and methylphenidate. These compounds have pharmacological activity for DAT, amongst other activities, and it is believed that their efficacy is derived from the elevation of corticostriatal DA and NE. These drugs are not selective DAT inhibitors however, and as such cause rapid, transient and marked release of DA from synaptic terminals which has been associated with their unwanted side effects, such as abuse potential. This neurochemical profile is distinct from that of a selective and potent DAT inhibitor which causes a slower increase in dopamine which is sustained for a much longer duration. This different neurochemical profile has been associated with less reinforcing effects and subsequently lower abuse potential (11). In addition to the neurochemical evidence for a likely therapeutic benefit of DAT inhibitors in ADHD, several studies have shown associations between DAT polymorphisms and overexpression of DAT in ADHD (12). Preclinical models of ADHD symptoms have shown that like amphetamine and methylphenidate a selective DAT inhibitor will decrease impulsive behaviour in rodents (13) further supporting the potential for efficacy of DAT inhibitors. Collectively this evidence provides compelling data to believe that selective DAT inhibitors will be efficacious in ADD/ADHD and other disorders characterised by poor impulse control (such as Trichotillomania, pathological gambling, Kleptomania and disorders with comorbid impulse control such as Parkinson's disease) or inattention.

Tourette's syndrome is a neuropsychiatric disorder characterised by motor and/or phonic tics. It normally presents during childhood and is poorly treated with drugs. Studies have postulated that one aspect underlying Tourette's is dopaminergic dysfunction whereby tonic/phasic dysfunction results in reduced synaptic DA levels and consequently higher levels in axon terminals leading to increased stimulus dependent release. Further studies have shown that postmortem tissue from Tourette's patients showed elevated levels of DAT in the frontal lobe (14) and that polymorphisms in DAT are associated with the occurrence of Tourette's. This was further supported in a clinical study of drug naïve children which showed and increased specific/non-specific DAT binding ratio in those with Tourette's (15). These findings suggest that a selective DAT inhibitor may provide symptomatic relief for Tourette's patients.

Other neuropsychiatric disorders such as obsessive compulsive disorder (OCD), oppositional defiant disorder (ODD) and conduct disorder have also been associated with DAT. OCD patients have been shown to have an increased specific/non-specific DAT binding ratio (16) and this ratio was altered following treatment with SSRIs which are commonly used to treat OCD. Similarly abnormal dopamine function and/or dopamine turnover have been implicated in ODD, conduct disorder and other related behavioural disorders (17) and polymorphisms in DAT have been implicated as a risk factor for externalising behaviour in children. Studies showing that children with conduct disorder display disrupted reinforcement signalling and a response to reward have also suggested that modulation of synaptic dopamine levels could be a therapeutic option for these disorders presenting the opportunity to use a selective DAT inhibitor to treat these behavioural disorders.

Sleep disorders such as narcolepsy, cataplexy, excessive daytime sleepiness and shift work sleep disorder can interfere with an individual's normal mental and physical well-being. Several of these disorders are treated with drugs that have pharmacological activity at DAT. Modafinil is widely used to treat narcolepsy and its therapeutic potential has been related to occupancy of DAT). Other treatments for sleep disorders include amphetamine, methamphetamine and methylphenidate, all of which have pharmacological actions at DAT. Preclinical studies have shown that the wake promoting effects of several of these compounds and a selective DAT inhibitor are abolished in DAT knockout mice. Together these data support the use of a selective DAT inhibitor in the treatment of sleep disorders.

Mood disorders such as major depressive disorder, bipolar depression, seasonal affective disorder, melancholic depression, catatonic depression, postpartum depression and dysthymia represent a major medical and social burden on society and are amongst the most common of all CNS disorders. Treatment for these disorders is currently inadequate with low levels of efficacy and poor responder rates to currently available therapies. In addition many of the drugs that are the current standard of care carry unwanted side effects. SPECT studies in patients suffering from major depressive disorder have shown that there is an increased binding of DAT in depressed patients and that this was reversed following successful antidepressant treatment (18, 19). In addition to this marketed antidepressants such as Nomifensine have a significant DAT inhibitory component to their mechanism of action. Preclinical studies investigating the behavioural phenotype of DAT knockout mice in tests for antidepressant activity have shown that genetic removal of DAT function results in antidepressant-like behaviour. This evidence is supportive for a therapeutic benefit for DAT inhibitors in mood disorders.

A comorbid symptom of depression and an unwanted side effect of many commonly used antidepressants is sexual dysfunction (20). Bupropion a commonly prescribed antidepressant with a significant DAT inhibitory component to its mechanism of action has been shown to result in fewer sexual dysfunction related side effects than other antidepressants (21). Furthermore Bupropion has been shown to reverse the sexual dysfunction caused by SSRIs. Preclinical studies have shown an effect of Bupropion on sexual behaviour in rats which is supported by clinical evidence that the drug is effective in treating women suffering from hypoactive sexual desire disorder. Amphetamine has also been shown to increase sexual behaviour in male and female rats and has also been shown to reverse sexual impairment in female rats. This evidence for drugs that have pharmacological activity at DAT is an indicator that a selective and potent DAT inhibitor would be a suitable therapy for antidepressant induced sexual dysfunction as well as for treating sexual dysfunction in non-depressed patients.

DAT polymorphisms have been implicated in anxiety disorders such as post traumatic stress disorder (PTSD) (22). The non-selective monoamine oxidase inhibitor Phenelzine which elevates dopamine levels in the brain amongst its actions has been shown to reduce the symptoms of PTSD. Bupropion which has a significant DAT inhibitory component to its mechanism of action is also prescribed for patients with anxiety disorders and has been shown to be efficacious in patients with panic disorder, further supporting the potential of DAT inhibitors in these conditions.

Movement disorders such as Parkinson's disease (PD) and Restless Leg Syndrome (RLS) are common neurological disorders which have been treated with therapies that result in elevated brain dopamine. PD is characterised by a loss of dopaminergic neurones in the nigrostriatal pathway and a subsequent loss of dopamine. Drugs such as L-DOPA which is converted to dopamine in the brain have been shown to alleviate the motor symptoms of both PD and RLS. Given that DAT inhibitors also increase dopamine levels it is reasonable to assume that they would also provide therapeutic benefit in movement disorders which have been shown to have a dopaminergic component. Further support for this hypothesis is given by the fact that methylphenidate, a stimulant which has DAT inhibition amongst its pharmacological activities has shown to be clinically efficacious in PD patients, both in motor (23) and non-motor symptoms (24,25).

Addiction and substance abuse are closely linked to dopamine and reward circuits in the brain. These substance dependencies include alcohol dependence, opioid dependence, cocaine dependence, *cannabis* dependence, amphetamine dependence (or amphetamine-like), hallucinogen dependence, inhalant dependence, polysubstance dependence, phencyclidine (or phencyclidine-like) dependence, and nicotine dependence. Preclinical studies using the selective DAT inhibitor GBR12909 and other benztropines have shown that these compounds can block the rewarding effects of drugs of abuse, such as cocaine. GBR12909 has been shown to block the neurochemical effects of cocaine (26, 27) as well as that of amphetamine. Furthermore compounds which have been demonstrated to be DAT inhibitors are effective in smoking cessation. This provides evidence that a high affinity, selective DAT inhibitor could block the rewarding effects of drugs of abuse and be an effective medication to treat addiction.

Dopamine is also known to have a role in eating disorders such as Binge Eating Disorder (BED). Eating disorders such as BED are known to have multiple components including impulse control, reward circuits and cognition, all of which are under the influence of dopaminergic signalling. It has been shown that BED sufferers have abnormal brain dopamine responses, which regulates motivation for food intake (28). In addition BED and obese patients show an abnormal frontostriatal dopamine signalling as compared to healthy controls (29). Preclinical models have shown that stimulation of the nucleus accumbens, which receives major dopaminergic input, attenuates binge eating behaviour in rats and that this effect is blocked by dopaminergic antagonists. This indicates that increased synaptic dopamine is a potential therapeutic opportunity for eating disorders such as binge eating disorder. Preclinical data has shown that food intake is modulated by drugs which modulate synaptic dopamine levels and specifically by compounds with affinity at DAT (30). DAT has been specifically implicated in BED and other eating disorders due to polymorphisms in DAT being associated with eating disorders (31). This hypothesis is further supported by the efficacy of drugs with DAT inhibition as part of their mechanism of action in clinical trials of BED and other eating disorders (32). Together this is supportive for the therapeutic potential of a selective DAT inhibitor in eating disorders such as BED.

Dopamine has a well-documented role in cognition and particularly in cognitive deficits seen in patients suffering from diseases characterised by abnormal dopaminergic signalling such as Parkinson's disease and schizophrenia (33). This coupled with the fact that cortical dopamine D1 receptor function is linked to NMDA mediated glutamate signalling implies that cognitive processes would be expected to be enhanced by DAT inhibitors.

Chronic or persistent fatigue is a symptom which is common to several diseases and can be persisting or relapsing (34). Disease states that are associated with fatigue include chronic fatigue syndrome, post-viral fatigue syndrome, HIV, multiple sclerosis, amyotrophic lateral sclerosis (ALS), myasthenia gravis, sarcoidosis, cancer, chemotherapy treatment, celiac disease, irritable bowel syndrome, spondyloarthropathy, fibromyalgia, arthritis, infectious diseases, diabetes, eating disorders, Parkinson's disease, sleep disorders, stroke, mood disorders, drug and alcohol abuse. Clinical studies have shown that multiple drugs with DAT inhibition as part of their mechanism of action are effective in combating fatigue in chronically ill patients (35). Drugs such as modafinil, methylphenidate and bupropion which share DAT inhibition as a common pharmacological mechanism of action have been shown to be efficacious in fatigue associated with cancer, chemotherapy, sarcoidosis, ALS, depression, bipolar disorder, multiple sclerosis, Parkinson's disease, HIV and chronic fatigue syndrome. This evidence is supportive of likely efficacy for a selective and potent DAT inhibitor in fatigue associated with the diseases mentioned above.

The multiple potential applications for a selective and potent DAT inhibitor have resulted in numerous chemical series being described in the literature. A particular issue has been pharmacological selectivity, with many previously described structural classes of DAT inhibitors suffering from significant off target pharmacology, which has limited their development. A particular issue is the affinity of DAT inhibitors described in the literature for ion channels. Vanoxerine has been shown to have significant activity at multiple ion channels resulting in a cardiovascular safety risk that has hampered its development (36).

The compound showed potent functional activity at multiple sodium, calcium and potassium channels which would be an undesirable profile for a drug to treat CNS disorders. In addition to off target ion channel pharmacology DAT inhibitors (particularly those of the benztropine class) have been shown to have pharmacological activity at multiple other receptors such as the serotonin receptor 5-HT2, the muscarinic receptor M1 and the histamine receptor H1 (37,38,39). These significant secondary pharmacological activities may introduce unwanted side effects to potentially therapeutically beneficial DAT inhibitors. This makes the selectivity profile of DAT inhibitors of particular importance.

Therefore there remains a need to develop new DAT inhibitors, especially inhibitors that are selective over noradrenaline and serotonin, that will have utility to treat a wide range of disorders, in particular to treat depression, ADHD and eating disorders. Preferred compounds will possess a good pharmacokinetic profile and in particular will be suitable as drugs for oral delivery. Particularly preferred compounds will additionally display selectivity over noradrenaline and serotonin.

SUMMARY OF THE INVENTION

The present invention relates to a series of heterocyclic derivatives that are inhibitors of DAT. Many of these compounds demonstrate good selectivity for DAT and are potentially useful in the treatment of sexual dysfunction, affective disorders, anxiety, depression, Tourette syndrome, Angelman syndrome, attention deficit disorder (ADD), attention deficit hyperactivity disorder (ADHD), obesity, pain, obsessive-compulsive disorder, movement disorders, CNS disorders, sleep disorders, narcolepsy, conduct disorder, substance abuse (including cocaine abuse and smoking cessation), eating disorders, chronic fatigue and impulse control disorders. The invention further relates to pharmaceutical compositions of the inhibitors, to the use of the compositions as therapeutic agents, and to methods of treatment using these compositions.

In an aspect, the invention provides a compound according to formula I,

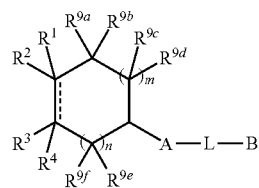

wherein:
A is selected from phenyl and heteroaryl;
B is selected from phenyl and heteroaryl;
L is a linker selected from alkylene and O;
$R^1$ is selected from H, alkyl, alkoxy, S-alkyl, $S(O)_q$alkyl, COR, $CONR^5R^6$, $COOR^5$, $CH_2OH$, OH, F and Cl;
$R^2$ is selected from $NR^7R^8$, $CR^{11}R^{12}NR^7R^8$, $CONR^7R^8$, $(CR^{11}R^{12})_2NR^7R^8$ and $(CR^{11}R^{12})_3NR^7R^8$, wherein $R^1$ is alkyl, alkoxy, $CH_2OH$, $COR^5$, $CONR^5R^6$ or $COOR^5$ when $R^2$ is $NR^7R^8$;
$R^3$ is selected from H, alkyl, alkoxy, $NR^7R^8$, $CH_2OH$, OH, F and Cl;
or $R^2$ and $R^3$ come together with the carbon atoms to which they are attached to form heterocyclyl or heteroaryl, wherein the heterocyclyl or heteroaryl contains at least one ring member selected from N and $NR^{13}$; provided that when $R^2$ and $R^3$ come together with the carbon atoms to which they are attached to form heterocyclyl or heteroaryl, L is O;
provided that when $R^1$ is H, either
  $R^2$ and $R^3$ come together with the carbon atoms to which they are attached to form heterocyclyl; or
  $R^3$ is selected from alkyl, alkoxy, $NR^7R^8$, $CH_2OH$, OH, F and Cl;
$R^4$, $R^5$ and $R^6$ are each independently selected from H and alkyl;
$R^7$ and $R^8$ are independently selected from H, alkyl, cycloalkyl, heterocyclyl, and $C(O)R^{10}$, wherein when $R^7$ is $C(O)R^{10}$, $R^8$ is H or alkyl; or $R^7$ and $R^8$ may come together with the nitrogen atom to which they are attached to form heterocyclyl;
$R^{9a}$, $R^{9b}$, $R^{9c}$, $R^{9d}$, $R^{9e}$ and $R^{9f}$ are independently selected from H and alkyl;

$R^{10}$ is selected from alkyl, aryl, heterocyclyl and heteroaryl;
---- is absent or represents a bond, wherein when ---- is a bond $R^1$ and $R^4$ are absent;
m is 0, 1 or 2, wherein when m is 2, n is 0;
n is 0, 1 or 2, wherein when n is 2, m is 0;
q is 1 or 2;
alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1, 2, 3, 4 or 5 substituents selected from S-alkyl, S(O)alkyl, S(O)$_2$alkyl, cycloalkyl, heterocyclyl, alkoxy, OH, —CN, CF$_3$, COOR$^{13}$, CONR$^{13}$R$^{14}$, F, Cl, NR$^{13}$COR$^{14}$ and NR$^{13}$R$^{14}$;
cycloalkyl is a monocyclic saturated hydrocarbon of between 3 and 7 carbon atoms ($C_3$-$C_7$); cycloalkyl may optionally be substituted with 1, 2, 3, 4 or 5 substituents independently selected from S-alkyl, S(O)alkyl, S(O)$_2$alkyl, alkyl, alkoxy, OH, —CN, CF$_3$, COOR$^{13}$, CONR$^{13}$R$^{14}$, F, Cl, and NR$^{13}$R$^{14}$;
phenyl may be optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, OCF$_3$, CF$_3$, NR$^{13}$COR$^{14}$ and NR$^{13}$R$^{14}$;
alkylene is a bivalent $C_{1-3}$ straight-chained alkyl radical or a bivalent $C_{3-4}$ branched alkyl radical, wherein alkylene may optionally be substituted with 1 or 2 substituents selected from S-alkyl, S(O)alkyl, S(O)$_2$alkyl, heterocyclyl, alkoxy, OH, —CN, CF$_3$, COOR$^{13}$, CONR$^{13}$R$^{14}$, F, Cl, NR$^{13}$COR$^{14}$ and NR$^{13}$R$^{14}$;
heterocyclyl is a monocyclic ring which is saturated or partially unsaturated, containing, where possible, 1 or 2 ring members independently selected from N, S, O and NR$^{13}$ and 2 to 5 carbon atoms; heterocyclyl may optionally be substituted with 1, 2 or 3 substituents independently selected from alkyl, cycloalkyl, alkoxy, S-alkyl, S(O)alkyl, S(O)$_2$alkyl, oxo, OH, F, Cl, —CN, OCF$_3$, CF$_3$, NR$^{13}$COR$^4$ and NR$^{13}$R$^{14}$;
heteroaryl is a 5 or 6 membered aromatic ring, containing, where possible, 1, 2 or 3 ring members independently selected from N, NR$^{13}$, S and O; heteroaryl may be optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, OCF$_3$, CF$_3$, NR$^{13}$COR$^{14}$ and NR$^{13}$R$^{14}$;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1, 2, 3, 4 or 5 substituents independently selected from S-alkyl, S(O)alkyl, S(O)$_2$alkyl, alkyl, OH, —CN, CF$_3$, COOR$^{13}$, CONR$^{13}$R$^{14}$, F, Cl, NR$^{13}$COR$^{14}$ and NR$^{13}$R$^{14}$;
$R^{11}$, $R^{12}$, $R^{13}$ and $R^{14}$ are independently selected from H and alkyl;
and tautomers, stereoisomers (including enantiomers, diastereoisomers and racemic and scalemic mixtures thereof), pharmaceutically acceptable salts and solvates thereof;
wherein the compound of formula I is not:

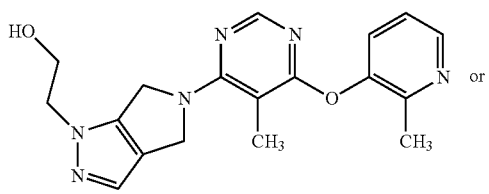

or

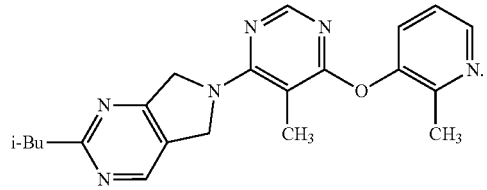

In an aspect, the invention comprises a compound of formula I, wherein when $R^2$ and $R^3$ come together with the carbon atoms to which they are attached to form heterocyclyl or heteroaryl, the sum of m and n is 2.

In an aspect, the invention comprises a compound of formula I, wherein:
$R^1$ is selected from alkyl, alkoxy, S-alkyl, S(O)$_q$alkyl, COR, CONR$^5$R$^6$, COOR$^5$, CH$_2$OH, OH, F and Cl;
$R^2$ is selected from NR$^7$R$^8$, CONR$^7$R$^8$, CR$^{11}$R$^{12}$NR$^7$R$^8$, (CR$^{11}$R$^{12}$)$_2$NR$^7$R$^8$ and (CR$^{11}$R$^{12}$)$_3$NR$^7$R$^8$;
$R^3$ is selected from H and alkyl;
$R^4$, $R^5$ and $R^6$ are each independently selected from H and alkyl;
---- is absent.

In an aspect, the invention comprises a compound of formula I, wherein n is 1 and m is 0 or 1.

In an aspect, the invention comprises a compound of formula I, wherein $R^{9a}$, $R^{9b}$, $R^{9c}$, $R^{9d}$, $R^{9e}$, $R^{9f}$, $R^{11}$ and $R^{12}$ are all H.

In an aspect, the invention comprises a compound of formula I, according to formula IA,

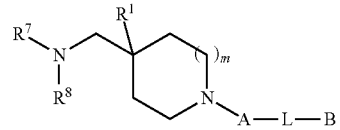

IA wherein:
A is selected from phenyl and heteroaryl;
B is selected from phenyl and heteroaryl;
L is a linker selected from alkylene and O;
$R^1$ is selected from CH$_2$OH, OH, F and Cl;
$R^7$ and $R^8$ are independently selected from H, alkyl, cycloalkyl, heterocyclyl, and C(O)R$^{10}$, wherein when $R^7$ is C(O)R$^{10}$, $R^8$ is H or alkyl; or $R^7$ and $R^8$ may come together with the nitrogen atom to which they are attached to form heterocyclyl;
$R^{10}$ is selected from alkyl, aryl, heterocyclyl and heteroaryl;
m is 0 or 1;
alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1, 2, 3, 4 or 5 substituents selected from cycloalkyl, heterocyclyl, S-alkyl S(O)alkyl, S(O)$_2$alkyl, alkoxy, OH, —CN, CF$_3$, COOR$^{13}$, CONR$^{13}$R$^{14}$, F, Cl, NR$^{13}$COR$^{14}$ and NR$^{13}$R$^{14}$;
cycloalkyl is a monocyclic saturated hydrocarbon of between 3 and 7 carbon atoms ($C_3$-$C_7$); cycloalkyl may optionally be substituted with 1, 2, 3, 4 or 5 substituents independently selected from S-alkyl, S(O)alkyl, S(O)$_2$alkyl, alkyl, alkoxy, OH, —CN, CF$_3$, COOR$^{13}$, CONR$^{13}$R$^{14}$, F, Cl, NR$^{13}$COR$^{14}$ and NR$^{13}$R$^{14}$;
phenyl may be optionally substituted with 1, 2 or 3 substituents independently selected from alkyl, cycloalkyl, heterocyclyl, alkoxy, S-alkyl, S(O)alkyl, S(O)₂alkyl, OH, F, Cl, —CN, OCF₃, CF₃, NR$^{13}$COR$^{14}$ and NR$^{13}$R$^{14}$;

heterocyclyl is a monocyclic ring which is saturated or partially unsaturated, containing, where possible, 1 or 2 ring members independently selected from N, S, O and NH and 2 to 5 carbon atoms; heterocyclyl may optionally be substituted with 1, 2 or 3 substituents independently selected from alkyl, cycloalkyl, alkoxy, S-alkyl, S(O)alkyl, S(O)₂alkyl, oxo, OH, F, Cl, —CN, OCF₃, CF₃, NR$^{13}$COR$^{14}$ and NR$^{13}$R$^{14}$;

heteroaryl is a 5 or 6 membered aromatic ring, containing, where possible, 1, 2 or 3 ring members independently selected from N, NR$^{13}$, S and O; heteroaryl may be optionally substituted with 1, 2 or 3 substituents independently selected from alkyl, cycloalkyl, alkoxy, S-alkyl, S(O)alkyl, S(O)₂alkyl, OH, F, Cl, —CN, OCF₃, CF₃, NR$^{13}$COR$^{14}$ and NR$^{13}$R$^{14}$;

alkoxy is a linear O-linked hydrocarbon of between 1 and 6 carbon atoms (C₁-C₆) or a branched O-linked hydrocarbon of between 3 and 6 carbon atoms (C₃-C₆); alkoxy may optionally be substituted with 1, 2, 3, 4 or 5 substituents independently selected from S-alkyl, S(O)alkyl, S(O)₂alkyl, alkyl, OH, —CN, CF₃, COOR$^{13}$, CONR$^{13}$R$^{14}$, F, Cl, NR$^{13}$COR$^{14}$ and NR$^{13}$R$^{14}$;

R$^{13}$ and R$^{14}$ are independently selected from H and alkyl;

and tautomers, stereoisomers (including enantiomers, diastereoisomers and racemic and scalemic mixtures thereof), pharmaceutically acceptable salts and solvates thereof.

In an aspect, the invention comprises a compound of formula I, wherein m is 1.

In an aspect, the invention comprises a compound of formula I, wherein R$^1$ is OH.

In an aspect, the invention comprises a compound of formula I, wherein L is O.

In an aspect, the invention comprises a compound of formula I, wherein A is phenyl, pyridyl or pyrimidinyl, optionally substituted with 1, 2 or 3 substituents independently selected from alkyl, cycloalkyl, heterocyclyl, alkoxy, S-alkyl, S(O)alkyl, S(O)₂alkyl, OH, F, Cl, —CN, OCF₃, CF₃, NR$^{13}$COR$^4$ and NR$^{13}$R$^{14}$.

In an aspect, the invention comprises a compound of formula I, wherein A is phenyl, 2-pyridyl or 1,3-pyrimidinyl, optionally substituted with 1, 2 or 3 substituents independently selected from alkyl, F, Cl, —CN and CF₃.

In an aspect, the invention comprises a compound of formula I, wherein A is selected from the group consisting of:

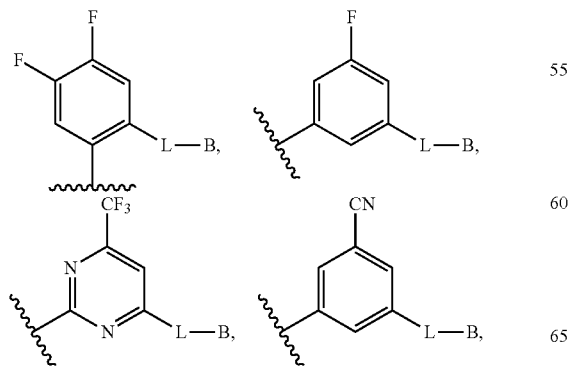

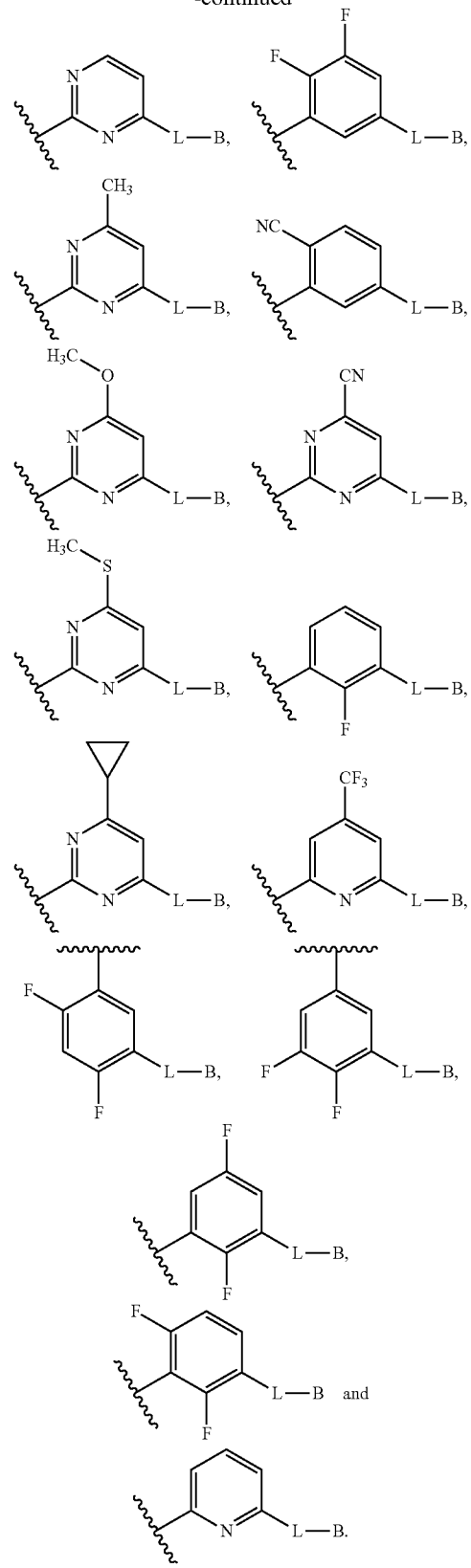

In an aspect, the invention comprises a compound of formula I, wherein B is phenyl, optionally substituted with 1, 2 or 3 substituents independently selected from alkyl, cycloalkyl, heterocyclyl, alkoxy, S-alkyl, S(O)alkyl, S(O)₂alkyl, OH, F, Cl, —CN, OCF₃, CF₃, NR¹³COR¹⁴ and NR¹³R¹⁴.

In an aspect, the invention comprises a compound of formula I, wherein B is selected from the group consisting of:

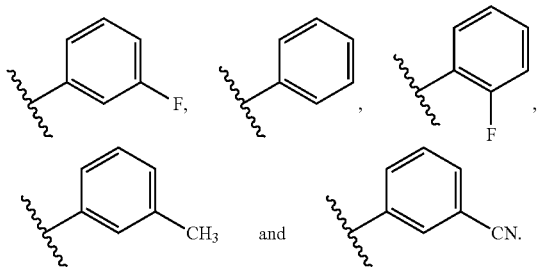

In an aspect, the invention comprises a compound selected from Examples 1 to 39.

In yet another aspect the present invention provides an N-oxide of a compound of formula I as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

DETAILED DESCRIPTION

In an aspect, the invention comprises a subset of the compounds of formula I, as defined by formula IB,

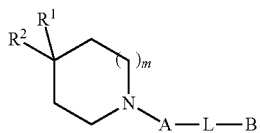

IB wherein:
A is selected from phenyl and heteroaryl;
B is selected from phenyl and heteroaryl;
L is a linker selected from alkylene and O;
either R¹ is CH₂OH and R² is NR⁷R⁸; or
R¹ is selected from OH, F and Cl, and R² is CH₂NR⁷R⁸;
R⁷ and R⁸ are independently selected from H, alkyl, cycloalkyl, heterocyclyl and C(O)R¹⁰, wherein when R⁷ is C(O)R¹⁰, R⁸ is H; or R⁷ and R⁸ may come together with the nitrogen atom to which they are attached to form heterocyclyl;
R¹⁰ is selected from alkyl, aryl, heterocyclyl and heteroaryl;
m is 0 or 1;
alkyl is a linear saturated hydrocarbon having up to 6 carbon atoms (C₁-C₆) or a branched saturated hydrocarbon of between 3 and 6 carbon atoms (C₃-C₆); alkyl may optionally be substituted with 1, 2, 3, 4 or 5 substituents selected from cycloalkyl, heterocyclyl, S-alkyl, S(O)alkyl, S(O)₂alkyl, alkoxy, OH, —CN, CF₃, COOR¹³, CONR¹³R¹⁴, F, Cl, NR¹³COR¹⁴ and NR¹³R¹⁴;
cycloalkyl is a monocyclic saturated hydrocarbon of between 3 and 7 carbon atoms (C₃-C₇); cycloalkyl may optionally be substituted with 1, 2, 3, 4 or 5 substituents independently selected from S-alkyl, S(O)alkyl, S(O)₂alkyl, alkyl, alkoxy, OH, —CN, CF₃, COOR¹³, CONR¹³R¹⁴, F, Cl, NR¹³COR¹⁴ and NR¹³R¹⁴;
phenyl may be optionally substituted with 1, 2 or 3 substituents independently selected from alkyl, cycloalkyl, heterocyclyl, alkoxy, S-alkyl, S(O)alkyl, S(O)₂alkyl, OH, F, Cl, —CN, OCF₃, CF₃, NR¹³COR¹⁴ and NR¹³R¹⁴;
heterocyclyl is a monocyclic ring which is saturated or partially unsaturated, containing, where possible, 1 or 2 ring members independently selected from N, S, O and NH and 2 to 5 carbon atoms; heterocyclyl may optionally be substituted with 1, 2 or 3 substituents independently selected from alkyl, cycloalkyl, alkoxy, S-alkyl, S(O)alkyl, S(O)₂alkyl, oxo, OH, F, Cl, —CN, OCF₃, CF₃, NR¹³COR⁴ and NR¹³R¹⁴;
heteroaryl is a 5 or 6 membered aromatic ring, containing, where possible, 1, 2 or 3 ring members independently selected from N, NR¹³, S and O; heteroaryl may be optionally substituted with 1, 2 or 3 substituents independently selected from alkyl, cycloalkyl, alkoxy, S-alkyl, S(O)alkyl, S(O)₂alkyl, OH, F, Cl, —CN, OCF₃, CF₃, NR¹³COR¹⁴ and NR¹³R¹⁴;
alkoxy is a linear O-linked hydrocarbon of between 1 and 6 carbon atoms (C₁-C₆) or a branched O-linked hydrocarbon of between 3 and 6 carbon atoms (C₃-C₆); alkoxy may optionally be substituted with 1, 2, 3, 4 or 5 substituents independently selected from S-alkyl, S(O)alkyl, S(O)₂alkyl, alkyl, OH, —CN, CF₃, COOR¹³, CONR¹³R¹⁴, F, Cl, NR¹³COR¹⁴ and NR¹³R¹⁴;
R¹³ and R¹⁴ are independently selected from H and alkyl;
and tautomers, stereoisomers (including enantiomers, diastereoisomers and racemic and scalemic mixtures thereof), pharmaceutically acceptable salts and solvates thereof.

The present invention also comprises the following aspects and combinations thereof.

In an aspect A is selected from phenyl, pyrazinyl, pyridyl and pyrimidinyl, optionally substituted with 1, 2 or 3 substituents independently selected from alkyl, cycloalkyl, alkoxy, S-alkyl, OH, F, Cl, —CN, OCF₃, CF₃ and NR¹³R¹⁴.

In an aspect A is selected from phenyl, pyridyl and pyrimidinyl, optionally substituted with 1, 2 or 3 substituents independently selected from alkyl, cycloalkyl, alkoxy, S-alkyl, F, —CN and CF₃.

In an aspect A is selected from phenyl, 2-pyridyl and 1,3-pyrimidinyl, optionally substituted with 1, 2 or 3 substituents independently selected from alkyl, cycloalkyl, alkoxy, S-alkyl, F, —CN and CF₃.

In an aspect A is phenyl or pyrimidinyl, optionally substituted with 1, 2 or 3 substituents independently selected from alkyl, cycloalkyl, alkoxy, S-alkyl, F, —CN and CF₃.

In an aspect B is phenyl or pyridyl, optionally substituted with 1, 2 or 3 substituents independently selected from alkyl, cycloalkyl, alkoxy, S-alkyl, OH, F, Cl, —CN, OCF₃, CF₃ and NR¹³R¹⁴.

In an aspect B is phenyl, optionally substituted with 1, 2 or 3 substituents independently selected from alkyl, alkoxy, OH, F, Cl, —CN, OCF₃, and CF₃.

In an aspect B is selected from unsubstituted phenyl or phenyl substituted with 1 or 2 groups selected from F, —CN and CH₃.

In an aspect B is phenyl substituted with one F substituent. In an aspect B is meta-fluoro-phenyl.

In an aspect:
R¹ is selected from H, alkyl, alkoxy, CH₂OH, OH, F and Cl;

$R^2$ is selected from $NR^7R^8$, $CR^{11}R^{12}NR^7R^8$, $(CR^{11}R^{12})_2NR^7R^8$ and $(CR^{11}R^{12})_3NR^7R^8$, and $R^3$ is selected from H and alkyl; or $R^2$ and $R^3$ come together with the carbon atoms to which they are attached to form heterocyclyl or heteroaryl, wherein the heterocyclyl or heteroaryl contains at least one ring member selected from N and $NR^{13}$;

provided that when $R^2$ and $R^3$ come together with the carbon atoms to which they are attached to form heterocyclyl or heteroaryl, L is O and provided that when $R^1$ is H, $R^2$ and $R^3$ come together with the atoms to which they are attached to form heterocyclyl.

In an aspect:
$R^1$ is selected from alkyl, alkoxy, $CH_2OH$, OH, F and Cl;
$R^2$ is selected from $NR^7R^8$, $CR^{11}R^{12}NR^7R^8$, $(CR^{11}R^{12})_2NR^7R^8$ and $(CR^{11}R^{12})_3NR^7R^8$;
$R^3$ is selected from H and alkyl;
$R^4$, $R^5$ and $R^6$ are each independently selected from H and alkyl;
——— is absent.

In an aspect $R^1$ is selected from H, alkyl, alkoxy, $CH_2OH$, OH, F and Cl.

In an aspect $R^1$ is selected from $CH_2OH$, OH, F and Cl.
In an aspect $R^1$ is selected from OH, F and Cl.
In an aspect $R^1$ is OH or F.
In an aspect $R^1$ is OH.
In an aspect $R^2$ is selected from $NR^7R^8$, $CR^{11}R^{12})_2NR^7R^8$, $(CR^{11}R^{12})_2NR^7R^8$ and $(CR^{11}R^{12})_3NR^7R^8$ wherein $R^1$ is alkyl or $CH_2OH$ when $R^2$ is $NR^7R^8$.
In an aspect $R^2$ is $NR^7R^8$ or $CH_2NR^7R^8$.
In an aspect $R^2$ is $CH_2NR^7R^8$. In an aspect $R^2$ is $CH_2NH_2$.
In an aspect L is methylene, ethylene or O.
In an aspect L is methylene or O.
In an aspect L is O.
In an aspect $R^{9a-f}$ are all H. In an aspect $R^{13}$ is H. In an aspect $R^{14}$ is H.
In an aspect m is 0 or 1 and n is 0 or 1.
In an aspect n is 1 and m is 0 or 1. In an aspect n is 1 and m is 1.
In an aspect $R^3$ and $R^4$ are independently selected from H and alkyl.
In an aspect $R^3$ and $R^4$ are H.
In an aspect $R^7$ and $R^8$ are independently selected from H, alkyl, cycloalkyl, heterocyclyl, and $C(O)R^{10}$, wherein when $R^7$ is $C(O)R^{10}$, $R^8$ is H; or $R^7$ and $R^8$ may come together with the nitrogen atom to which they are attached to form heterocyclyl.
In an aspect q is 2.
In an aspect $NR^7R^8$ is selected from:

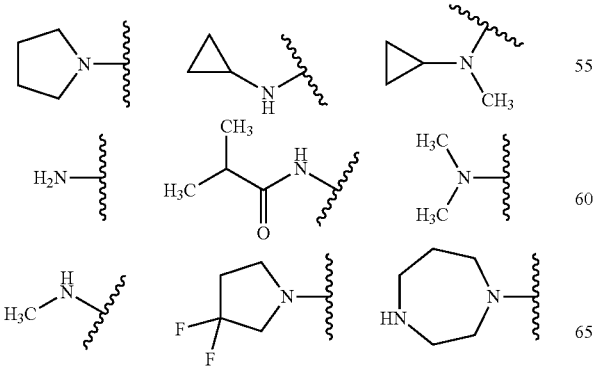

-continued

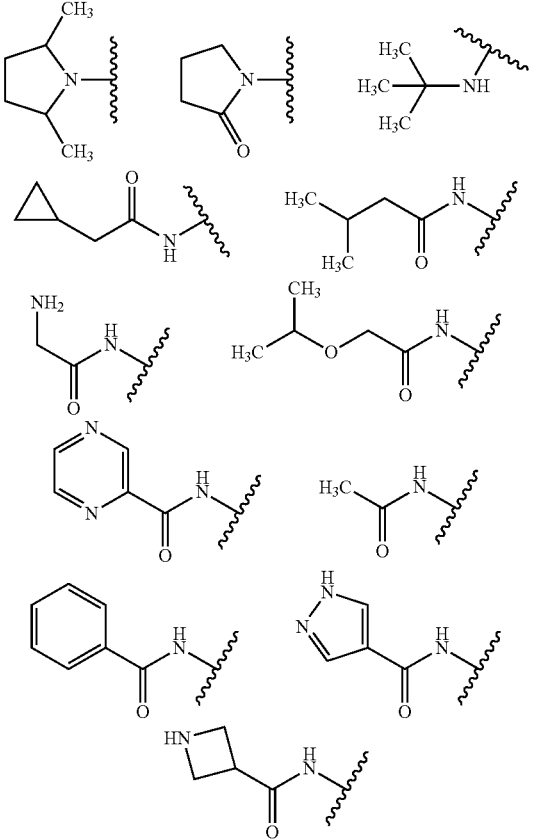

In an aspect, the invention comprises a subset of the compounds of formula I selected from:

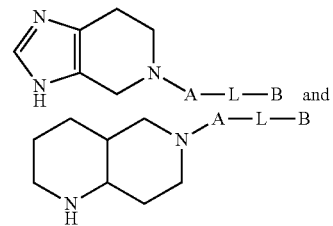

In an aspect A-L-B is selected from:

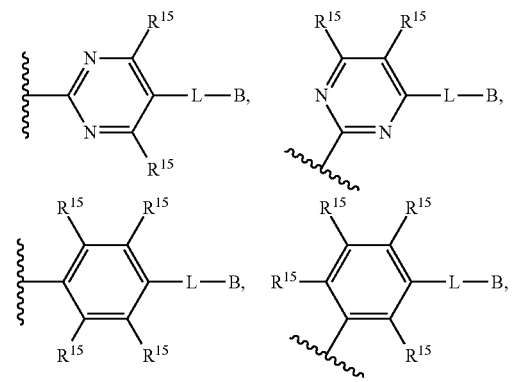

-continued

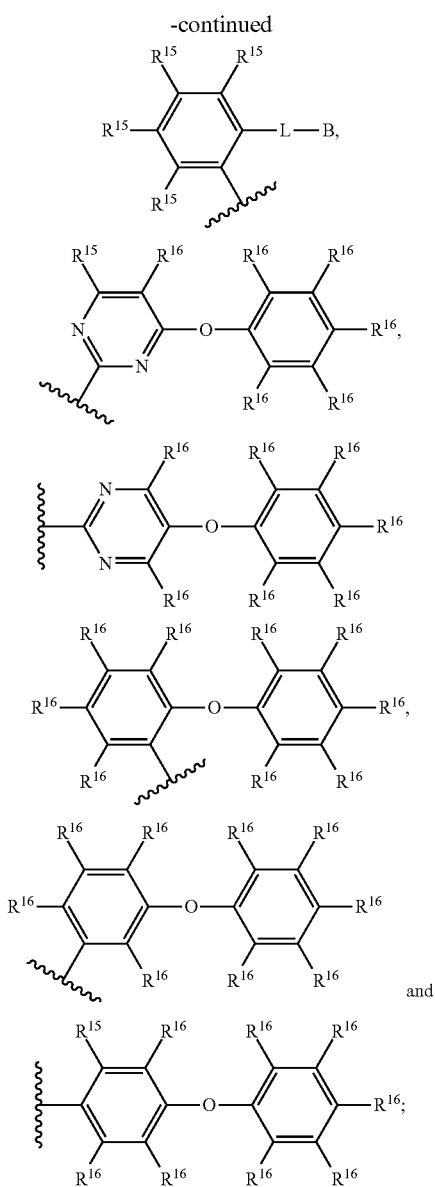

and wherein,
each $R^{15}$ is independently selected from H and $R^{17}$, and 0, 1, 2 or 3 $R^{15}$ are $R^{17}$;
each $R^{16}$ is independently selected from H and $R^{17}$, and 0, 1, 2 or 3 $R^{16}$ are $R^{17}$; and
each $R^{17}$ is independently selected from alkyl, cycloalkyl, heterocyclyl, alkoxy, S-alkyl, S(O)alkyl, S(O)$_2$alkyl, OH, F, Cl, —CN, OCF$_3$, CF$_3$, NR$^{13}$COR$^{14}$ and NR$^{13}$R$^{14}$.

In an aspect A is selected from:

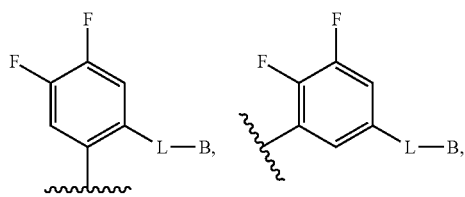

-continued

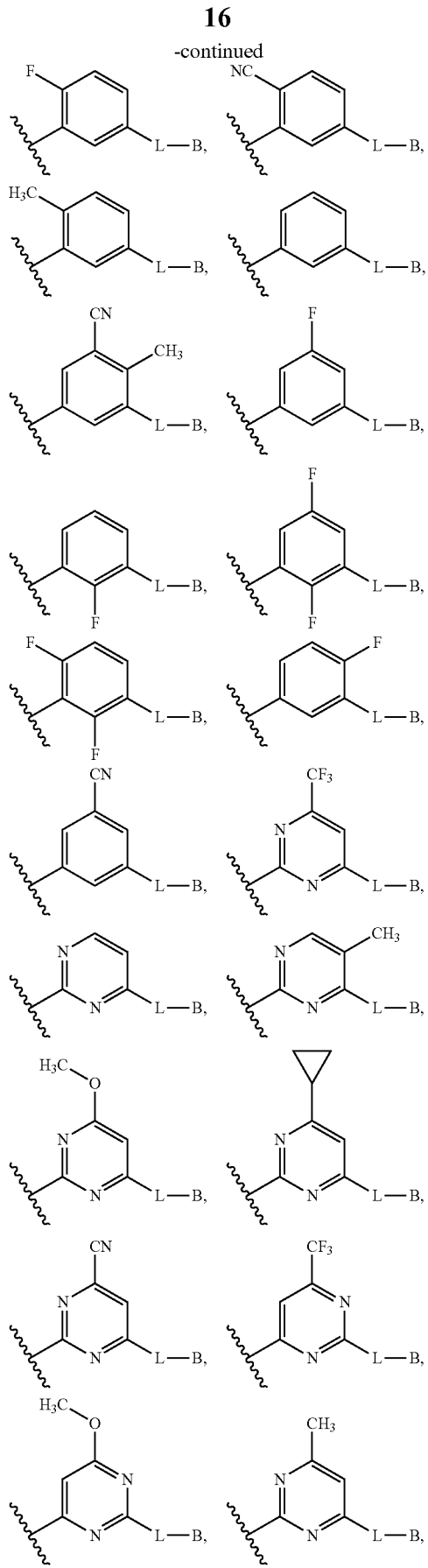

-continued
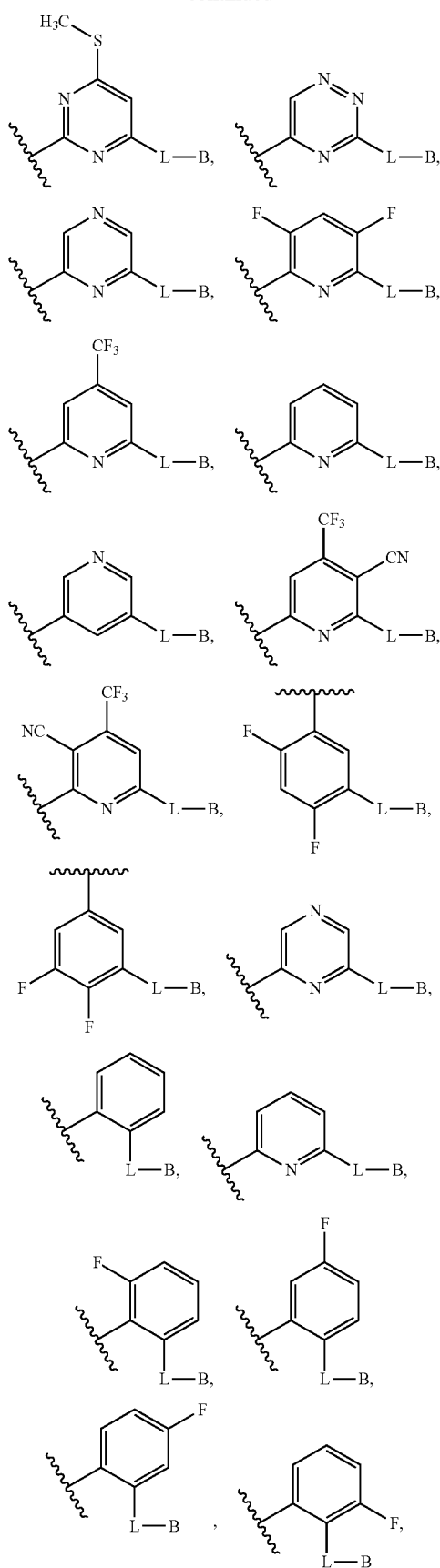
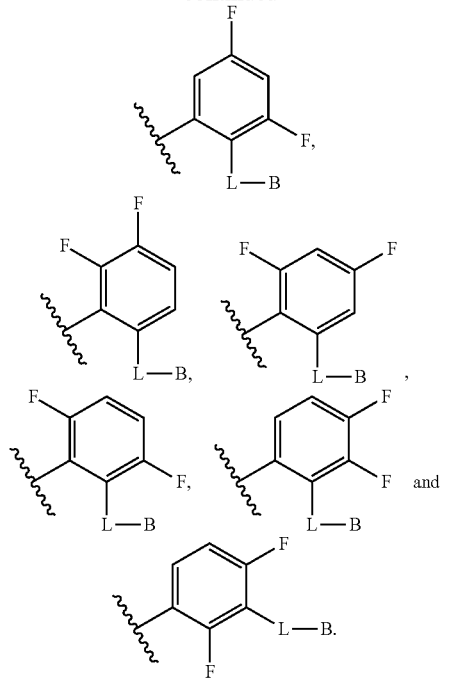
In an aspect B is selected from:
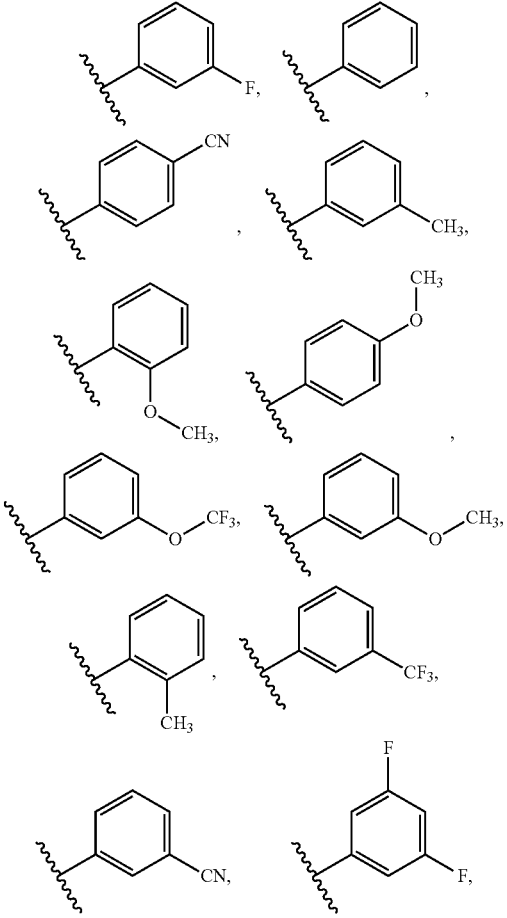

-continued
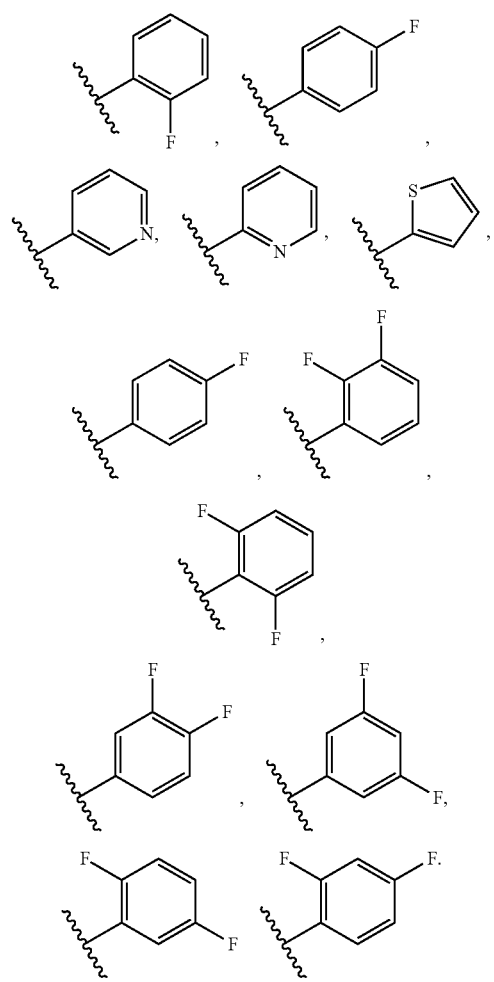
In an aspect A-L-B is selected from:
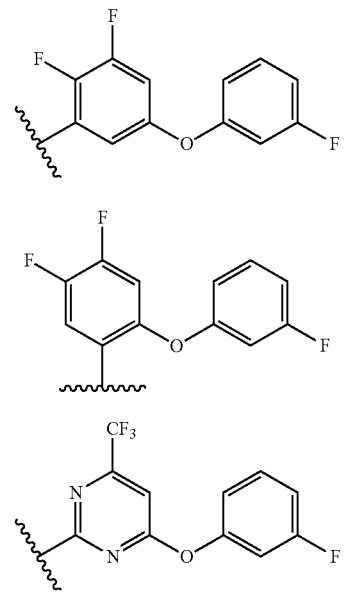
-continued
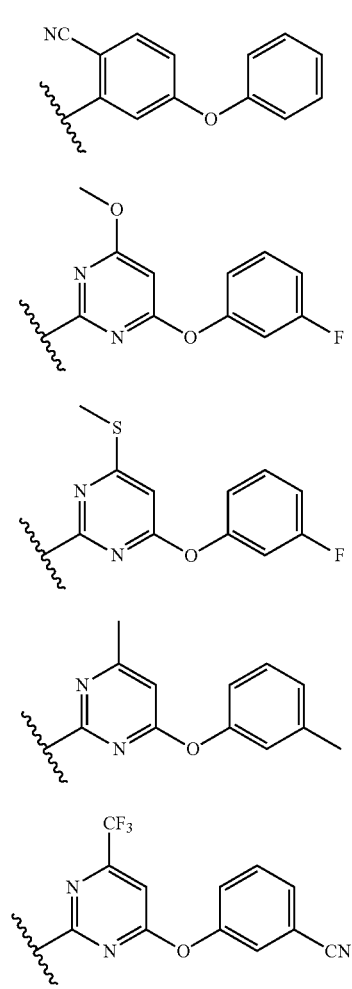
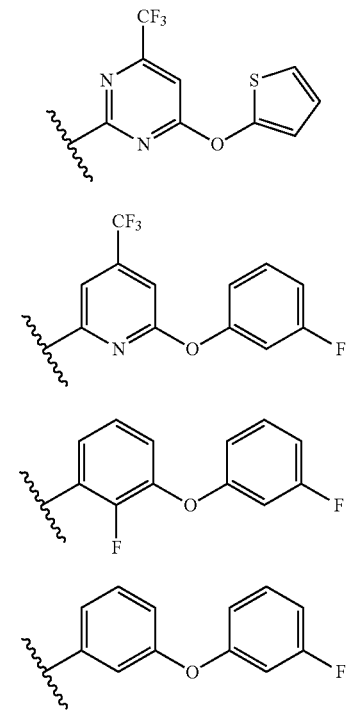

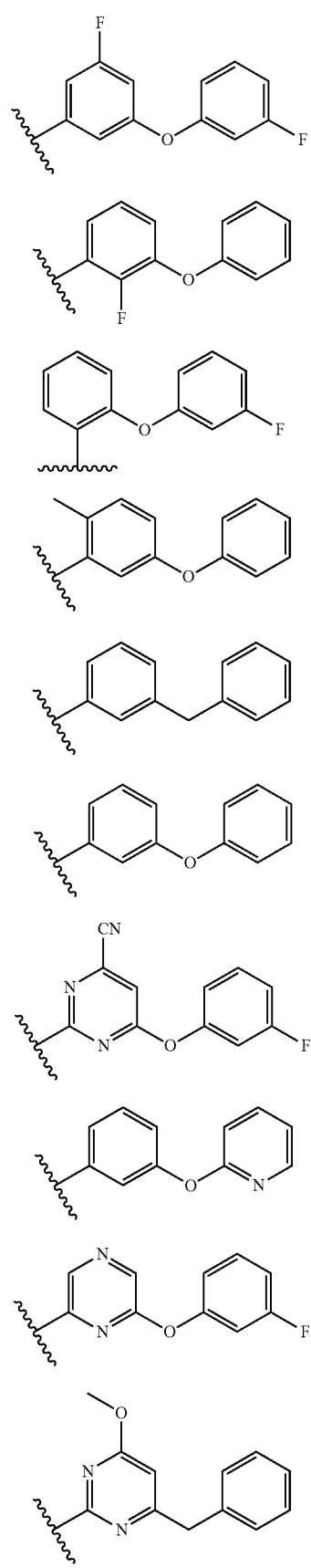
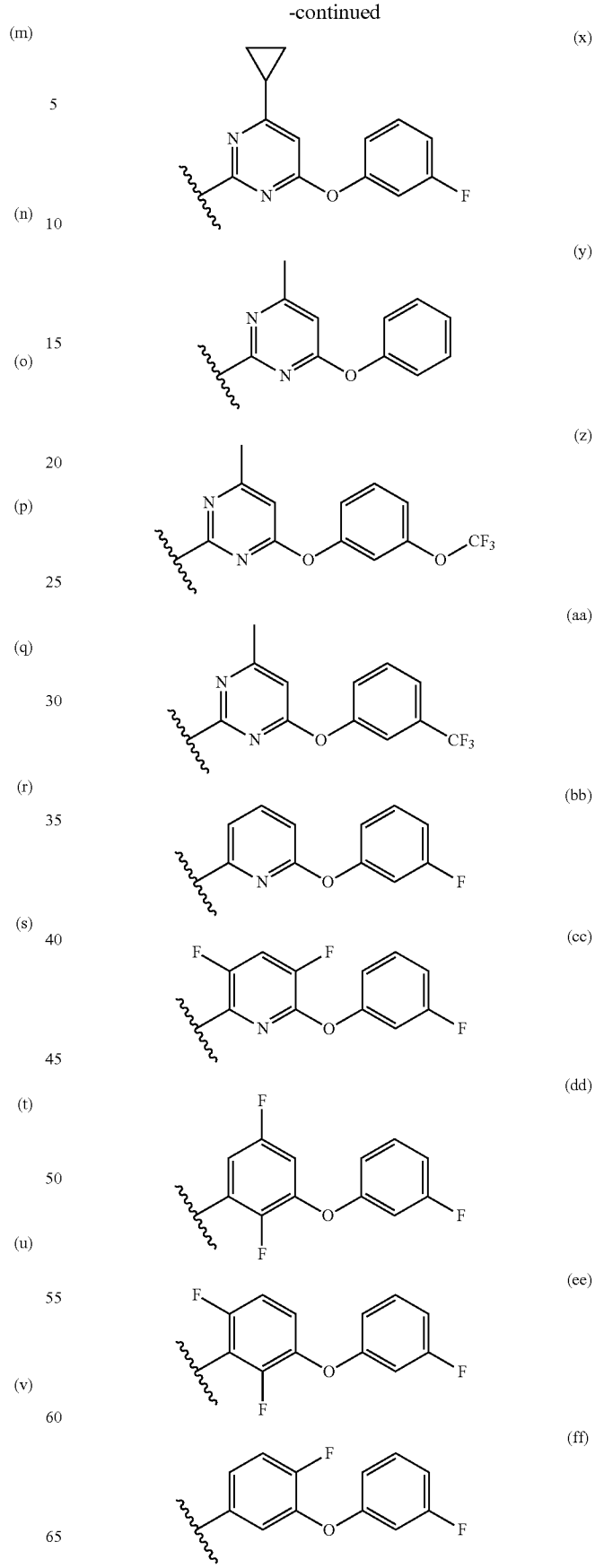

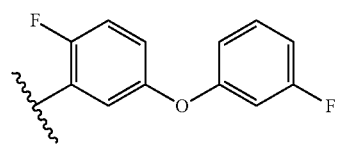
(gg)
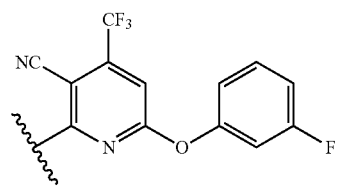
(hh)
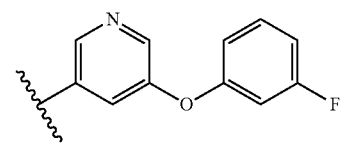
(jj)
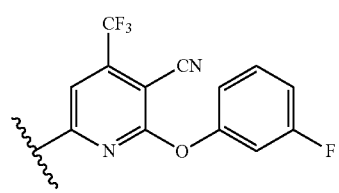
(kk)
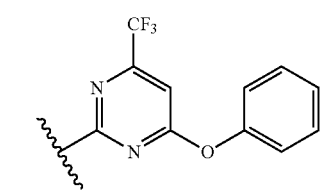
(ll)
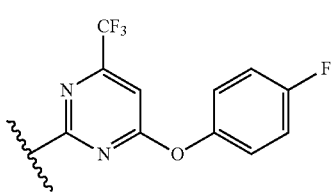
(mm)
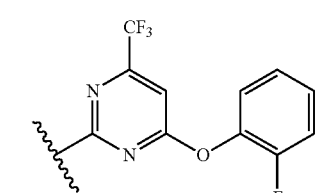
(nn)
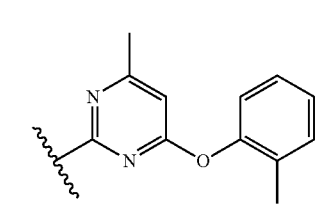
(oo)
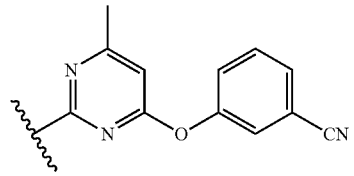
(pp)
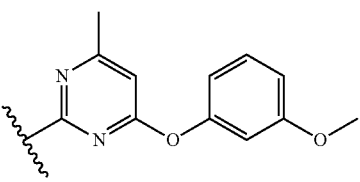
(qq)
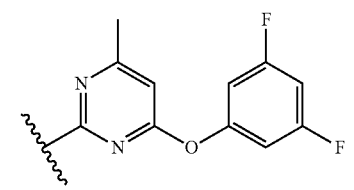
(rr)
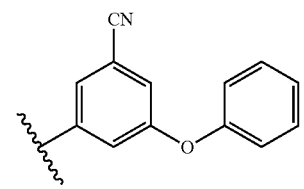
(ss)
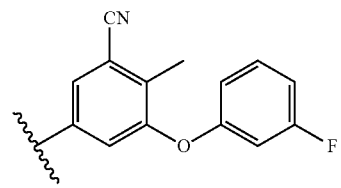
(tt)
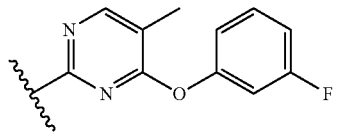
(uu)
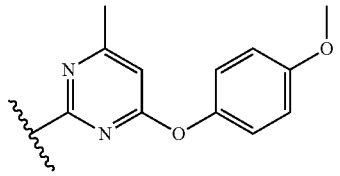
(vv)
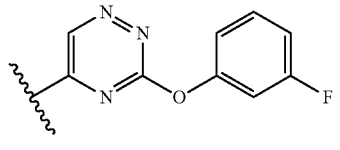
(xx)
(yy)

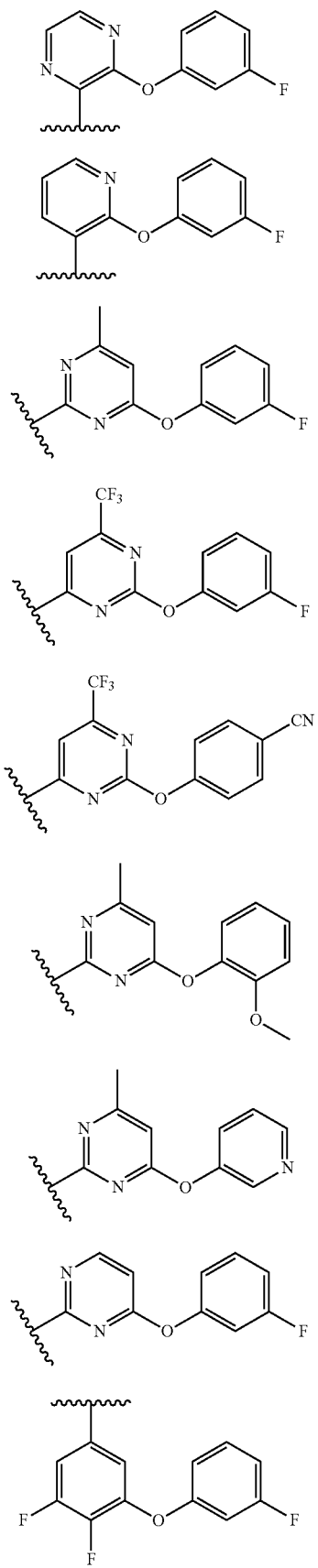

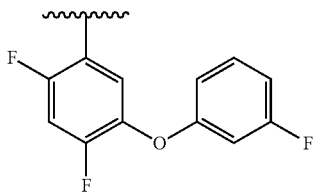

Preferably A-L-B is selected from the group consisting of (a), (b), (c), (d), (e), (f), (g), (j), (k), (m), (n), (s), (x), (y), (dd), (ee), (ll), (nn), (pp), (ss), (bbb), (ggg), (hhh) and (jjj).

More preferably A-L-B is selected from the group consisting of (a), (b), (c), (k), (n) and (dd).

In an aspect, the invention comprises a compound of formula I selected from:

4-[(dimethylamino)methyl]-1-[4-(3-fluorophenoxy)-6-(trifluoromethyl)pyrimidin-2-yl]piperidin-4-ol;
1-[4-(3-fluorophenoxy)-6-(trifluoromethyl)pyrimidin-2-yl]-4-(pyrrolidin-1-ylmethyl)piperidin-4-ol;
4-[(cyclopropylamino)methyl]-1-[4-(3-fluorophenoxy)-6-(trifluoromethyl)pyrimidin-2-yl]piperidin-4-ol;
4-{[cyclopropyl(methyl)amino]methyl}-1-[4-(3-fluorophenoxy)-6-(trifluoromethyl)pyrimidin-2-yl]piperidin-4-ol;
1-[4-(3-fluorophenoxy)-6-(trifluoromethyl)pyrimidin-2-yl]-4-[(methylamino)methyl]piperidin-4-ol;
4-[(3,3-difluoropyrrolidin-1-yl)methyl]-1-[4-(3-fluorophenoxy)-6-(trifluoromethyl)pyrimidin-2-yl]piperidin-4-ol;
4-(1,4-diazepan-1-ylmethyl)-1-[4-(3-fluorophenoxy)-6-(trifluoromethyl)pyrimidin-2-yl]piperidin-4-ol;
4-[(2,5-dimethylpyrrolidin-1-yl)methyl]-1-[4-(3-fluorophenoxy)-6-(trifluoromethyl)pyrimidin-2-yl]piperidin-4-ol;
4-[(tert-butylamino)methyl]-1-[4-(3-fluorophenoxy)-6-(trifluoromethyl)pyrimidin-2-yl]piperidin-4-ol;
1-({1-[4-(3-fluorophenoxy)-6-(trifluoromethyl)pyrimidin-2-yl]-4-hydroxypiperidin-4-yl}methyl)pyrrolidin-2-one;
4-(aminomethyl)-1-[4-(3-fluorophenoxy)-6-(trifluoromethyl) pyrimidin-2-yl]piperidin-4-ol;
{4-fluoro-1-[4-(3-fluorophenoxy)-6-(trifluoromethyl) pyrimidin-2-yl]piperidin-4-yl}methanamine;
4-(aminomethyl)-1-[3-fluoro-5-(3-fluorophenoxy)phenyl]piperidin-4-ol;
4-(aminomethyl)-1-[2,5-difluoro-3-(3-fluorophenoxy)phenyl]piperidin-4-ol;
4-(aminomethyl)-1-(2-fluoro-3-phenoxyphenyl)piperidin-4-ol;
4-(aminomethyl)-1-[2-fluoro-3-(3-fluorophenoxy)phenyl] piperidin-4-ol;
4-(aminomethyl)-1-[2,3-difluoro-5-(3-fluorophenoxy)phenyl]piperidin-4-ol;
4-(aminomethyl)-1-[3,4-difluoro-5-(3-fluorophenoxy)phenyl]piperidin-4-ol;
{4-amino-1-[4-(3-fluorophenoxy)-6-(trifluoromethyl)pyrimidin-2-yl]piperidin-4-y}methanol;
N-({1-[4-(3-fluorophenoxy)-6-(trifluoromethyl) pyrimidin-2-yl]-4-hydroxypiperidin-4-y}methyl)-2-methylpropanamide;
2-cyclopropyl-N-({1-[4-(3-fluorophenoxy)-6-(trifluoromethyl) pyrimidin-2-yl]-4-hydroxypiperidin-4-yl}methyl)acetamide;
N-({1-[4-(3-fluorophenoxy)-6-(trifluoromethyl) pyrimidin-2-yl]-4-hydroxypiperidin-4-y}methyl)-2-(propan-2-yloxy)acetamide;
N-({1-[4-(3-fluorophenoxy)-6-(trifluoromethyl) pyrimidin-2-yl]-4-hydroxypiperidin-4-yl}methyl)acetamide;

N-({1-[4-(3-fluorophenoxy)-6-(trifluoromethyl)pyrimidin-2-yl]-4-hydroxypiperidin-4-yl}methyl)azetidine-3-carboxamide;
N-({1-[4-(3-fluorophenoxy)-6-(trifluoromethyl)pyrimidin-2-yl]-4-hydroxypiperidin-4-yl}methyl)benzamide;
N-({1-[4-(3-fluorophenoxy)-6-(trifluoromethyl) pyrimidin-2-yl]-4-hydroxypiperidin-4-y}methyl)-1H-pyrazole-4-carboxamide;
N-({1-[4-(3-fluorophenoxy)-6-(trifluoromethyl)pyrimidin-2-yl]-4-hydroxypiperidin-4-yl}methyl)pyrazine-2-carboxamide;
2-amino-N-({1-[4-(3-fluorophenoxy)-6-(trifluoromethyl)pyrimidin-2-yl]-4-hydroxypiperidin-4-yl}methyl)acetamide;
(3S)-3-[(cyclopropylamino)methyl]-1-[4-(3-fluorophenoxy)-6-(trifluoromethyl)pyrimidin-2-yl]pyrrolidin-3-ol;
(3R)-3-[(cyclopropylamino)methyl]-1-[4-(3-fluorophenoxy)-6-(trifluoromethyl)pyrimidin-2-yl]pyrrolidin-3-ol;
3-(aminomethyl)-1-[4-(3-fluorophenoxy)-6-(trifluoromethyl)pyrimidin-2-yl]pyrrolidin-3-ol;
N-({1-[4-(3-fluorophenoxy)-6-(trifluoromethyl)pyrimidin-2-yl]-3-hydroxypyrrolidin-3-yl}methyl)-2-methylpropanamide;
N-({1-[4-(3-fluorophenoxy)-6-(trifluoromethyl)pyrimidin-2-yl]-3-hydroxypyrrolidin-3-yl}methyl)azetidine-3-carboxamide;
4-(3-fluorophenoxy)-2-{3H,4H,5H,6H,7H-imidazo[4,5-c]pyridin-5-yl}-6-(trifluoromethyl)pyrimidine;
6-[4-(3-fluorophenoxy)-6-(trifluoromethyl)pyrimidin-2-yl]-decahydro-1,6-naphthyridine;
and pharmaceutically acceptable salts and solvates thereof.

Preferably, the invention comprises a compound of formula I selected from:
4-[(cyclopropylamino)methyl]-1-[4-(3-fluorophenoxy)-6-(trifluoromethyl)pyrimidin-2-yl]piperidin-4-ol;
1-[4-(3-fluorophenoxy)-6-(trifluoromethyl)pyrimidin-2-yl]-4-[(methylamino)methyl]piperidin-4-ol;
4-(1,4-diazepan-1-ylmethyl)-1-[4-(3-fluorophenoxy)-6-(trifluoromethyl)pyrimidin-2-yl]piperidin-4-ol;
4-[(tert-butylamino)methyl]-1-[4-(3-fluorophenoxy)-6-(trifluoromethyl)pyrimidin-2-yl]piperidin-4-ol;
4-(aminomethyl)-1-[4-(3-fluorophenoxy)-6-(trifluoromethyl)pyrimidin-2-yl]piperidin-4-ol;
{4-fluoro-1-[4-(3-fluorophenoxy)-6-(trifluoromethyl)pyrimidin-2-yl]piperidin-4-yl}methanamine;
4-(aminomethyl)-1-[3-fluoro-5-(3-fluorophenoxy)phenyl]piperidin-4-ol;
4-(aminomethyl)-1-[2,5-difluoro-3-(3-fluorophenoxy)phenyl]piperidin-4-ol;
4-(aminomethyl)-1-(2-fluoro-3-phenoxyphenyl)piperidin-4-ol;
4-(aminomethyl)-1-[2-fluoro-3-(3-fluorophenoxy)phenyl]piperidin-4-ol;
4-(aminomethyl)-1-[2,3-difluoro-5-(3-fluorophenoxy)phenyl]piperidin-4-ol;
4-(aminomethyl)-1-[3,4-difluoro-5-(3-fluorophenoxy)phenyl]piperidin-4-ol;
{4-amino-1-[4-(3-fluorophenoxy)-6-(trifluoromethyl)pyrimidin-2-yl]piperidin-4-yl}methanol;
N-({1-[4-(3-fluorophenoxy)-6-(trifluoromethyl)pyrimidin-2-yl]-4-hydroxypiperidin-4-yl}methyl)-2-methylpropanamide;
2-cyclopropyl-N-({1-[4-(3-fluorophenoxy)-6-(trifluoromethyl)pyrimidin-2-yl]-4-hydroxypiperidin-4-yl}methyl)acetamide;
N-({1-[4-(3-fluorophenoxy)-6-(trifluoromethyl)pyrimidin-2-yl]-4-hydroxypiperidin-4-yl}methyl)-2-(propan-2-yloxy)acetamide;
N-({1-[4-(3-fluorophenoxy)-6-(trifluoromethyl)pyrimidin-2-yl]-4-hydroxypiperidin-4-yl}methyl)acetamide;
N-({1-[4-(3-fluorophenoxy)-6-(trifluoromethyl)pyrimidin-2-yl]-4-hydroxypiperidin-4-yl}methyl)azetidine-3-carboxamide;
N-({1-[4-(3-fluorophenoxy)-6-(trifluoromethyl)pyrimidin-2-yl]-4-hydroxypiperidin-4-yl}methyl)benzamide;
N-({1-[4-(3-fluorophenoxy)-6-(trifluoromethyl)pyrimidin-2-yl]-4-hydroxypiperidin-4-yl}methyl)-1H-pyrazole-4-carboxamide;
N-({1-[4-(3-fluorophenoxy)-6-(trifluoromethyl)pyrimidin-2-yl]-4-hydroxypiperidin-4-yl}methyl)pyrazine-2-carboxamide;
2-amino-N-({1-[4-(3-fluorophenoxy)-6-(trifluoromethyl)pyrimidin-2-yl]-4-hydroxypiperidin-4-yl}methyl)acetamide;
3-[(cyclopropylamino)methyl]-1-[4-(3-fluorophenoxy)-6-(trifluoromethyl)pyrimidin-2-yl]pyrrolidin-3-ol;
(3S)-3-[(cyclopropylamino)methyl]-1-[4-(3-fluorophenoxy)-6-(trifluoromethyl)pyrimidin-2-yl]pyrrolidin-3-ol;
(3R)-3-[(cyclopropylamino)methyl]-1-[4-(3-fluorophenoxy)-6-(trifluoromethyl)pyrimidin-2-yl]pyrrolidin-3-ol;
3-(aminomethyl)-1-[4-(3-fluorophenoxy)-6-(trifluoromethyl)pyrimidin-2-yl]pyrrolidin-3-ol;
N-({1-[4-(3-fluorophenoxy)-6-(trifluoromethyl)pyrimidin-2-yl]-3-hydroxypyrrolidin-3-yl}methyl)azetidine-3-carboxamide;
4-(3-fluorophenoxy)-2-{3H,4H,5H,6H,7H-imidazo[4,5-c]pyridin-5-yl}-6-(trifluoromethyl)pyrimidine;
and pharmaceutically acceptable salts and solvates thereof.

Therapeutic Applications

As previously mentioned, the compounds of the present invention are potent inhibitors of dopamine transporters. They are therefore useful in the treatment of disease conditions for which over-activity of a dopamine transporter is a causative factor.

The compounds of the present invention are preferably selective for dopamine transporters over noradrenaline and serotonin transporters. In the present context, the word "selective" means the compound has an IC50 value that is at least 10-fold selective for the dopamine transporter than for each of the noradrenaline and serotonin transporters, preferably at least 20-fold, more preferably at least 30-fold, even more preferably 50-fold, most preferably 100-fold higher for the dopamine transporter than for each of the noradrenaline and serotonin transporters.

Accordingly, the present invention provides a compound of formula I for use in therapy.

The present invention also provides for the use of a compound of formula I in the manufacture of a medicament for the treatment or prevention of a condition, disease or disorder ameliorated by inhibition of a dopamine transporter.

The present invention also provides a compound of formula I for use in the treatment or prevention of a condition, disease or disorder ameliorated by inhibition of a dopamine transporter.

The present invention also provides a method of treatment of a condition, disease or disorder ameliorated by inhibition of a dopamine transporter comprising administration to a subject in need thereof a therapeutically effective amount of a compound of formula I.

In one aspect, the condition, disease or disorder ameliorated by inhibition of a dopamine transporter includes sexual dysfunction, affective disorders, anxiety, depression, Tourette syndrome, Angelman syndrome, attention deficit disorder (ADD), attention deficit hyperactivity disorder (ADHD), obesity, pain, obsessive-compulsive disorder, movement disorders, CNS disorders, sleep disorders, narcolepsy, conduct disorder, substance abuse (including smoking cessation), eating disorders, chronic fatigue and impulse control disorders.

In a particular aspect, the condition, disease or disorder is selected from ADD, ADHD and binge eating disorder.

In the context of the present invention, references herein to "treatment" include references to curative, palliative and prophylactic treatment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Combination Therapy

When combination therapy is employed, the compounds of the present invention and said combination agents may exist in the same or different pharmaceutical compositions, and may be administered separately, sequentially or simultaneously.

The compounds of the invention may be administered as a combination with at least one other active pharmaceutical ingredient for the treatment of mood disorders, disorders such as depression, refractory depression, bipolar depression, and psychotic depression. Such a pharmaceutical combination may be in the form of a unit dosage form or it may be in the form of a package comprising the at least two active components separately. In a further aspect, the invention relates to such pharmaceutical combinations. In a further aspect, the invention therefore relates to a pharmaceutical combination comprising a therapeutically effective amount of an compound of the invention and a second active substance, for simultaneous or sequential administration.

In an aspect the invention relates to a compound of the invention in combination with another therapeutic agent wherein the other therapeutic agent is selected from:
a tricyclic antidepressant (Amitriptyline, Clomipramine, Doxepin, Imipramine, Trimipramine Desipramine, Nortriptyline, Protriptyline),
tetracyclic antidepressant (Amoxapine, Maprotiline, Mazindol, Mianserin, Mirtazapine, Setiptiline), selective serotonin reuptake inhibitor (Citalopram, Escitalopram, Paroxetine, Fluoxetine, Fluvoxamine, Sertraline),
serotonin antagonist and reuptake inhibitors (Etoperidone, Nefazodone, Trazodone), selective norepinephrine reuptake inhibitor (Atomoxetine, Reboxetine, Viloxazine),
serotonin and norepinephrine reuptake inhibitor (Desvenlafaxine, Duloxetine, Milnacipran, Venlafaxine),
monoamine oxidase inhibitor (Isocarboxazid, Phenelzine, Selegiline, Tranylcypromine, Moclobemide, Pirlindole),
mood stabilisers (Lithium, Valproic Acid, Lamotrigine, Carbamazepine, Oxcarbazepine)
and/or antipsychotics (Clozapine, Olanzapine, Risperidone, Quetiapine, Ziprasidone, Amisulpride, Asenapine, Paliperidone, Iloperidone, Zotepine, Sertindole, Lurasidone, Aripiprazole, Haloperidol, Droperidol, Chlorpromazine, Fluphenazine Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol).

In addition to treating the primary disease symptoms or the therapeutic lag phase, DAT inhibitors may be used adjunctively to treat medication induced sedation, common in diseases such as bipolar depression as well as sexual dysfunction which is a common side effect of antidepressant treatment, particularly SSRIs.

The compounds of the invention may be administered as a combination with at least one other active pharmaceutical ingredient for the treatment of smoking cessation and mitigation of nicotine withdrawal and weight gain. Such a pharmaceutical combination may be in the form of a unit dosage form or it may be in the form of a package comprising the at least two active components separately. In a further aspect, the invention relates to such pharmaceutical combinations.

In a further aspect, the invention therefore relates to a pharmaceutical combination comprising a therapeutically effective amount of an compound of the invention and a second active substance, for simultaneous or sequential administration.

In an aspect, the invention relates to a compound of the invention in combination with another therapeutic agent wherein the other therapeutic agent is selected from:
Nicotine replacement therapies (nicotine patches, nicotine gum, nicotine sprays, nicotine sublingual tablets, nicotine lozenges and nicotine inhalers), nicotinic full/partial agonists (Nicotine, Varenicline, Lobeline), opioid antagonists/inverse agonists (Naloxone, Naltrexone, Buprenorphine).

The compounds of the invention may be administered as a combination with at least one other active pharmaceutical ingredient for the treatment of ADHD. Such a pharmaceutical combination may be in the form of a unit dosage form or it may be in the form of a package comprising the at least two active components separately. In a further aspect, the invention relates to such pharmaceutical combinations.

In a further aspect, the invention therefore relates to a pharmaceutical combination comprising a therapeutically effective amount of an compound of the invention and a second active substance, for simultaneous or sequential administration.

In an aspect, the invention relates to a compound of the invention in combination with another therapeutic agent wherein the other therapeutic agent is selected from:
Norepinephrine reuptake inhibitors (Atomoxetine, Reboxetine, Viloxazine), alpha-adrenoceptor agonists (Guanfacine, Clonidine).

The compounds of the invention may be administered as a combination with at least one other active pharmaceutical ingredient for the treatment of movement disorders such as Parkinson's disease and Restless Leg Syndrome. Such a pharmaceutical combination may be in the form of a unit dosage form or it may be in the form of a package comprising the at least two active components separately. In a further aspect, the invention relates to such pharmaceutical combinations.

In a further aspect, the invention therefore relates to a pharmaceutical combination comprising a therapeutically effective amount of an compound of the invention and a second active substance, for simultaneous or sequential administration.

In an aspect, the invention relates to a compound of the invention in combination with another therapeutic agent wherein the other therapeutic agent is selected from:

A dopamine precursor (L-dopa) a dopaminergic agent (Levodopa-carbidopa, Levodopa-benzerazide), a dopaminergic and anti-cholinergic agent (amantadine), an anti-cholinergic agent (trihexyphenidyl, benztropine, ethoprorazine, or procyclidine), a dopamine agonist (apomorphine, bromocriptine, cabergoline, lisuride, pergolide, pramipexole, or ropinirole), a MAO-B (monoamine oxidase B) inhibitor (selegiline, rasageline or deprenyl0, a COMT (catechol O-methyltransferase) inhibitor (tolcapone or entacapone.

Definitions

"Alkyl" is as defined above and includes saturated hydrocarbon residues including:
- linear groups of up to 6 carbon atoms ($C_1$-$C_6$), or of up to 4 carbon atoms ($C_1$-$C_4$). Examples of such alkyl groups include, but are not limited, to $C_1$-methyl, $C_2$-ethyl, $C_3$-propyl and $C_4$-n-butyl.
- branched groups of between 3 and 6 carbon atoms ($C_3$-$C_6$), or of up to 4 carbon atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

each optionally substituted as stated above.

"Cycloalkyl" is as defined above and includes monocyclic saturated hydrocarbon of between 3 and 7 carbon atoms, or from 3 to 6 carbon atoms, or from 3 to 5 carbon atoms, or from 3 to 4 carbon atoms. Examples of suitable monocyclic cycloalkyl groups include cyclopropyl, cyclobutyl, cyclopentyl, cyclohexyl and cycloheptyl. Cycloalkyl is optionally substituted as stated above.

"Alkylene" is a bivalent $C_{1-3}$ straight-chained alkyl radical, such as —$(CH_2)$—, —$(CH_2)_2$—, —$(CH_2)_3$— or a bivalent $C_{3-4}$ branched alkyl radical such as —$CH(CH_3)CH$, $CH_2CH(CH_3)$—, —$CH(CH_3)CH(CH_3)$—. Alkylene is optionally substituted as stated above.

"Alkoxy" is as defined above and includes O-linked hydrocarbon residues including:
- linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.
- branched groups of between 3 and 6 carbon atoms ($C_3$-$C_6$) or of between 3 and 4 carbon atoms ($C_3$-$C_4$). Examples of such alkoxy groups include, but are not limited to, $C_3$-iso-propoxy, and $C_4$-sec-butoxy and tert-butoxy.

each optionally substituted as stated above.

"Heteroaryl" is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, pyridinyl, pyridazinyl, pyrimidinyl and pyrazinyl (optionally substituted as stated above). Preferably heteroaryl is selected from pyridyl, pyrazinyl, pyrimidinyl and 1,2,4-triazinyl optionally substituted as stated above. Unless otherwise stated pyrimidinyl refers to 1,3-pyrimidinyl. Unless otherwise stated (e.g. by a chemical formula) when A is pyrimidinyl it is attached to the heterocyclic backbone at the 2-position. Unless other stated when B is pyrimidinyl it is attached to L at the 2-position.

"Heterocyclyl" is defined above. Examples of suitable heterocyclyl groups include aziridinyl, azetidinyl, pyrrolidinyl, imidazolidinyl, imidazolyl, morpholine, thiomorpholine pyrazolidinyl, piperidinyl and piperazinyl (optionally substituted as stated above).

The term "O-linked", such as in "O-linked hydrocarbon residue", means that the hydrocarbon residue is joined to the remainder of the molecule via an oxygen atom.

In groups such as —CN and —$CH_2CH(CH_3)$—, "—" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in 'The Practice of Medicinal Chemistry, $2^{nd}$ Ed. pp 561-585 (2003) and in F. J. Leinweber, *Drug Metab. Res.*, 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Compounds of the invention may exist in one or more geometrical, optical, enantiomeric, diastereomeric, conformational and tautomeric forms, including but not limited to cis- and trans-forms, E- and Z-forms, R-, S- and meso-forms, keto- and enol-forms, and conformers. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

An example of a compound of the invention that exhibits optical isomerism is 3-[(cyclopropylamino)methyl]-1-[4-(3-fluorophenoxy)-6-(trifluoromethyl)pyrimidin-2-yl]pyrrolidin-3-ol. The present invention therefore encompasses the enantiomeric forms of this compound, as illustrated below.

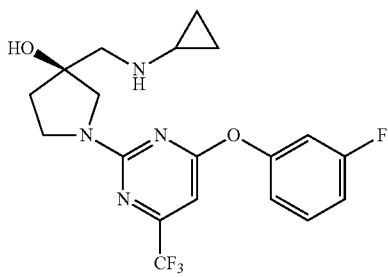

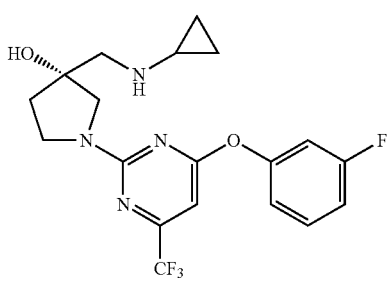

Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

General Methods

The compounds of formula I should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula I and a pharmaceutically acceptable carrier, diluent or excipient.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula I used in the preparation of parenteral solutions may be increased by the use of appropriate formulation techniques, such as the incorporation of co-solvents and/or solubility-enhancing agents such as surfactants, micelle structures and cyclodextrins.

In one aspect, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below.

Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvent. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The compounds according to general formula I can be prepared using conventional synthetic methods for example, but not limited to, the routes outlined in the schemes below.

i) Synthesis of Heterocyclic Systems

Scheme A

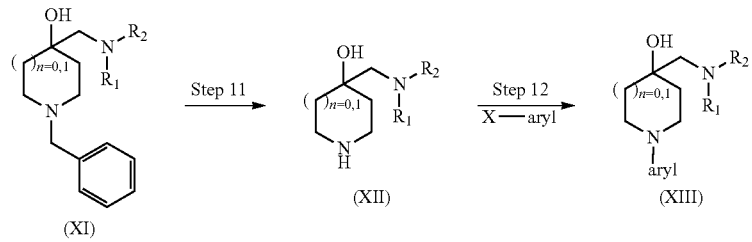

-continued
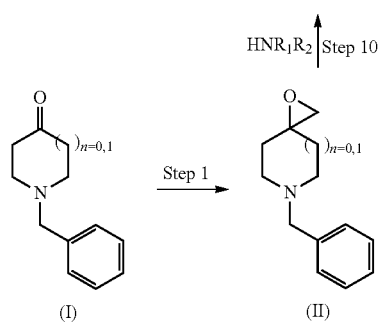
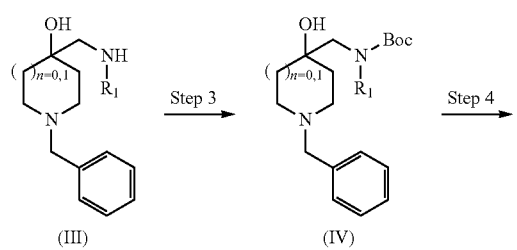
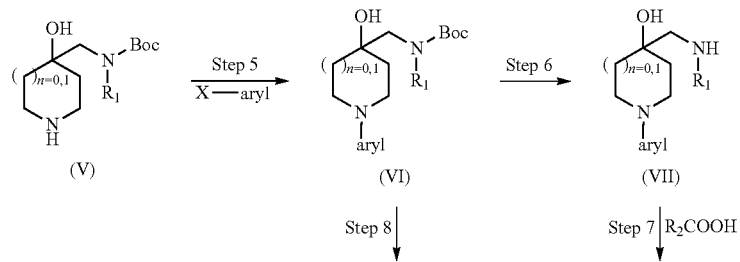
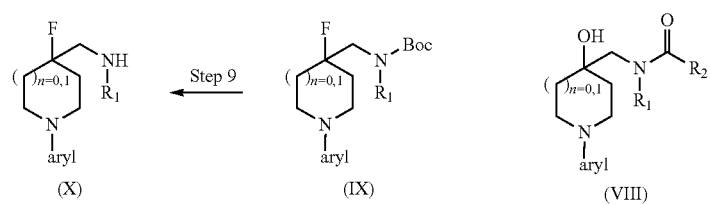

Step 1
Compound of formula II may be obtained by Corey-Chaykovsky epoxidation of compound I (commercially available from Sigma-Aldrich) using trimethylsulfoxonium iodide and a inorganic base, e. g. NaH, carrying out the reaction in a suitable solvent, such as DMSO, at room temperature. The reaction takes about 1 to about 2 hours to complete.

Step 2
Compound of formula III may be obtained by epoxide opening of compound II using primary amines, such as methylamine, carrying out the reaction in a mixture of MeOH/water, at room temperature. The reaction takes from about 1 to about 16 hours to complete.

Step 3
Compound of formula IV may be obtained by N-protection of compound III under standard literature conditions such as by reaction with Di-tert-butyl dicarbonate, with or without the presence of a suitable base such as triethylamine, carrying out the reaction in a suitable solvent, e.g. DCM, typically at room temperature. The reaction takes about 1 to about 16 hours to complete.

Step 4
Compound of formula V may be obtained from compound IV by removing the benzyl group by hydrogenolysis, e. g. using ammonium formate and palladium on carbon, in a suitable solvent such as methanol under reflux. The reaction takes about 1 hour.

Step 5
Compound VI can be obtained from compound V by SnAr substitution with the appropriate aryl halide in a suitable aprotic solvent, e. g. DMSO, in presence of an inorganic base, such as K2CO3. The reaction proceeds in a temperature range of about 25 to about 100° C. and takes about 1 to about 12 hours. Alternatively the compound VI can be obtained from Buchwald reaction with the appropriate aryl halide in the presence of suitable transition metal catalyst, e. g. $Pd_2(dba)_3$, a suitable ligand such as DavePhos, a suitable base, such as $K_3PO_4$ and like, in a suitable solvent, e. g. DME. The reaction is carrying out at a temperature from about 100° C. to about 110° C. and takes about 12 hours.

Step 6
Compound VII can be obtained from compound VI by removing the Boc group under acidic conditions, e. g. TFA in dichloromethane solution, typically at room temperature. The reaction takes about 1 hour.

Step 7
Compound VIII can be obtained from compound VII by coupling with the appropriate carboxylic acid (such as isobutyric acid) in the presence of coupling agents such as EDC HCl and HOBt and an organic base, e. g. TEA. The reaction is carrying out in a suitable solvent such as dichloromethane, typically at room temperature. The reaction takes from about 3 hours to about 12 hours.

Step 8
Compound IX can be obtained treating compound VI with a fluorinated agent, such as Deoxofluor®, in a suitable solvent, such as dichloromethane, typically at 0° C. The reaction takes about 1 hour.

Step 9
Compound IX can be obtained from compound X by removing the Boc group under acidic conditions, e. g. TFA in dichloromethane solution, typically at room temperature. The reaction takes about 1 hour.

Step 10
Compound of formula XI may be obtained by epoxide opening of compound II using secondary amines, such as pyrrolidine, carrying out the reaction in a mixture of MeOH/water, at room temperature. The reaction takes from about 2 to about 16 hours to complete.

Step 11
Compound of formula XII may be obtained from compound X by removing the benzyl group by hydrogenolysis, e. g. using ammonium formate and palladium on carbon, in a suitable solvent such as methanol under reflux. The reaction takes about 1 hour.

Step 12
Compound XIII can be obtained from compound XII by SnAr substitution with the appropriate aryl halide in a suitable aprotic solvent, e. g. DMSO, in presence of an inorganic base, such as $K_2CO_3$. The reaction proceeds in a temperature range of about 45° C. to about 100° C. and takes about 1 to about 12 hours.

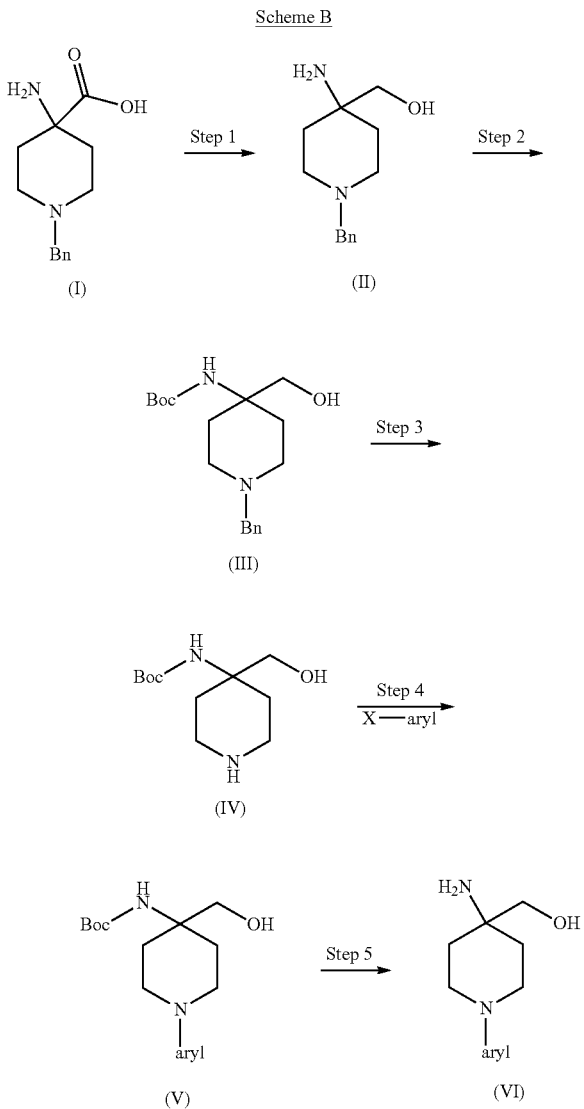

Scheme B

Step 1
Compound of formula II may be obtained by reduction of compound I (commercially available from Activate Scientific) using a suitable reducing agent, e. g. LiAlH$_4$, carrying out the reaction in a suitable solvent, such as THF under reflux. The reaction takes about 2 hours to complete.

Step 2

Compound of formula III may be obtained by N-protection of compound II under standard literature conditions such as by reaction with Di-tert-butyl dicarbonate, with the presence of a suitable base such as triethylamine, carrying out the reaction in a suitable solvent, e.g. DCM, typically at room temperature. The reaction takes about 2 hours to complete.

Step 3

Compound of formula IV may be obtained from compound III by removing the benzyl group by hydrogenolysis, e. g. using ammonium formate and palladium on carbon, in a suitable solvent such as methanol under reflux. The reaction takes about 1 hour.

Step 4

Compound V can be obtained from compound IV by SnAr substitution with the appropriate aryl halide in a suitable aprotic solvent, e. g. DMSO, in presence of an inorganic base, such as K$_2$CO$_3$. The reaction proceeds in a temperature of about 60° C. and takes about 1 hour.

Step 5

Compound VI can be obtained from compound V by removing the Boc group under acidic conditions, e. g. TFA in dichloromethane solution, typically at room temperature. The reaction takes about 1 hour.

ii) Synthesis of A-L-B Systems

Scheme 1

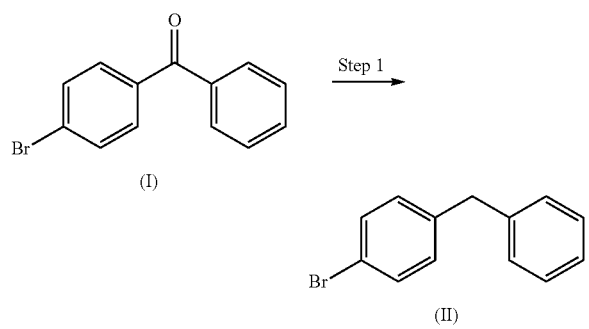

Step 1

Compound of formula II can be obtained by reduction of compound I, (3-bromophenyl)(phenyl)methanone, (commercially available from Sigma-Aldrich) with a suitable reducing system, such as NaBH$_4$ in presence of TFA, carrying out the reaction in a suitable solvent, e. g. dichloromethane, typically at room temperature. The reaction takes about 12 hours to complete.

Scheme 2

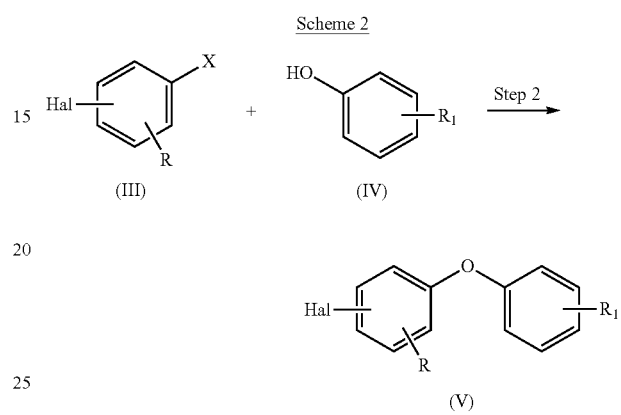

Step 2

Compound V can be obtained by Ullmann condensation between compounds III, the desired di-halogen benzene, such as 1,2-dibromo-4,5-difluorobenzene, and compound IV, the appropriate phenol, such as 3-fluorophenol, (both commercially available from Alfa-Aesar and Sigma-Aldrich respectively) in presence of a suitable catalyst, such as Cu, and a suitable base, e. g. KOH, typically at high temperature, from about 100 to about 150° C. The reaction takes about 14 hours to complete. Alternatively compound V may be obtained by SnAr reaction between compounds III and IV in presence of an inorganic base, such as K$_2$CO$_3$, a suitable solvent, e. g. DMSO, at a temperature between 25° C. and about 160° C., the reaction takes from about 20 to around 12 hours to complete.

Scheme 3

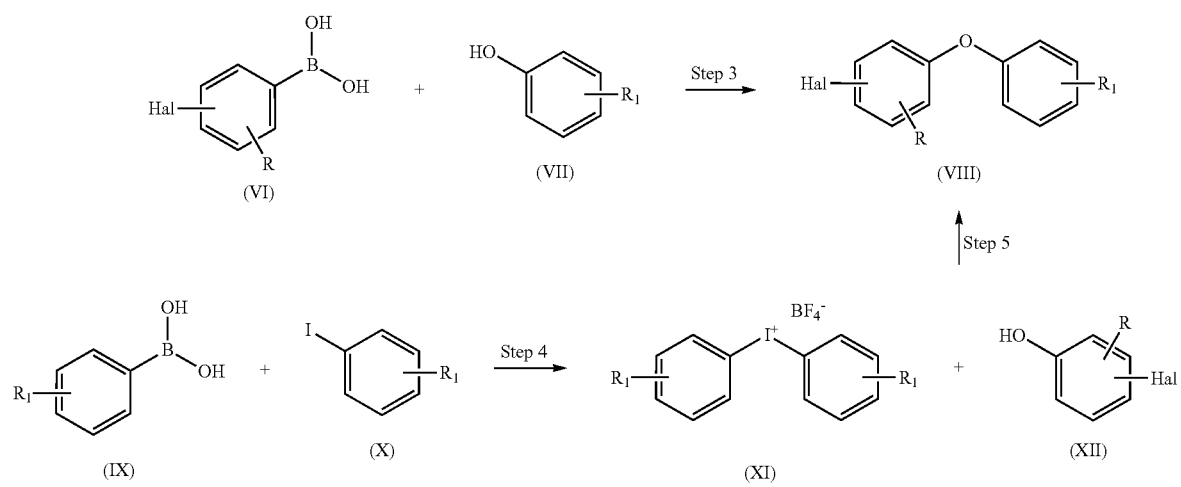

Step 3

Compound of formula VIII may be obtained via Chan-Lam coupling between compound VI, the desired boronic acid, such as phenyl boronic acid, and compound VII, the appropriate phenol, e. g. 3-bromo-2-fluorophenol (both commercially available from Sigma-Aldrich and Zentek respectively), in presence of a suitable catalyst, such as $Cu(OAc)_2$, a suitable base, e. g. triethylamine, typically at room temperature. The reaction takes about 16 hours to complete.

Step 4

Compound XI can be obtained by reaction between compound IX, the desired boronic acid, e. g. phenyl boronic acid, and compound X, the appropriate benzene iodide, such as iodobenzene, (both commercially available from Sigma-Aldrich), in presence of a suitable oxidant, such as m-CPBA, and $BF_3Et_2O$, carrying out the reaction in a suitable solvent, such as dichloromethane. The reaction proceeds at a temperature between 0° C. and room temperature and takes about 45 minutes to complete.

Step 5

Compound VIII may be obtained from compound XI by reaction with compound XII, a suitable phenol such as 3-fluorophenol, in presence of a suitable base, such as tBuOK, in a suitable solvent, usually THF, at a temperature between 0° C. and 40° C. The reaction takes about 1 hour.

Scheme 4

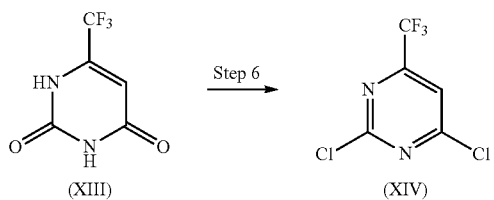

Step 6

Compound XIV can be obtained by chlorination of the commercially available (from Sigma-Aldrich) compound XIII, 6-(Trifluoromethyl)uracil, by treatment with a suitable chlorinating agent, such as $SOCl_2$ in a suitable solvent, e. g. DMF, carrying out the reaction usually at 80° C. for about 4 hours.

Scheme 5

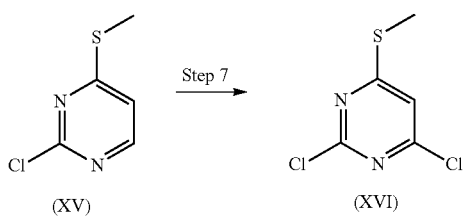

Step 7

Compound of formula XVI can be obtained by chlorination of compound XV, 2-chloro-4-(methylthio)pyrimidine (commercially available from Sigma-Aldrich), with N-chlorosuccinimide in presence of 2,2,6,6-Tetramethylpiperidinylmagnesium chloride lithium chloride complex solution in THF/Toluene, in a suitable solvent, such as THF, typically at room temperature. The reaction takes 4 hours to complete.

Scheme 6

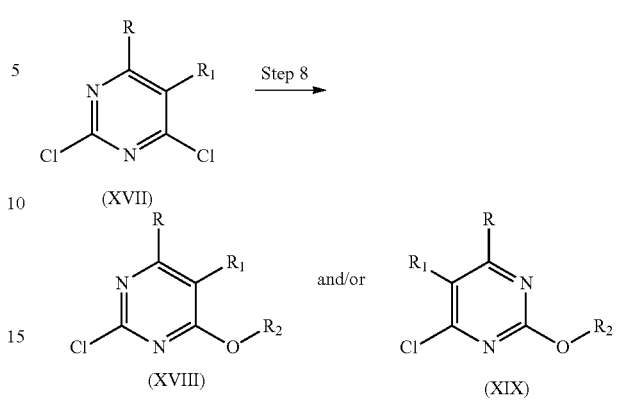

Step 8

Compounds of structure XVIII and XIX can be obtained via SnAr reaction between compound XVII, e. g. 2,4-dichloro-6-methylpyrimidine (commercially available from Sigma-Aldrich), or ad hoc prepared, and a suitable partner, such as 3-fluorophenol (commercially available from Sigma-Aldrich), the reaction typically proceeds in aprotic solvent, such as DMSO, in presence of a suitable base, such as $K_2CO_3$, at a temperature between 25° C. and 110° C. The reaction takes from about 20 min to about 12 hours to complete.

Scheme 7

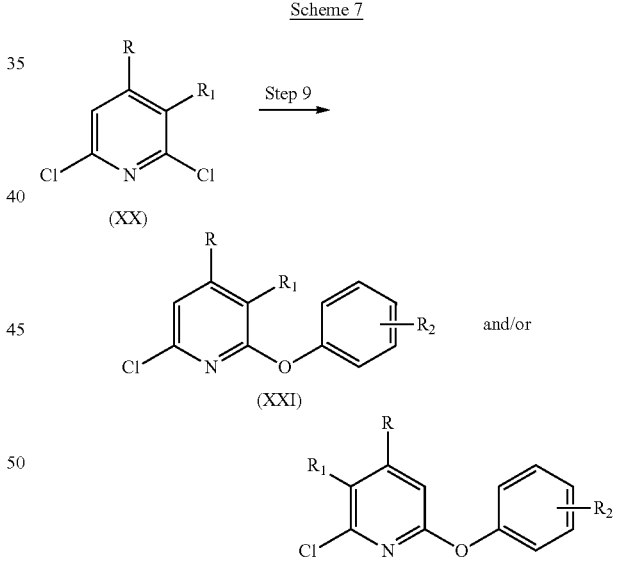

Step 9

Compounds of structure XXI and XXII can be obtained via SnAr reaction between compound XX, e. g. 2,6-dichloropyridine (commercially available from Sigma-Aldrich), and a suitable phenol, such as 3-fluorophenol (commercially available from Sigma-Aldrich). The reaction typically proceeds in aprotic solvent, such as DMSO, in presence of a suitable base, such as $K_2CO_3$, at a temperature between 25° C. and 103° C. The reaction takes from about 2 hours to about 48 hours to complete.

Scheme 8

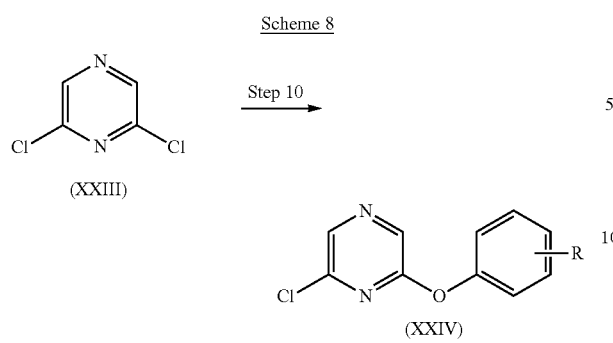

Scheme 10

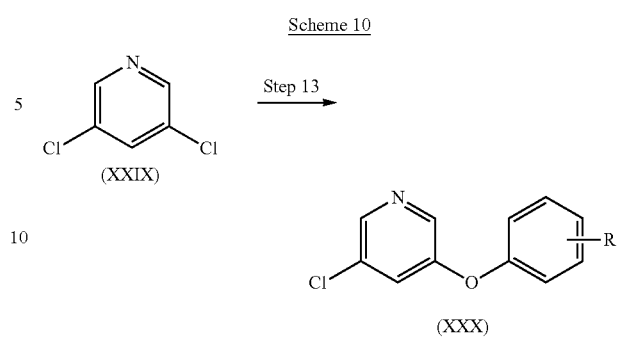

Step 10

Compound of structure XXIV can be obtained via SnAr reaction between compound XXIII, commercially available from Sigma-Aldrich, and a suitable phenol, such as 3-fluorophenol (commercially available from Sigma-Aldrich), the reaction typically proceeds in aprotic solvent, such as DMF, in presence of a suitable base, such as tBuOK, at a temperature of about 90° C. The reaction takes about 2 hours to complete.

Step 13

Compound of structure XXX can be obtained via SnAr reaction between compound XXIX, commercially available from Sigma-Aldrich, and a suitable phenol, such as 3-fluorophenol (commercially available from Sigma-Aldrich), the reaction typically proceeds in aprotic solvent, such as DMF, in presence of a suitable base, such as cesium carbonate, at a temperature of around 80° C. The reaction takes about 48 hours to complete.

Scheme 9

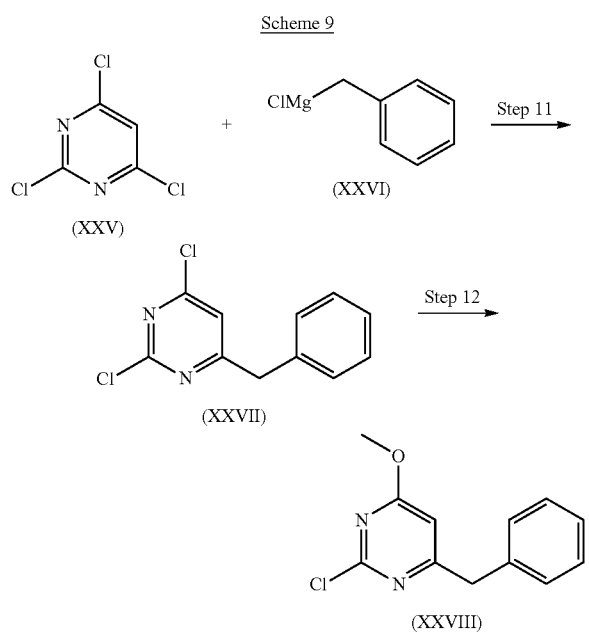

Step 11

Compound XXVII may be obtained by reaction between compound XXV, 2,4,6-trichloropyrimidine (commercially available from Sigma-Aldrich), and a Grignard reagent XXVI, such as benzylmagnesiumchloride, (both commercially available from Sigma-Aldrich). The reaction proceeds at a temperature between −78° C. and 20° C., and takes about 3 hours to complete.

Step 12

Compound XXVIII can be obtained by treatment of compound XXVII with MeONa, freshly obtained in situ by adding NaH in MeOH. The reaction is carried out in MeOH, typically at room temperature and takes about 1 hour to complete.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar or analogous" procedure, as will be appreciated by those skilled in the art, such procedure may involve minor variation, for example reaction temperature, reagent/solvent amount, reaction time, work-up conditions or chromatographic purification conditions. All temperatures refer to ° C.

Proton Magnetic Resonance (NMR) spectra may be typically recorded either on Varian instruments at 400 or 500 MHz, or on a Bruker instrument at 400 MHz.

Chemical shifts are expressed in parts of million (ppm, δ units). Chemical shifts are reported in ppm downfield (δ) from $Me_4Si$, used as internal standard, and are typically assigned as singlets (s), broad singlets (br.s.), doublets (d), doublets of doublets (dd), doublets of doublets of doublets (ddd), doublets of triplets (dt), triplets (t), triplets of doublets (td), quartets (q), or multiplets (m).

LCMS may be recorded under the following conditions:

DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative ES ionisation mode. The QC methods used were two, one operated under low pH conditions and another one operated under high pH conditions. Details of the method operated under low pH conditions were: column, Acquity BEH $C_{18}$, 1.7 μm, 2.1×50 mm or Acquity CSH $C_{18}$, 1.7 μm, 2.1×50 mm, the temperature column was 40° C.; mobile phase solvent A was milliQ water+0.1% HCOOH, mobile phase solvent B MeCN+0.1% HCOOH. The flow rate was 1 ml/min. The gradient table was t=0 min 97% A–3% B, t=1.5 min 0.1% A–99.9% B, t=1.9 min 0.1% A–99.9% B and t=2 min 97% A–3% B. The UV detection range was 210-350 nm and the $ES^+/ES^-$ range was 100-1000 amu. Details of the method operated under high pH conditions were the same of those listed above for the low pH method apart from: column Acquity BEH $C_{18}$, 1.7 μm, 2.1×50 mm; mobile phase solvent A was 10 mM acqueous solution of $NH_4HCO_3$ adjusted to pH=10 with ammonia, mobile phase solvent B MeCN.

Semipreparative mass directed autopurifications (MDAP) were carried out using Waters Fractionlynx™ systems operated under low or high pH chromatographic conditions. The stationary phases used were, XTerra C18, XBridge C18, Sunfire C18, XSelect C18, Gemini AXIA C18. The length of the columns was 5, 10 or 15 cm, while the internal diameter was 19, 21 or 30 mm. The particle size of the stationary phases was 5 or 10 μm. The purifications were carried out using low pH or high pH chromatographic conditions. The mobile phase solvent composition was the same used for QC analysis. The combinations stationary/mobile phases used were: XTerra, XBridge, Sunfire, XSelect—low pH mobile phases and XTerra, XBridge, Gemini AXIA—high pH mobile phases. All the purifications were carried out with the column kept at room T. The flow rate used was 17 or 20 ml/min for columns of internal diameter 19 or 21 mm and 40 or 43 ml/min for columns of internal diameter 30 mm. The trigger for the collection of the target species was the presence of the target m/z ratio value in the TIC MS signal. The gradient timetable was customised on the Rt behaviour of the target species.

Purification may also be performed using Biotage® Isolera or Biotage® SP1 flash chromatography systems, these instruments work with Biotage® KP-SIL cartridges and Biotage® KP-NH cartridges. Unless otherwise stated, all reactions are typically performed under inert atmosphere (for example under Nitrogen).

The following abbreviations are used in the text: EtOAc, AcOEt, EA=ethyl acetate, $Et_2O$=diethyl ether, MeOH=methanol; THF=tetrahydrofuran, Tlc refers to thin layer chromatography on silica plates, and dried refers to a solution dried over anhydrous sodium sulphate, r.t. (RT) refers to room temperature, DMSO=dimethyl sulfoxide; DMF=N,N'-dimethylformamide, DCM=dichloromethane, EtOH=ethanol, DCE=dichloroethane, DME=1,2-Dimethoxyethane, Cy, cHex=cyclohexane, TEA=triethylamine, DIPEA=N,N-Diisopropylethylamine, $Boc_2O$=Di-tert-butyl dicarbonate; TFA=trifluoroacetic acid, $Pd_2(dba)_3$=Tris(dibenzylideneacetone)dipalladium(0), EDC HCl=N-(3-Dimethylaminopropyl)-N'-ethylcarbodiimide hydrochloride, HOBt=1-Hydroxybenzotriazole hydrate, SCX Cartridge=Strong Cation Exchange Cartridge.

Preparation 1:
2,4-dichloro-6-(trifluoromethyl)pyrimidine (P1)

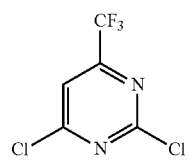 [SMILES: FC(F)(F)c1cc(Cl)nc(Cl)n1]

A mixture of 6-(Trifluoromethyl)uracil (3 g, 16.66 mmol), $SOCl_2$ (8 mL) and DMF (1 mL) was stirred at 80° C. for 4 hrs, then cooled to 0° C. Hexane and crushed ice were added to the resulting mixture, followed by careful addition of $NaHCO_3$ until $CO_2$ had stopped evolving. The organic layer was separated, dried and carefully concentrated at reduced pressure with bath temperature below 35° C., giving 2,4-dichloro-6-(trifluoromethyl)pyrimidine (P1, 3.2 g, y=88%) as pale yellow oil used in the next stage without additional purification.

$^1$H NMR (CHLOROFORM-d): δ ppm 7.67 (s, 1H)

Preparation 2: 2-chloro-4-(3-fluorophenoxy)-6-(trifluoromethyl)pyrimidine (P2)

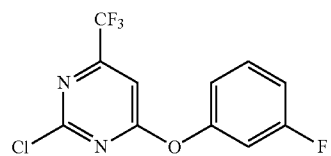 [SMILES: Fc1cccc(Oc2cc(C(F)(F)F)nc(Cl)n2)c1]

A mixture of 2,4-dichloro-6-(trifluoromethyl)pyrimidine (P1, 2 g, 9.2 mmol), 3-fluorophenol (0.75 mL, 8.2 mmol) and $K_2CO_3$ (1.66 g, 12 mmol) in DMSO (2 mL) was heated at 60° C. for 20 min. After cooling at RT, EtOAc and water were added and phases were separated. The organic phase was dried and evaporated; the crude material was purified by FC on silica gel (eluent: Cy to Cy/AcOEt 9/1) affording 2-chloro-4-(3-fluorophenoxy)-6-(trifluoromethyl)pyrimidine (P2, 2.26 g, y=94%) as pale yellow oil.

$^1$H NMR (CHLOROFORM-d): δppm 7.47 (td1H), 7.22 (s, 1H), 7.09 (td, 1H), 7.03-6.93 (m, 2H)

Preparation 3:
1-bromo-3-fluoro-5-(3-fluorophenoxy)benzene (P3)

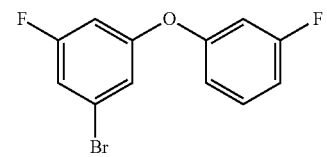 [SMILES: Fc1cccc(Oc2cc(F)cc(Br)c2)c1]

3-fluorophenol (0.178 mL, 1.97 mmol) and KOH (110 mg, 1.97 mmol) were stirred at 50° C. for 30 min before the addition of 1,3-dibromo-5-fluorobenzene (500 mg, 1.97 mmol) and Cu powder (125 mg, 1.97 mmol). The reaction mixture was heated to 150° for 2 hrs and then at 100° C. overnight. The crude product was purified by FC on silica gel (eluent: Cy), giving 1-bromo-3-fluoro-5-(3-fluorophenoxy)benzene (P3, 834 mg, y=22%) as oil.

$^1$H NMR (CHLOROFORM-d): δ ppm 7.41-7.33 (m, 1H), 7.05 (dt, 1H), 6.98 (s, 1H), 6.93 (td, 1H), 6.86 (dd, 1H), 6.79 (dt, 1H), 6.70 (dt, 1H)

Preparation 4: mixture of 1-bromo-2,3-difluoro-5-(3-fluorophenoxy)benzene and 5-bromo-1,2-difluoro-3-(3-fluorophenoxy)benzene (P4)

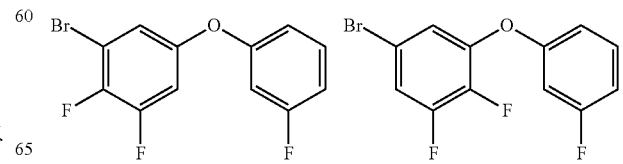

3-fluorophenol (0.117 mL, 1.29 mmol) and KOH (73 mg, 1.29 mmol) were stirred at 50° C. for 30 min before the addition of 1,5-dibromo-2,3-difluorobenzene (350 mg, 1.29 mmol) and Cu powder (82 mg, 1.29 mmol). The reaction mixture was heated to 150° C. for 2 hrs and then at 100° C. overnight. The crude material was purified by FC on silica gel (eluent: Cy) giving a mixture ~1:1 of 1-bromo-2,3-difluoro-5-(3-fluorophenoxy)benzene and 5-bromo-1,2-difluoro-3-(3-fluorophenoxy)benzene (P4, 68 mg, y=17%) as oil.

$^1$H NMR (CHLOROFORM-d): δ ppm 7.35 (q, 2 H), 7.16-7.23 (m, 1 H), 6.97-7.04 (m, 2 H), 6.87-6.95 (m, 2 H), 6.84-6.87 (m, 1 H), 6.79-6.84 (m, 2 H), 6.76 (ddt, 2 H).

Preparation 5:
1-bromo-2,5-difluoro-3-(3-fluorophenoxy)benzene (P5)

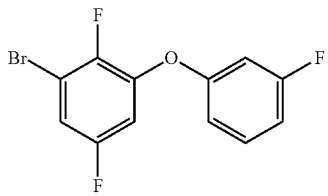 [SMILES: Fc1cccc(Oc2cc(F)cc(Br)c2F)c1]

3-fluorophenol (0.099 mL, 1.1 mmol) and KOH (62 mg, 1.1 mmol) were stirred at 50° C. for 30 min before the addition of 1,3-dibromo-2,5-difluorobenzene (300 mg, 1.1 mmol) and Cu powder (70 mg, 1.1 mmol).

The reaction mixture was heated to 100° C. overnight. The crude material was purified by FC on silica gel (eluent: Cy), giving 1-bromo-2,5-difluoro-3-(3-fluorophenoxy)benzene (P5, 61 mg, y=18%) as oil.

$^1$H NMR (METHANOL-$d_4$): δ ppm 7.49-7.38 (m, 1H), 7.33 (ddd, 1H), 7.02-6.93 (m, 2H), 6.90-6.82 (m, 2H)

Preparation 6: 1-bromo-2-fluoro-3-phenoxybenzene (P6)

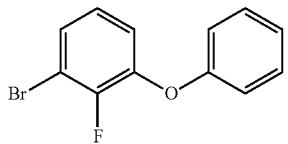 [SMILES: Fc1c(Br)cccc1Oc1ccccc1]

Method A:
TEA (2.66 mL, 19.1 mmol) was added to a mixture of 3-bromo-2-fluorophenol (730 mg, 3.82 mmol), phenyl boronic acid (932 mg, 7.64 mmol), Cu(OAc)$_2$ (1.04 mg, 5.73 mmol), molecular sieves and DCM (35 mL). The mixture was stirred at RT overnight and filtered through a pad of Celite washing with DCM. The filtrate was concentrated and the crude material was purified by FC on silica gel (eluent: Cy) to afford 1-bromo-2-fluoro-3-phenoxybenzene (P6, 40 mg, y=4%) as colourless oil.

Method B:
Step a
3-chloroperbenzoic acid (640 mg, 3 mmol) was dissolved in DCM (10 mL). To the solution iodobenzene (0.31 mL, 2.7 mmol) was added followed by slow addition of BF$_3$OEt$_2$ (0.850 mL, 6.8 mmol) at RT. The resulting yellow solution was stirred at RT for 30 min, cooled down to 0° C. and then phenyl boronic acid (370 mg, 3 mmol) was added in one portion. After 15 min at RT, the crude reaction mixture was charged on a silica cartridge (6 g) and eluted with DCM (60 mL) followed by DCM/MeOH 20/1 (120 mL). The latter solution was concentrated and Et$_2$O was added to precipitate the product which was further triturated with Et$_2$O. After decantation the white off solid was dried to afford diphenyliodonium tetrafluoroborate (1 g).

Step b
To a suspension of t-BuOK (43 mg, 0.37 mmol) in THF (1.5 mL) 3-bromo-2-fluorophenol (65 mg, 0.34 mmol) was added at 0° C. and the reaction mixture was left stirring for 15 min. Diphenyliodonium tetrafluoroborate (from step a, 145 mg, 0.4 mmol) was added in one portion and the reaction was stirred at 40° C. for 1 h. The reaction was quenched with H$_2$O and the product was extracted with DCM. Organic phase was evaporated and crude material purified by FC on silica gel (eluent: pentane) to afford 1-bromo-2-fluoro-3-phenoxybenzene (P6, 69 mg, y=76%)

$^1$H NMR (CHLOROFORM-d): δ ppm 7.42-7.31 (m, 3H), 7.19-7.12 (m, 1H), 7.06-6.94 (m, 4H)

Preparation 7:
1-bromo-2-fluoro-3-(3-fluorophenoxy)benzene (P7)

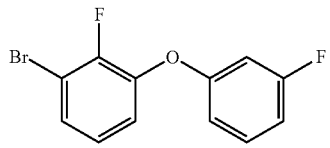 [SMILES: Fc1cccc(Oc2cccc(Br)c2F)c1]

Method A
3-fluorophenol (0.107 mL, 1.18 mmol) and KOH (66 mg, 1.18 mmol) were stirred at 50° C. for 30 min before the addition of 1,3-dibromo-2-fluorobenzene (300 mg, 1.18 mmol) and Cu powder (75 mg, 1.18 mmol). The reaction mixture was heated to 100° C. overnight. The crude material was purified by FC on silica gel (eluent: Cy), giving 1-bromo-2-fluoro-3-(3-fluorophenoxy)benzene (P7, 12 mg, y=3.5%) as oil.

Method B
Step a
3-chloroperbenzoic acid (640 mg, 3 mmol) was dissolved in DCM (10 mL). To the solution was added 3-fluoroiodobenzene (0.317 mL, 2.7 mmol) followed by slow addition of BF$_3$OEt$_2$ (0.850 mL, 6.8 mmol) at RT. The resulting yellow solution was stirred at RT for 30 min, then cooled at 0° C. and 3-fluoro-phenylboronic acid (420 mg, 3 mmol) was added in one portion. After 15 min at RT, the crude reaction mixture was charged on a silica cartridge (6 g) and eluted with DCM (60 mL) followed by DCM/MeOH 20/1

(120 mL). The latter solution was concentrated and Et₂O was added to triturate the product. After decantation the pale yellow solid was dried to afford bis(3-Fluoro-phenyl)iodonium tetrafluoroborate (820 mg).

Step b

To a suspension of t-BuOK (97 mg, 1.1 eq) in THF (3.5 mL), 3-bromo-2-fluorophenol (150 mg, 0.785 mmol) was added at 0° C. and the reaction was left stirring for 15 min at that temperature. Bis(3-fluoro-phenyl)iodonium tetrafluoroborate (from step a, 381 mg, 0.942 mmol) was added in one portion and the reaction was stirred at 40° C. for 1 h. The reaction was quenched with H₂O and the product was extracted with DCM. Organic phase was evaporated and the crude material was purified by FC on silica gel (eluent: pentane) affording 1-bromo-2-fluoro-3-(3-fluorophenoxy) benzene (P7, 160 mg, y=71%).

¹H NMR (DMSO-d₆): δ ppm 7.59 (td, 1H), 7.49-7.40 (m, 1H), 7.30-7.19 (m, 2H), 7.07-6.94 (m, 2H), 6.86 (dd, 1H)

Preparation 8: 6-benzyl-1-oxa-6-azaspiro[2.5]octane (P8)

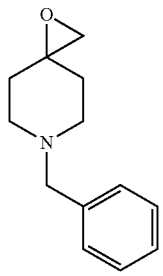 [SMILES: c1ccc(CN2CCC3(CC2)CO3)cc1]

To an ice-cooled mixture of NaH (60% dispersion in mineral oil, 2.75 g, 68.69 mmol) and trimethylsulfoxonium iodide (12.79 g, 58.12 mmol) DMSO (50 mL) was added keeping the mixture at 10° C. The mixture was stirred for 10 min at 10° C. then it was allowed to reach RT and left stirring at that temperature for 1 h. A solution of 1-benzylpiperidin-4-one (9.79 mL, 52.84 mmol) in DMSO (30 mL) was added via syringe. The mixture was stirred for 1.5 h at RT, diluted with Et₂O and quenched by the addition of saturated aqueous NH₄Cl. Phases were separated and aqueous one was back-extracted with Et₂O. Combined organics were dried, filtered and concentrated under reduced pressure affording 6-benzyl-1-oxa-6-azaspiro[2.5]octane (P8, 11.3 g, y=quant.) that was used as such in the next step.

MS (ES) (m/z): 204.05 [M+H]⁺.

Preparation 9: 1-benzyl-4-[(dimethylamino)methyl]piperidin-4-ol (P9)

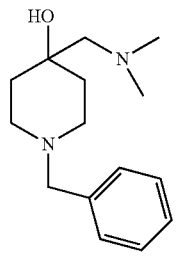 [SMILES: CN(C)CC1(O)CCN(Cc2ccccc2)CC1]

To a stirred solution of 6-benzyl-1-oxa-6-azaspiro[2.5] octane (P8, 0.5 g, 2.46 mmol) in MeOH/water (2/4 mL), at 0° C., dimethylamine 40% water solution (0.62 mL, 4.92 mmol) was added dropwise. Once the addition was complete, the ice-bath was removed and the resulting reaction mixture was stirred at RT for 2 hrs. Solvent was removed under reduced pressure and the residue was partitioned between DCM and NaOH 1M aq. Organic phase was dried and concentrated under reduced pressure affording 1-benzyl-4-[(dimethylamino)methyl]piperidin-4-ol (P9, 612 mg, y=quant) used as such in next step.

MS (ES) (m/z): 249.12 [M+H]⁺.

Example 1

4-[(dimethylamino)methyl]-1-[4-(3-fluorophenoxy)-6(trifluoromethyl)pyrimidin-2-yl]piperidin-4-ol (E1)

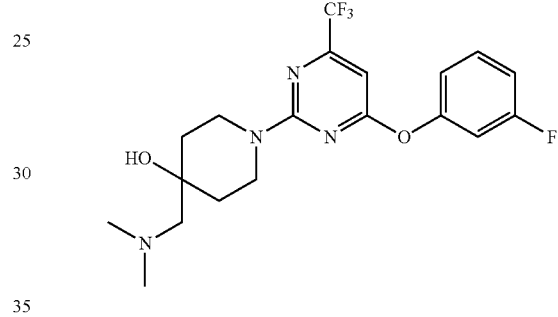

Step a

To a solution of 1-benzyl-4-[(dimethylamino)methyl]piperidin-4-ol (P9, 200 mg, 0.8 mmol) in MeOH (5 mL) ammonium formate (305 mg, 4.83 mmol) and 10% Pd/C (12 mg) were added at RT then the mixture was stirred under reflux for 1 h. The mixture was cooled down to RT and filtered through a pad of celite washing with MeOH. Solvent was eliminated under reduced pressure affording 4-[(dimethylamino)methyl]piperidin-4-ol (259 mg) as formate salt. Used as such in next step Step b To a solution of 4-[(dimethylamino)methyl]piperidin-4-ol (from step a, 75 mg, 0.22 mmol) in DMSO (2 mL) 2-chloro-4-(3-fluorophenoxy)-6-(trifluoromethyl)pyrimidine (P2, 66 mg, 0.22 mmol) and K₂CO₃ (92 mg, 0.66 mmol) were added at RT then the mixture was shaken at 50° C. for 1 h. The mixture was cooled down, diluted with AcOEt and washed with water. Organic phase was dried and concentrated; the crude material was purified by FC on silica gel (eluent: DCM to DCM/MeOH 8:2) then further purified by FC on NH column (eluent: Cy to Cy/AcOEt 7:3) affording 4-[(dimethylamino)methyl]-1-[4-(3-fluorophenoxy)-6(trifluoromethyl)pyrimidin-2-yl]piperidin-4-ol (E1, 28 mg).

MS (ES) (m/z): 415.05 [M+H]⁺.

¹H NMR (CHLOROFORM-d): δ ppm 7.45-7.35 (m, 1H), 7.07-6.91 (m, 3H), 6.33 (s, 1H), 4.52 (br. s., 1H), 4.23 (br. s., 1H), 3.32 (br. s., 2H), 2.43 (s, 6H), 2.34 (br. s., 2H), 1.45 (d, 4H)

Preparation 10: 1-benzyl-4-(pyrrolidin-1-ylmethyl) piperidin-4-ol (P10)

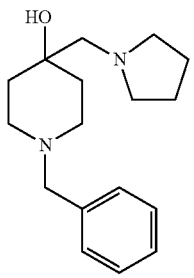 [SMILES: OC1(CN2CCCC2)CCN(Cc2ccccc2)CC1]

To a stirred solution of 6-benzyl-1-oxa-6-azaspiro[2.5]octane (P8, 0.2 g, 0.98 mmol) in MeOH/water (1/2 mL), pyrrolidine (0.164 mL, 1.96 mmol) was added dropwise. Once the addition was complete the resulting reaction mixture was shaken at RT for 2 hrs. Solvent was removed under reduced pressure and the residue was partitioned between DCM and NaOH 1M aq. Organic phase was dried and concentrated under reduced pressure affording 1-benzyl-4-(pyrrolidin-1-ylmethyl)piperidin-4-ol (P10, 280 mg, y=quant.) used as such in next step.

MS (ES) (m/z): 275.20 [M+H]$^+$

Example 2

1-[4-(3-fluorophenoxy)-6-(trifluoromethyl)pyrimidin-2-yl]-4-(pyrrolidin-1-ylmethyl)piperidin-4-ol (E2)

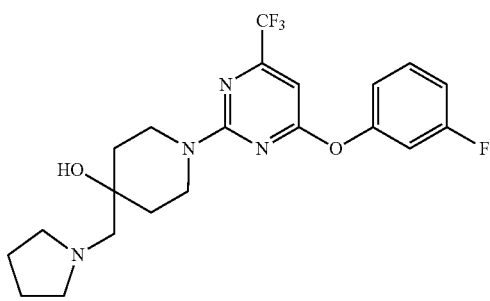 [SMILES: OC1(CN2CCCC2)CCN(c2nc(Oc3cccc(F)c3)cc(C(F)(F)F)n2)CC1]

Step a:
To a solution of 1-benzyl-4-(pyrrolidin-1-ylmethyl)piperidin-4-ol (P10, 280 mg, 1.02 mmol) in MeOH (5 mL) ammonium formate (386 mg, 6.12 mmol) and 10% Pd/C (30 mg) were added at RT, then the mixture was stirred under reflux for 1 h. The mixture was cooled down to RT and filtered through a pad of celite washing with MeOH. Solvent was eliminated under reduced pressure affording 4-(pyrrolidin-1-ylmethyl)piperidin-4-ol (280 mg).
Step b:
To a solution of 1-benzyl-4-(pyrrolidin-1-ylmethyl)piperidin-4-ol (from step a, 80 mg, 0.43 mmol) in DMSO (2 mL) 2-chloro-4-(3-fluorophenoxy)-6-(trifluoromethyl)pyrimidine (P2, 102 mg, 0.35 mmol) and K$_2$CO$_3$ (178 mg, 1.29 mmol) were added at RT then the mixture was shaken at 60° C. for 2 hrs. The mixture was cooled down, diluted with DCM and washed with water. Organic phase was dried and concentrated and the crude material was purified by FC on NH column (eluent: Cy to Cy/AcOEt 1:1) affording 1-[4-(3-fluorophenoxy)-6-(trifluoromethyl)pyrimidin-2-yl]-4-(pyrrolidin-1-ylmethyl)piperidin-4-ol (E2, 42 mg, y=22%).
MS (ES) (m/z): 441.19 [M+H]$^+$.
$^1$H NMR (CHLOROFORM-d): δ ppm 7.43-7.34 (m, 1H), 7.04-6.88 (m, 3H), 6.37-6.29 (m, 1H), 4.54 (br. s., 1H), 4.16 (br. s., 1H), 3.32 (br. s., 2H), 2.74 (br. s., 3H), 2.55 (br. s., 2H), 1.83 (br. s., 5H), 1.45 (br. s., 4H)

Preparation 11: 1-benzyl-4-[(cyclopropylamino)methyl]piperidin-4-ol (P11)

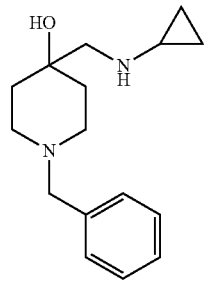 [SMILES: OC1(CNC2CC2)CCN(Cc2ccccc2)CC1]

To a stirred solution of 6-benzyl-1-oxa-6-azaspiro[2.5]octane (P8, 0.2 g, 0.98 mmol) in MeOH/water (1/2 mL), at 0° C., cyclopropylamine (0.136 mL, 1.97 mmol) was added dropwise. Once the addition was complete, the ice-bath was removed and the resulting reaction mixture was stirred at RT for 2 hrs. Solvent was removed under reduced pressure and the residue was partitioned between DCM and NaOH 1M aq. Organic phase was dried and concentrated under reduced pressure affording 1-benzyl-4-[(cyclopropylamino)methyl]piperidin-4-ol (P11, 260 mg, y=quant.) used as such in next step.

MS (ES) (m/z): 261.13 [M+H]$^+$.

Preparation 12: tert-butyl N-[(1-benzyl-4-hydroxypiperidin-4-yl)methyl]-N-cyclopropylcarbamate (P12)

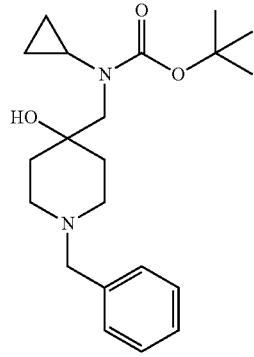 [SMILES: CC(C)(C)OC(=O)N(CC1(O)CCN(Cc2ccccc2)CC1)C1CC1]

To a solution of 1-benzyl-4-[(cyclopropylamino)methyl]piperidin-4-ol (P8, 260 mg, 1 mmol) in DCM 5 mL, Boc$_2$O (218 mg, 1 mmol) was added and the mixture was stirred at RT for 2 hrs, then solvent was eliminated under reduced pressure affording tert-butyl N-[(1-benzyl-4-hydroxypiperidin-4-yl)methyl]-N-cyclopropylcarbamate (P12, 391 mg, crude material) used as such.

MS (ES) (m/z): 361.1 [M+H]$^+$.

Preparation 13: tert-butyl N-cyclopropyl-N-({1-[4-(3-fluorophenoxy)-6-(trifluoromethyl)pyrimidin-2-yl]-4-hydroxypiperidin-4-yl}methyl)carbamate (P13)

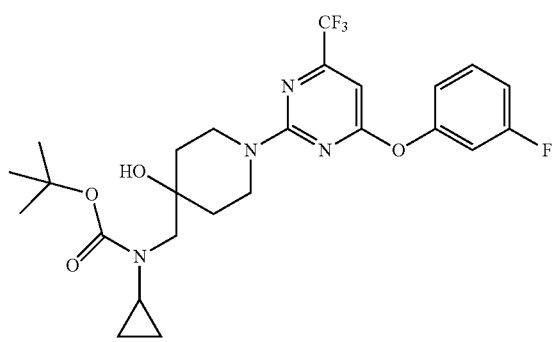 [SMILES: CC(C)(C)OC(=O)N(CC1(O)CCN(c2nc(Oc3cccc(F)c3)cc(C(F)(F)F)n2)CC1)C1CC1]

Step a:

To a solution of tert-butyl N-[(1-benzyl-4-hydroxypiperidin-4-yl)methyl]-N-cyclopropylcarbamate (P12, 391 mg, 1.08 mmol) in MeOH (5 mL) ammonium formate (408 mg, 6.48 mmol) and 10% Pd/C (30 mg) were added at RT then the mixture was stirred under reflux for 3 hrs. The mixture was then cooled down to RT and filtered through a pad of celite washing with MeOH. Solvent was eliminated under reduced pressure affording tert-butyl N-cyclopropyl-N-[(4-hydroxypiperidin-4-yl)methyl]carbamate (425 mg)

Step b:

2-chloro-4-(3-fluorophenoxy)-6-(trifluoromethyl)pyrimidine (P2, 65 mg, 0.222 mmol), tert-butyl N-cyclopropyl-N-[(4-hydroxypiperidin-4-yl)methyl]carbamate (from step a, 100 mg, 0.222 mmol) and $K_2CO_3$ (40 mg, 0.289 mmol) were mixed in dry DMSO (1 mL) and the mixture was shaken at 60° C. for 1 hr. Then the mixture was diluted with EtOAC and water. The organic phase was washed several times with brine, dried, filtered and evaporated. Crude material was purified by FC on NH column (eluent: Cy to Cy 90/EtOAc10). affording tert-butyl N-cyclopropyl-N-({1-[4-(3-fluorophenoxy)-6-(trifluoromethyl)pyrimidin-2-yl]-4-hydroxypiperidin-4-yl}methyl)carbamate (P13, 50 mg).

MS (ES) (m/z): 527.19 $[M+H]^+$.

Example 3

4-[(cyclopropylamino)methyl]-1-[4-(3-fluorophenoxy)-6-(trifluoromethyl)pyrimidin-2-yl]piperidin-4-ol (E3)

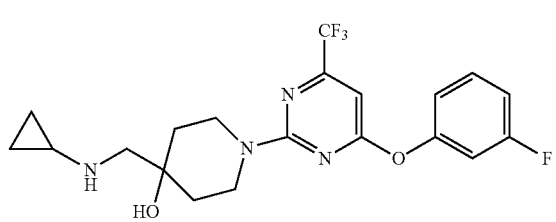 [SMILES: OC1(CNC2CC2)CCN(c2nc(Oc3cccc(F)c3)cc(C(F)(F)F)n2)CC1]

TFA (0.5 mL) was added to a solution of tert-butyl N-cyclopropyl-N-({1-[4-(3-fluorophenoxy)-6-(trifluoromethyl)pyrimidin-2-yl]-4-hydroxypiperidin-4-yl}methyl)carbamate (P13, 50 mg, 0.095 mmol) in 3 mL of DCM. The mixture was stirred at RT for 1 h, and then the solvent was removed under reduced pressure. The residue was charged on SCX cartridge washing with MeOH and eluting with 1M $NH_3$ in MeOH to afford 4-[(cyclopropylamino)methyl]-1-[4-(3-fluorophenoxy)-6-(trifluoromethyl)pyrimidin-2-yl]piperidin-4-ol (E3, 40 mg, y=98%).

MS (ES) (m/z): 427.18 $[M+H]^+$
$^1$H NMR (CHLOROFORM-d): δ ppm 7.46-7.33 (m, 1H), 7.07-6.85 (m, 3H), 6.34 (s, 1H), 4.47 (br. s., 1H), 4.22 (br. s., 1H), 3.40-3.17 (m, 2H), 2.70 (s, 2H), 2.31-2.20 (m, 1H), 1.64-1.50 (m, 2H), 1.44 (br. s., 2H), 0.57-0.47 (m, 2H), 0.40 (br. s., 2H)

Example

4-{[cyclopropyl(methyl)amino]methyl}-1-[4-(3-fluorophenoxy)-6-(trifluoromethyl)pyrimidin-2-yl]piperidin-4-ol (E4)

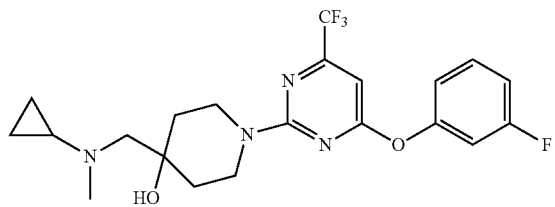 [SMILES: CN(CC1(O)CCN(c2nc(Oc3cccc(F)c3)cc(C(F)(F)F)n2)CC1)C1CC1]

To a solution of 4-[(cyclopropylamino)methyl]-1-[4-(3-fluorophenoxy)-6-(trifluoromethyl)pyrimidin-2-yl]piperidin-4-ol (E3, 20 mg, 0.047 mmol) in DCM (2 mL), formaldehyde (0.035 mL, 0.47 mmol) was added and the mixture was stirred at RT for 15 min. $NaBH(OAc)_3$ (38 mg, 0.180 mmol) was added and the mixture was stirred at RT overnight. Water was added and phases were separated. The organic phase was washed with brine, dried, filtered and evaporated to afford 4-{[cyclopropyl(methyl)amino]methyl}-1-[4-(3-fluorophenoxy)-6-(trifuoromethyl)pyrimidin-2-yl]piperidin-4-ol (E4, 15 mg, y=72%).

MS (ES) (m/z): 441.21 $[M+H]^+$
$^1$H NMR (CHLOROFORM-d): δ ppm 7.44-7.35 (m, 1H), 7.07-6.90 (m, 3H), 6.33 (s, 1H), 4.47 (br. s., 1H), 4.21 (br. s., 1H), 3.29 (br. s., 2H), 3.10 (br. s., 1H), 2.58 (s, 2H), 2.48 (s, 3H), 1.96 (br. s., 1H), 1.56 (br. s., 2H), 1.44 (br. s., 2H), 0.59-0.39 (m, 4H)

Preparation 14: 1-benzyl-4-[(methylamino)methyl]piperidin-4-ol (P14)

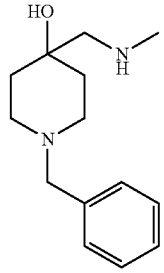 [SMILES: CNCC1(O)CCN(Cc2ccccc2)CC1]

To a stirred solution of 6-benzyl-1-oxa-6-azaspiro[2.5]octane (P8, 0.2 g, 0.98 mmol) in MeOH/water (1/2 mL), at 0° C., methylamine 33% ethanol solution (0.244 mL, 1.97 mmol) was added dropwise. Once the addition was complete, the ice-bath was removed and the resulting reaction mixture was stirred at RT for 2 hrs. Solvent was removed under reduced pressure and the residue was partitioned between DCM and NaOH 1M aq. Organic phase was dried and concentrated under reduced pressure affording 1-benzyl-4-[(methylamino)methyl]piperidin-4-ol (P14, 222 mg, y=97%) used as such in next step.

MS (ES) (m/z): 235.09 [M+H]+.

Preparation 15: tert-butyl N-[(1-benzyl-4-hydroxypiperidin-4-yl)methyl]-N-methylcarbamate (P15)

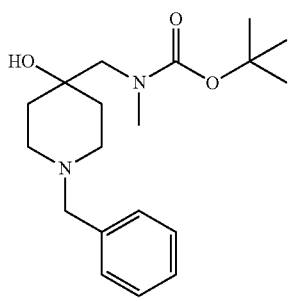 [SMILES: CN(CC1(O)CCN(Cc2ccccc2)CC1)C(=O)OC(C)(C)C]

1-benzyl-4-[(methylamino)methyl]piperidin-4-ol (P14, 220 mg, 0.939 mmol) was dissolved in DCM (2 mL), TEA (0.2 mL, 1.41 mmol) was added followed by a solution of Boc2O (247 mg, 1.13 mmol) in DCM (2 mL). The resulting solution was stirred at RT for 2 hrs. NH4Cl was added, the organic phase was separated, dried and concentrated. The crude material was purified by FC on silica gel (eluent: EtOAc to EtOAc/MeOH 90/10) affording tert-butyl N-[(1-benzyl-4-hydroxypiperidin-4-yl)methyl]-N-methylcarbamate (P15, 240 mg, y=76%) as colourless oil.

MS (ES) (m/z): 335.22 [M+H]+.

Preparation 16: tert-butyl N-({1-[4-(3-fluorophenoxy)-6-(trifluoromethyl)pyrimidin-2-yl]-4-hydroxypiperidin-4-yl}methyl)-N-methylcarbamate (P16)

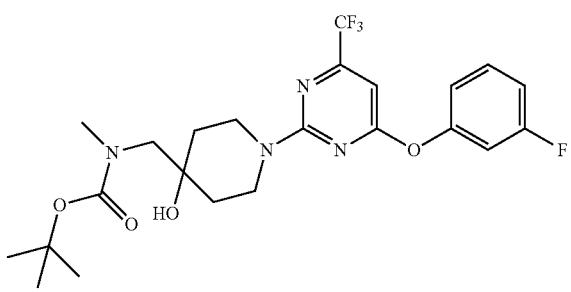 [SMILES: CN(CC1(O)CCN(c2nc(Oc3cccc(F)c3)cc(C(F)(F)F)n2)CC1)C(=O)OC(C)(C)C]

Step a:

To a solution of tert-butyl N-[(1-benzyl-4-hydroxypiperidin-4-yl)methyl]-N-methylcarbamate (P15, 240 mg, 0.718 mmol) in MeOH (6 mL) ammonium formate (272 mg, 4.31 mmol) and 10% Pd/C (72 mg) were added at RT then the mixture was stirred under reflux for 1 h. The mixture was then cooled down to RT and filtered through a pad of celite washing with MeOH. Solvent was eliminated under reduced pressure affording tert-butyl N-[(4-hydroxypiperidin-4-yl)methyl]-N-methylcarbamate (150 mg) as colourless oil.

Step b:

2-chloro-4-(3-fluorophenoxy)-6-(trifluoromethyl)pyrimidine (P2, 60 mg, 0.205 mmol), tert-butyl N-[(4-hydroxypiperidin-4-yl)methyl]-N-methylcarbamate (from step a, 50 mg, 0.205 mmol) and K2CO3 (37 mg, 0.267 mmol) were mixed in dry DMSO (1 mL) and the mixture was shaken at 60° C. for 1 hr. The mixture was diluted with EtOAC and water. The organic phase was washed several times with brine, dried, filtered and evaporated; crude material was purified by FC on NH column (eluent: Cy to Cy85/EtOAc15) affording tert-butyl N-({1-[4-(3-fluorophenoxy)-6-(trifluoromethyl)pyrimidin-2-yl]-4-hydroxypiperidin-4-yl}methyl)-N-methylcarbamate (P16, 40 mg).

MS (ES) (m/z): 501.18 [M+H]+.

Example 5

1-[4-(3-fluorophenoxy)-6-(trifluoromethyl)pyrimidin-2-yl]-4-[(methylamino)methyl]piperidin-4-ol (E5)

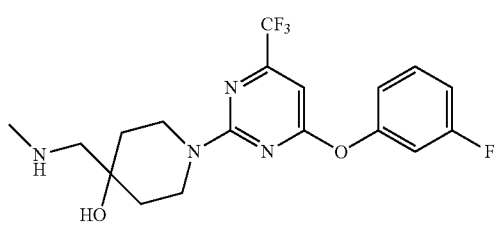 [SMILES: CNCC1(O)CCN(c2nc(Oc3cccc(F)c3)cc(C(F)(F)F)n2)CC1]

TFA (0.5 mL) was added to a solution of tert-butyl N-({1-[4-(3-fluorophenoxy)-6-(trifluoromethyl)pyrimidin-2-yl]-4-hydroxypiperidin-4-yl}methyl)-N-methylcarbamate (P16, 40 mg, 0.080 mmol) in DCM (3 mL). The mixture was stirred at RT for 1 h, and then the solvent was removed under reduced pressure. The residue was charged on SCX cartridge washing with MeOH and eluting with 1M NH3 in MeOH to afford 1-[4-(3-fluorophenoxy)-6-(trifluoromethyl)pyrimidin-2-yl]-4-[(methylamino)methyl]piperidin-4-ol (E5, 30 mg, y=94%).

MS (ES) (m/z): 401.15 [M+H]+

1H NMR (CHLOROFORM-d): δ ppm 7.43-7.33 (m, 1H), 7.06-6.88 (m, 3H), 6.37-6.30 (m, 1H), 4.55 (br. s., 1H), 4.19 (br. s., 1H), 3.30 (br.s., 2H), 2.56 (s, 2H), 2.53 (s, 3H), 1.59 (br. s., 2H), 1.46 (br. s., 2H)

Preparation 17: 1-benzyl-4-[(3,3-difluoropyrrolidin-1-yl)methyl]piperidin-4-ol (P17)

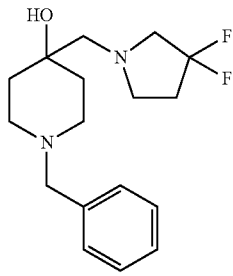 [SMILES: OC1(CN2CCC(F)(F)C2)CCN(Cc2ccccc2)CC1]

To a stirred solution of 6-benzyl-1-oxa-6-azaspiro[2.5]octane (P8, 0.2 g, 0.98 mmol) in MeOH (1 mL), a solution of 3,3-Difluoropyrrolidine hydrochloride (282 mg, 1.96 mmol) and TEA (0.272 mL, 1.96 mmol) in $H_2O$ (2 mL) was added dropwise. Once the addition was complete the resulting reaction mixture was shaken at RT overnight. Solvent was removed under reduced pressure and the residue was partitioned between DCM and NaOH 1M aq. Organic phase was dried and concentrated under reduced pressure affording 1-benzyl-4-[(3,3-difluoropyrrolidin-1-yl)methyl]piperidin-4-ol (P17, 305 mg, y=quant.) used as such in next step.
MS (ES) (m/z): 311.16 $[M+H]^+$.

Example 6

4-[(3,3-difluoropyrrolidin-1-yl)methyl]-1-[4-(3-fluorophenoxy)-6-(trifluoromethyl)pyrimidin-2-yl]piperidin-4-ol (E6)

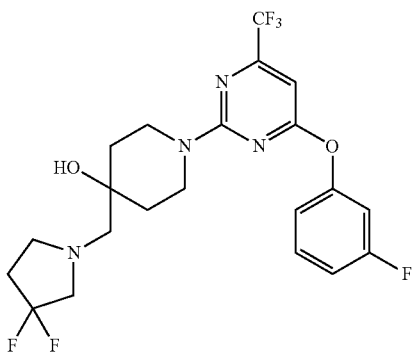 [SMILES: OC1(CN2CCC(F)(F)C2)CCN(c2nc(Oc3cccc(F)c3)cc(C(F)(F)F)n2)CC1]

Step a:
To a solution of 1-benzyl-4-[(3,3-difluoropyrrolidin-1-yl)methyl]piperidin-4-ol (P17, 305 mg, 0.98 mmol) in MeOH (8 mL) ammonium formate (370 mg, 5.88 mmol) and 10% Pd/C (30 mg) were added at RT then the mixture was stirred under reflux for 3 hrs. The mixture was then cooled down to RT and filtered through a pad of celite washing with MeOH. Solvent was eliminated under reduced pressure affording 4-[(3,3-difluoropyrrolidin-1-yl)methyl]piperidin-4-ol (320 mg).
Step b:
A mixture of 4-[(3,3-difluoropyrrolidin-1-yl)methyl]piperidin-4-ol (from step a, 80 mg, 0.195 mmol), 2-chloro-4-(3-fluorophenoxy)-6-(trifluoromethyl)pyrimidine (P2, 44 mg, 0.195 mmol) and $K_2CO_3$ (35 mg, 0.253 mmol) in DMSO (0.5 mL) was heated at 100° C. for 1 h. After cooling to RT, EtOAc and water were added and phases were separated. The organic phase was dried and evaporated, the residue was purified by FC on NH column (eluent: cHex to cHex 80/EtOAc 20) affording 4-[(3,3-difluoropyrrolidin-1-yl)methyl]-1-[4-(3-fluorophenoxy)-6-(trifluoromethyl)pyrimidin-2-yl]piperidin-4-ol (E6, 27 mg,) as colourless oil.
MS (ES) (m/z): 477.01 $[M+H]^+$.
$^1$H NMR (CHLOROFORM-d): δ ppm 7.44-7.34 (m, 1H), 7.05-6.89 (m, 3H), 6.35 (s, 1H), 4.52 (br. s., 1H), 4.24 (br. s., 1H), 3.31 (br. s., 2H), 3.10 (t, 2H), 2.96 (t, 2H), 2.82 (br. s., 1H), 2.52 (s, 2H), 2.30 (tt, 2H), 1.60 (d, 2H), 1.46 (br. s., 2H)

Preparation 18: tert-butyl 4-[(1-benzyl-4-hydroxypiperidin-4-yl)methyl]-1,4-diazepane-1-carboxylate (P18)

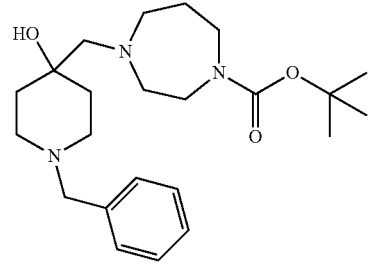 [SMILES: CC(C)(C)OC(=O)N1CCCN(CC2(O)CCN(Cc3ccccc3)CC2)CC1]

To a stirred mixture of 6-benzyl-1-oxa-6-azaspiro[2.5]octane (P8, 300 mg, 1.48 mmol) in MeOH (1.5 mL) and water (2 mL), a solution of tert-butyl 1,4-diazepane-1-carboxylate (0.58 mL, 2.95 mmol) in MeOH (0.5 mL) was added and the resulting reaction mixture was shaken overnight at RT. The mixture was concentrated under reduced pressure, the residue was taken up with DCM and saturated sodium bicarbonate, the organic phase was washed with water, dried and concentrated under vacuum. The residue was purified by FC on silica gel (eluent: DCM to DCM/MeOH 97/3) to give tert-butyl 4-[(1-benzyl-4-hydroxypiperidin-4-yl)methyl]-1,4-diazepane-1-carboxylate (P18, 367 mg, y=66%) as colourless oil.
MS (ES) (m/z): 404.3 $[M+H]^+$.

Preparation 19: tert-butyl 4-[(4-hydroxypiperidin-4-yl)methyl]-1,4-diazepane-1-carboxylate (P19)

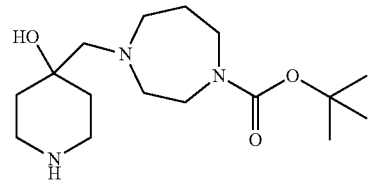 [SMILES: CC(C)(C)OC(=O)N1CCCN(CC2(O)CCNCC2)CC1]

To a solution of tert-butyl 4-[(1-benzyl-4-hydroxypiperidin-4-yl)methyl]-1,4-diazepane-1-carboxylate (P18, 367 mg, 0.91 mmol) in MeOH (20 mL), ammonium formate (344 mg, 5.46 mmol) and 10% Pd/C (114 mg) were added at RT then the mixture was stirred under reflux. After 2 hrs the reaction mixture was filtered through a pad of celite and the solvent removed under vacuum. The residue was dissolved in DCM, the organic solution washed with saturated NaHCO$_3$, dried and concentrated under reduced pressure to give tert-butyl 4-[(4-hydroxypiperidin-4-yl)methyl]-1,4-diazepane-1-carboxylate (P19, 139 mg, y=49%) as colourless oil.

MS (ES) (m/z): 314.2 [M+H]$^+$.

Preparation 19A: tert-butyl 4-({1-[4-(3-fluorophenoxy)-6-(trifluoromethyl)pyrimidin-2-yl]-4-hydroxypiperidin-4-yl}methyl)-1,4-diazepane-1-carboxylate (P19A)

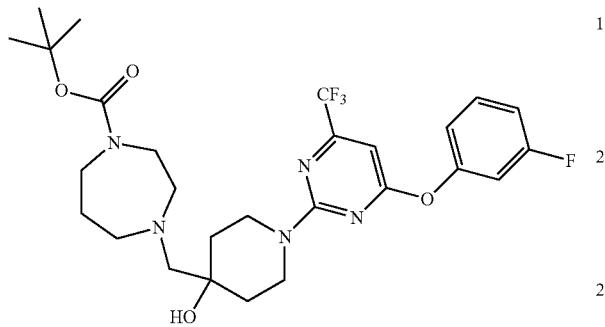

In a closed vessel a mixture of tert-butyl 4-[(4-hydroxypiperidin-4-yl)methyl]-1,4-diazepane-1-carboxylate (P19, 64 mg, 0.21 mmol), 2-chloro-4-(3-fluorophenoxy)-6-(trifluoromethyl)pyrimidine (P2, 60 mg. 0.21 mmol) and K$_2$CO$_3$ (38 mg, 0.27 mmol) in DMSO (0.8 mL) was heated at 90° C. and shaken 2 hrs at this temperature. After cooling at RT, EA and water were added, the organic phase was washed with water, dried and evaporated. Crude product was purified by FC on NH column (eluent: Cy to Cy/EA 80/20) affording tert-butyl 4-({1-[4-(3-fluorophenoxy)-6-(trifluoromethyl)pyrimidin-2-yl]-4-hydroxypiperidin-4-yl}methyl)-1,4-diazepane-1-carboxylate (P19A, 73 mg, y=61%).

MS (ES) (m/z): 570.3 [M+H]$^+$.

Example 7

4-(1,4-diazepan-1-ylmethyl)-1-[4-(3-fluorophenoxy)-6-(trifluoromethyl)pyrimidin-2-yl]piperidin-4-ol hydrochloride (E7)

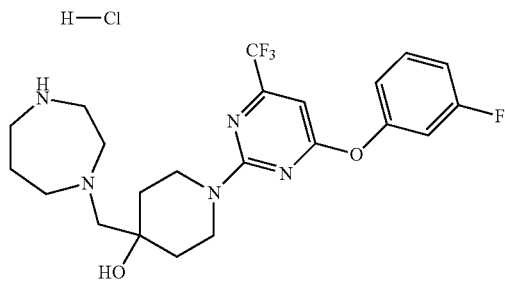 [SMILES: Cl ; OC1(CN2CCCNCC2)CCN(c2nc(Oc3cccc(F)c3)cc(C(F)(F)F)n2)CC1]

Step a

To a solution of tert-butyl 4-({1-[4-(3-fluorophenoxy)-6-(trifluoromethyl)pyrimidin-2-yl]-4-hydroxypiperidin-4-yl}methyl)-1,4-diazepane-1-carboxylate (P19A, 73 mg, 0.13 mmol) in DCM (0.6 mL), at RT, TFA (0.29 mL) was added. After 2 hrs the reaction mixture was concentrated under vacuum. The residue was taken up with DCM and concentrated sodium bicarbonate, the organic phase was dried and the solvent removed under vacuum affording 4-(1,4-diazepan-1-ylmethyl)-1-[4-(3-fluorophenoxy)-6-(trifluoromethyl)pyrimidin-2-yl]piperidin-4-ol (35 mg).

Step b 4-(1,4-diazepan-1-ylmethyl)-1-[4-(3-fluorophenoxy)-6-(trifluoromethyl)pyrimidin-2-yl]piperidin-4-ol (from step a, 35 mg, 0.075 mmol) was dissolved in DCM (0.2 mL) and 2N HCl in ether (0.037 mL) was added. The mixture was concentrated under reduced pressure, the residue was triturated with ether and dried under vacuum to give 4-(1,4-diazepan-1-ylmethyl)-1-[4-(3-fluorophenoxy)-6-(trifluoromethyl)pyrimidin-2-yl]piperidin-4-ol hydrochloride (E8, 11 mg, y=17%).

MS (ES) (m/z): 470.25 [M+H]$^+$ $^1$H NMR (DMSO-d$_6$): δ ppm 8.84 (br. s., 2H), 7.58-7.45 (m, 1H), 7.26 (dt, 1H), 7.22-7.08 (m, 2H), 6.62 (s, 1H), 4.30 (br. s., 2H), 3.87 (br. s., 1H), 3.09 (s, 2H), 3.14 (s, 3H), 2.95 (br. s., 2H), 2.78 (br. s., 2H), 2.47 (br. s., 2H), 1.84 (br. s., 2H), 1.42 (br. s., 4H)

Preparation 20: 1-benzyl-4-[(2,5-dimethylpyrrolidin-1-yl)methyl]piperidin-4-ol (P20)

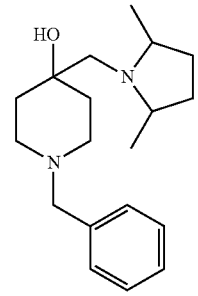 [SMILES: CC1CCC(C)N1CC1(O)CCN(Cc2ccccc2)CC1]

To a stirred solution of 6-benzyl-1-oxa-6-azaspiro[2.5] octane (P8, 0.2 g, 0.98 mmol) in MeOH/water (2/4 mL) 2,5-dimethylpyrrolidine (0.241 mL, 1.97 mmol) was added dropwise. Once the addition was complete the reaction mixture was shaken at RT for 2 hrs, then at 45° C. overnight. Solvent was removed under reduced pressure and the residue was partitioned between DCM and NaOH 1M aq. Organic phase was dried and concentrated under reduced pressure affording 1-benzyl-4-[(2,5-dimethylpyrrolidin-1-yl)methyl]piperidin-4-ol (P20, 263 mg, y=88%) used as such in next step.

MS (ES) (m/z): 303.1 [M+H]$^+$.

Preparation 21: 4-[(2,5-dimethylpyrrolidin-1-yl)methyl]piperidin-4-ol (P21)

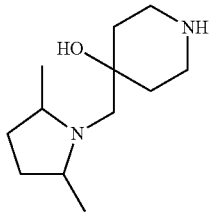

To a solution of 1-benzyl-4-[(2,5-dimethylpyrrolidin-1-yl)methyl]piperidin-4-ol (P20, 263 mg, 0.87 mmol) in MeOH (5 mL) ammonium formate (0.329 g, 5.21 mmol) and 10% Pd/C (20 mg) were added at RT then the mixture was stirred under reflux for 1.5 h. The mixture was then cooled down to RT and filtered through a pad of celite washing with MeOH. Solvent was eliminated under reduced pressure affording 4-[(2,5-dimethylpyrrolidin-1-yl)methyl]piperidin-4-ol (P21, 340 mg, crude material)

MS (ES) (m/z): 213.2 [M+H]$^+$.

Example 8

4-[(2,5-dimethylpyrrolidin-1-yl)methyl]-1-[4-(3-fluorophenoxy)-6-(trifluoromethyl)pyrimidin-2-yl]piperidin-4-ol (E8)

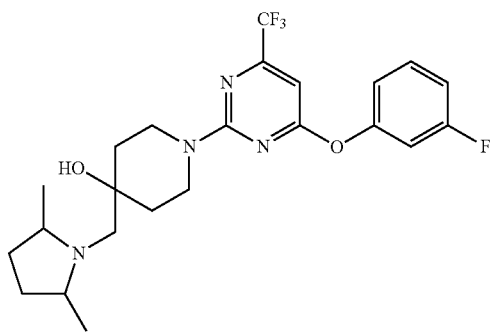 [SMILES: CC1CCC(C)N1CC1(O)CCN(c2nc(Oc3cccc(F)c3)cc(C(F)(F)F)n2)CC1]

To a solution of 4-[(2,5-dimethylpyrrolidin-1-yl)methyl]piperidin-4-ol (P21, 50 mg, 0.24 mmol) in DMSO (2 mL) 2-chloro-4-(3-fluorophenoxy)-6-(trifluoromethyl)pyrimidine (69 mg, 0.24 mmol) and K$_2$CO$_3$ (66 mg, 0.48 mmol) were added at RT then the mixture was shaken at 50° C. for 2 hrs. The mixture was cooled down to RT, diluted with DCM and washed with water. Organic phase was dried and concentrated and the crude material was purified by FC on Silica gel (eluent: Cy to Cy/AcOEt 1/1) then charged on a SCX cartridge washing with MeOH and eluting with NH$_3$ 1M in MeOH to give 4-[(2,5-dimethylpyrrolidin-1-yl)methyl]-1-[4-(3-fluorophenoxy)-6-(trifluoromethyl)pyrimidin-2-yl]piperidin-4-ol (E8, 20 mg, y=18%)

MS (ES) (m/z): 469.07 [M+H]$^+$ $^1$H NMR (CHLOROFORM-d): δ ppm 7.45-7.33 (m, 1H), 7.05-6.87 (m, 3H), 6.31 (s, 1H), 4.60 (br. s., 1H), 4.17 (br. s., 1H), 3.29 (br. s., 2H), 2.71 (d, 2H), 2.51 (s, 2H), 1.89 (br. s., 2H), 1.45-1.28 (m, 6H), 1.12 (d, 6H)

Preparation 22: 1-benzyl-4-[(tert-butylamino)methyl]piperidin-4-ol (P22)

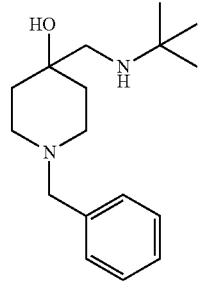 [SMILES: CC(C)(C)NCC1(O)CCN(Cc2ccccc2)CC1]

To a stirred solution of 6-benzyl-1-oxa-6-azaspiro[2.5]octane (P8, 0.2 g, 0.98 mmol) in MeOH/water (1/2 mL), at 0° C., tert-butylamine (0.2 mL, 1.97 mmol) was added dropwise. Once the addition was complete, the ice-bath was removed and the resulting reaction mixture was stirred at 45° C. overnight. Solvent was removed under reduced pressure and the residue was partitioned between DCM and NaOH 1M aq. Organic phase was dried and concentrated under reduced pressure affording 1-benzyl-4-[(tert-butylamino)methyl]piperidin-4-ol (P22, 270 mg, y=quant) used as such in next step.

MS (ES) (m/z): 277.1 [M+H]$^+$.

Preparation 23: 4-[(tert-butylamino)methyl]piperidin-4-ol (P23)

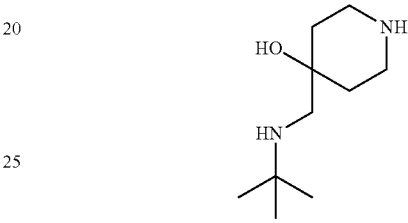

To a solution of 1-benzyl-4-[(tert-butylamino)methyl]piperidin-4-ol (P22, 270 mg, 0.98 mmol) in MeOH (8 mL) ammonium formate (370 mg, 5.88 mmol) and 10% Pd/C (90 mg) were added at RT then the mixture was stirred under reflux for 1 h. The mixture was cooled down to RT and filtered through a pad of celite washing with MeOH. Solvent was eliminated under reduced pressure affording 4-[(tert-butylamino)methyl]piperidin-4-ol (P23, 180 mg, y=quant.), as white solid.

MS (ES) (m/z): 177.1 [M+H]$^+$.

Example 9

4-[(tert-butylamino)methyl]-1-[4-(3-fluorophenoxy)-6-(trifluoromethyl)pyrimidin-2-yl]piperidin-4-ol (E9)

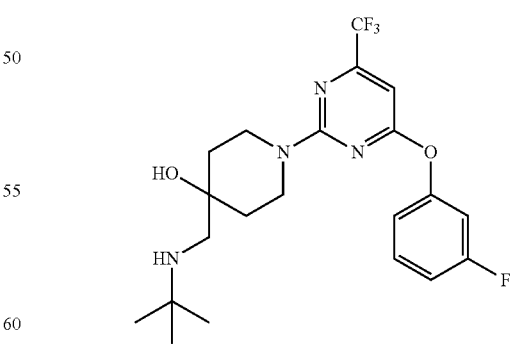

A mixture of 2-chloro-4-(3-fluorophenoxy)-6-(trifluoromethyl)pyrimidine (P2, 73 mg, 0.249 mmol), 4-[(tert-butylamino)methyl]piperidin-4-ol (P23, 50 mg, 0.268 mmol) and K$_2$CO$_3$ (44 mg, 0.323 mmol) in DMSO (0.8 mL) was heated at 45° C. for 1 h.

After cooling to RT, EtOAc and water were added and the product was extracted in organic phase. The organic phase was dried and evaporated, the residue was purified by FC on NH column (eluent: cHex to cHex/EtOAc 80/20) affording 4-[(tert-butylamino)methyl]-1-[4-(3-fluorophenoxy)-6-(trifluoromethyl)pyrimidin-2-yl]piperidin-4-ol (E9, 59 mg, y=53%) as yellowish oil.

MS (ES) (m/z): 443.20 [M+H]+.

$^1$H NMR (DMSO-d$_6$): δ ppm 7.57-7.46 (m, 1H), 7.26-7.06 (m, 3H), 6.55 (s, 1H), 4.09 (br. s., 3H), 3.29 (br. s., 2H), 2.42 (s, 2H), 1.48 (br. s., 4H), 1.29 (d, 1H), 1.03 (s, 9H)

Preparation 24: 1-[(1-benzyl-4-hydroxypiperidin-4-yl)methyl]pyrrolidin-2-one (P24)

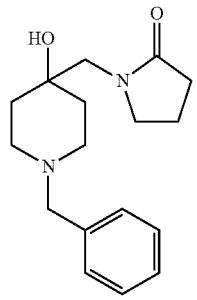 [SMILES: O=C1CCCN1CC1(O)CCN(Cc2ccccc2)CC1]

To a mixture of pyrrolidin-2-one (250 mg, 2.94 mmol) in DMF (10 mL) at 0° C., NaH 60% dispersion in mineral oil (125 mg, 3.2. mmol) was added and the suspension was stirred at 0° C. for 30 min, then a solution of 6-benzyl-1-oxa-6-azaspiro[2.5]octane (P8, 200 mg, 0.98 mmol) in DMF (2 mL) was added. The mixture was allowed to reach RT and stirred at that temperature for 1.5 hr. The mixture was then heated to 80° C. and stirred at that temperature for further 2 hrs. Reaction mixture was cooled down to RT, poured into water/ice and extracted twice with AcOEt. Organic phase was dried and concentrated under reduced pressure and the residue containing DMF was loaded on a SCX cartridge, washed with MeOH and eluted with NH$_3$ 1M in MeOH. Solvent was eliminated under reduced pressure affording 1-[(1-benzyl-4-hydroxypiperidin-4-yl)methyl]pyrrolidin-2-one (P24, 128 mg, y=45%).

MS (ES) (m/z): 289.2 [M+H]+.

Preparation 25: 1-[(4-hydroxypiperidin-4-yl)methyl]pyrrolidin-2-one (P25)

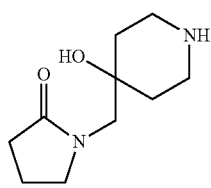 [SMILES: O=C1CCCN1CC1(O)CCNCC1]

To a solution of 1-[(1-benzyl-4-hydroxypiperidin-4-yl)methyl]pyrrolidin-2-one (P24, 128 mg, 0.44 mmol) in MeOH (5 mL) ammonium formate (0.168 g, 2.66 mmol) and 10% Pd/C (15 mg) were added at RT then the mixture was stirred under reflux for 1.5 h. The mixture was cooled down to RT and filtered through a pad of celite washing with MeOH. Solvent was eliminated under reduced pressure affording 1-[(4-hydroxypiperidin-4-yl)methyl]pyrrolidin-2-one (P25, 85 mg, y=97%)

MS (ES) (m/z): 199.1 [M+H]+.

Example 10

1-({1-[4-(3-fluorophenoxy)-6-(trifluoromethyl)pyrimidin-2-yl]-4-hydroxypiperidin-4-yl}methyl)pyrrolidin-2-one (E10)

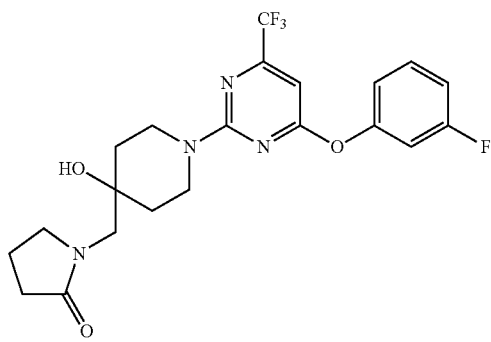 [SMILES: O=C1CCCN1CC1(O)CCN(c2nc(Oc3cccc(F)c3)cc(C(F)(F)F)n2)CC1]

To a solution of 1-[(4-hydroxypiperidin-4-yl)methyl]pyrrolidin-2-one (P25, 82 mg, 0.35 mmol) in DMSO (2 mL) 2-chloro-4-(3-fluorophenoxy)-6-(trifluoromethyl)pyrimidine (P2, 103 mg, 0.35 mmol) and K$_2$CO$_3$ (97 mg, 0.7 mmol) were added at RT then the mixture was shaken at 50° C. for 2 hrs. The mixture was cooled down, diluted with DCM and washed with water. Organic phase was dried and concentrated and the crude material was purified by FC on Silica gel (eluent: Cy to AcOEt), affording 1-({1-[4-(3-fluorophenoxy)-6-(trifluoromethyl)pyrimidin-2-yl]-4-hydroxypiperidin-4-yl}methyl)pyrrolidin-2-one (E10, 85 mg, y=53%).

MS (ES) (m/z): 455.01 [M+H]+.

$^1$H NMR (CHLOROFORM-d): δ ppm 7.47-7.35 (m, 1 H), 7.08-6.89 (m, 3 H) 6.35 (s, 1 H) 4.70-4.13 (m, 2 H) 3.54 (t, 2 H) 3.45-3.23 (m, 4 H) 2.48 (t, 2 H) 2.20-2.03 (m, 2 H) 1.64 (s, 2 H) 1.48 (s, 2H)

Preparation 26: 4-(aminomethyl)-1-benzylpiperidin-4-ol (P26)

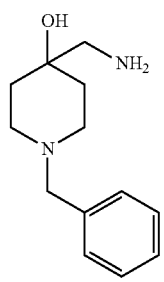 [SMILES: NCC1(O)CCN(Cc2ccccc2)CC1]

To a stirred solution of 6-benzyl-1-oxa-6-azaspiro[2.5]octane (P8, 3 g, 14.7 mmol) in MeOH (18 mL), at 0° C., 28% aq. NH₄OH (36 mL) was added. Once the addition was complete, the ice-bath was removed and the resulting reaction mixture was stirred at RT overnight. Then, reaction mixture was concentrated under reduced pressure, the residue was taken up with DCM and 1N NaOH, aqueous phase was back extracted with DCM, combined organics were dried and concentrated under reduced pressure. 4-(aminomethyl)-1-benzylpiperidin-4-ol (P26, 2.9 g, y=89%) was obtained as colourless oil. Used as such in next step MS (ES) (m/z): 221.10 [M+H]⁺.

Preparation 27: tert-butyl N-[(1-benzyl-4-hydroxypiperidin-4-yl)methyl]carbamate (P27)

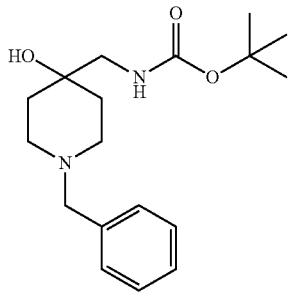 [SMILES: CC(C)(C)OC(=O)NCC1(O)CCN(Cc2ccccc2)CC1]

To a solution of 4-(aminomethyl)-1-benzylpiperidin-4-ol (P26, 2.9 g, 13.18 mmol) in DCM (30 mL) a solution of Boc₂O (2.87 mg, 13.18 mmol) in DCM (20 mL) was added and the mixture was stirred at RT for 14 hrs. The solvent was eliminated under reduced pressure and crude material purified by FC on silica gel (eluent: Cy to AcOEt) affording tert-butyl N-[(1-benzyl-4-hydroxypiperidin-4-yl)methyl]carbamate (P27, 2.9 g, y=68.7%) as a white solid.

MS (ES) (m/z): 321.11 [M+H]⁺.

Preparation 28: tert-butyl N-[(4-hydroxypiperidin-4-yl)methyl]carbamate (P28)

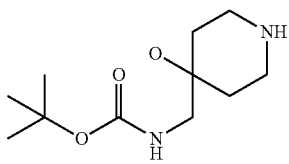 [SMILES: CC(C)(C)OC(=O)NCC1(O)CCNCC1]

To a solution of tert-butyl N-[(1-benzyl-4-hydroxypiperidin-4-yl)methyl]carbamate (P27, 2.9 g, 9.06 mmol) in MeOH (50 mL) ammonium formate (3.42 g, 54.3 mmol) and 10% Pd/C (0.3 g) were added at RT then the mixture was stirred under reflux for 1 h. The mixture was cooled down to RT and filtered through a pad of celite washing with MeOH. Solvent was eliminated under reduced pressure affording tert-butyl N-[(4-hydroxypiperidin-4-yl)methyl]carbamate (P28, 2.2 g, y=quant. 90% weight), as clear oil.

MS (ES) (m/z): 231.0 [M+H]⁺.

Preparation 29: tert-butyl N-({1-[4-(3-fluorophenoxy)-6-(trifluoromethyl)pyrimidin-2-yl]-4-hydroxypiperidin-4-yl}methyl)carbamate (P29)

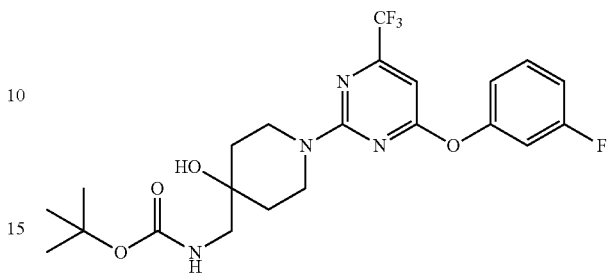

To a solution of tert-butyl N-[(4-hydroxypiperidin-4-yl)methyl]carbamate (P28, 0.34 g, 1.36 mmol (90% weight) in DMSO (6 mL) 2-chloro-4-(3-fluorophenoxy)-6-(trifluoromethyl)pyrimidine (P2, 0.4 g, 1.36 mmol) and K₂CO₃ (0.37 g, 2.72 mmol) were added at RT then the mixture was shaken at 50° C. for 2 hrs. The mixture was cooled down, diluted with DCM and washed with water. Organic phase was dried and concentrated and the crude material purified by FC on silica gel (eluent: Cy to Cy/AcOEt 1:1) affording tert-butyl N-({1-[4-(3-fluorophenoxy)-6-(trifluoromethyl)pyrimidin-2-yl]-4-hydroxypiperidin-4-yl}methyl)carbamate (P29, 350 mg, y=53%) as a white solid.

MS (ES) (m/z): 487.0 [M+H]⁺.

Example 11

4-(aminomethyl)-1-[4-(3-fluorophenoxy)-6-(trifluoromethyl)pyrimidin-2-yl]piperidin-4-ol (E11)

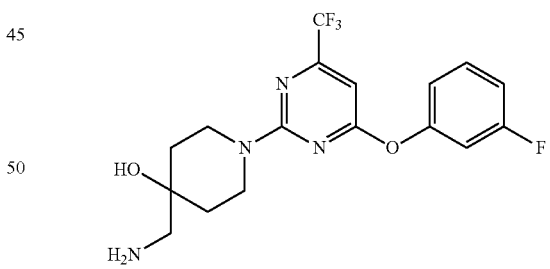

TFA (0.5 mL) was added to a solution of tert-butyl N-({1-[4-(3-fluorophenoxy)-6-(trifluoromethyl)pyrimidin-2-yl]-4-hydroxypiperidin-4-yl}methyl)carbamate (P29, 150 mg, 0.308 mmol) in DCM (5 mL). The mixture was stirred at RT for 1 h, and then the solvent was removed under reduced pressure. The residue was charged on SCX cartridge washing with MeOH and eluting with 1M NH₃ in MeOH to afford 4-(aminomethyl)-1-[4-(3-fluorophenoxy)-6-(trifluoromethyl)pyrimidin-2-yl]piperidin-4-ol (E11, 105 mg, y=88%).

MS (ES) (m/z): 387.2 [M+H]⁺.

Example 12

4-(aminomethyl)-1-[4-(3-fluorophenoxy)-6-(trifluoromethyl)pyrimidin-2-yl]piperidin-4-ol hydrochloride (E12)

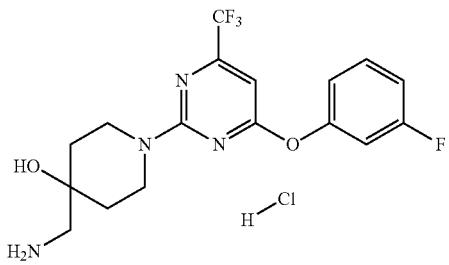

4-(aminomethyl)-1-[4-(3-fluorophenoxy)-6-(trifluoromethyl)pyrimidin-2-yl]piperidin-4-ol (E11, 80 mg, 0.207 mmol) was dissolved in DCM (1 mL) and treated with HCl 2M in diethyl ether (0.109 mL, 0.217 mmol). Then the solvent was evaporated to give 4-(aminomethyl)-1-[4-(3-fluorophenoxy)-6-(trifluoromethyl)pyrimidin-2-yl]piperidin-4-ol hydrochloride (E12, 88 mg, y=100%) as white solid.

MS (ES) (m/z): 387.2 [M+H]$^+$ $^1$H NMR (DMSO-d$_6$): δ ppm 7.56-7.46 (m, 1H), 7.35-7.10 (m, 5H), 6.65 (s, 1H), 5.04 (br. s., 1H), 4.22 (br. s., 1H), 3.85 (br. s., 1H), 3.21 (br. s., 2H), 2.72 (s, 2H), 1.47 (br. s., 6H) 1 H)

Preparation 30: tert-butyl N-({4-fluoro-1-[4-(3-fluorophenoxy)-6-(trifluoromethyl)pyrimidin-2-yl]piperidin-4-yl}methyl)carbamate (P30)

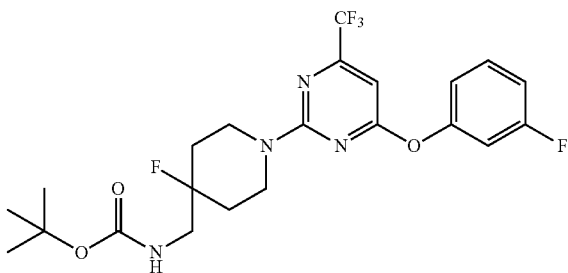 [SMILES: CC(C)(C)OC(=O)NCC1(F)CCN(c2nc(Oc3cccc(F)c3)cc(C(F)(F)F)n2)CC1]

To a solution of tert-butyl N-({1-[4-(3-fluorophenoxy)-6-(trifluoromethyl)pyrimidin-2-yl]-4-hydroxypiperidin-4-yl}methyl)carbamate (P29, 51 mg, 0.109 mmol) in DCM (2 mL) at 0° C. diethylaminosulfur trifluoride (0.029 mL, 0.218 mmol) was added and the reaction mixture was stirred for 1 h at 0° C. under N$_2$. NH$_4$Cl was added, the organic phase was separated, dried and solvent was evaporated. Crude material was purified by FC on silica gel (eluent: Cy to Cy/AcOEt 1:1) affording tert-butyl N-({4-fluoro-1-[4-(3-fluorophenoxy)-6-(trifluoromethyl)pyrimidin-2-yl]piperidin-4-yl}methyl)carbamate (P30, 28 mg, y=52%).

MS (m/z): 489.0 [M+H]$^+$.

Example 13

{4-fluoro-1-[4-(3-fluorophenoxy)-6-(trifluoromethyl)pyrimidin-2-yl]piperidin-4-yl}methanamine (E13)

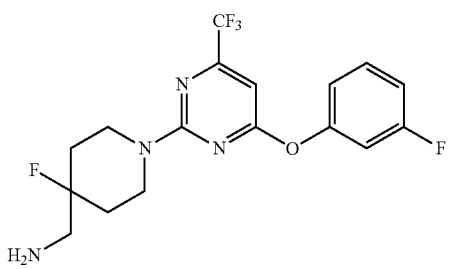 [SMILES: NCC1(F)CCN(c2nc(Oc3cccc(F)c3)cc(C(F)(F)F)n2)CC1]

To a solution of tert-butyl N-({4-fluoro-1-[4-(3-fluorophenoxy)-6-(trifluoromethyl)pyrimidin-2-yl]piperidin-4-yl}methyl)carbamate (P30, 28 mg, 0.057 mmol) in DCM (4 mL) 0.1 mL of TFA were added and the solution stirred at RT for 1 h. The reaction mixture was diluted with DCM and treated with NaHCO$_3$ saturated solution at 0° C. Organic phase was dried and concentrated under reduced pressure. Crude material was loaded on a SCX cartridge washing with MeOH and eluting with NH$_3$ 1M in MeOH affording {4-fluoro-1-[4-(3-fluorophenoxy)-6-(trifluoromethyl)pyrimidin-2-yl]piperidin-4-yl}methanamine (E13, 15 mg, y=68%).

MS (ES) (m/z): 388.99 [M+H]$^+$ $^1$H NMR (CHLOROFORM-d): δ ppm 7.45-7.35 (m, 1 H), 7.06-6.90 (m, 3 H), 6.39 (s, 1 H), 4.44 (br. s., 2 H), 3.23 (t, 2 H), 2.86 (s, 1 H), 2.81 (s, 1 H), 2.02-1.87 (m, 2 H), 1.65-1.41 (m, 2 H)

Preparation 31: tert-butyl N-({1-[3-fluoro-5-(3-fluorophenoxy)phenyl]-4-hydroxypiperidin-4-yl}methyl)carbamate (P31)

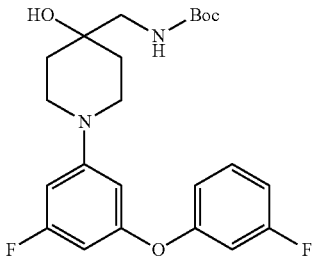 [SMILES: CC(C)(C)OC(=O)NCC1(O)CCN(c2cc(F)cc(Oc3cccc(F)c3)c2)CC1]

To a stirred solution of tert-butyl N-[(4-hydroxypiperidin-4-yl)methyl]carbamate (P28, 50 mg, 0.217 mmol) and 1-bromo-3-fluoro-5-(3-fluorophenoxy)benzene (P3, 62 mg, 0.21 mmol) in DME (2 mL) at RT, DavePhos (8.5 mg, 0.0217 mmol), Pd$_2$(dba)$_3$ (6 mg, 0.007 mmol) and K$_3$PO$_4$ (92 mg, 0.434 mmol) were added and nitrogen was purged for 10 min. Then the reaction was shaken at 110° C. overnight. The reaction mixture was partitioned between water and EtOAc, organic phase was separated, dried and concentrated under reduced pressure. Crude material was purified by FC on silica gel (eluent: Cy to Cy/AcOEt 70/30) affording tert-butyl N-({1-[3-fluoro-5-(3-fluorophenoxy)

Example 14

4-(aminomethyl)-1-[3-fluoro-5-(3-fluorophenoxy)phenyl]piperidin-4-ol (E14)

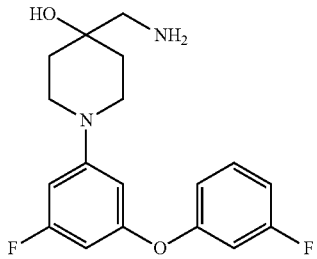 [SMILES: NCC1(O)CCN(c2cc(F)cc(Oc3cccc(F)c3)c2)CC1]

TFA (0.2 mL) was added to a solution of tert-butyl N-({1-[3-fluoro-5-(3-fluorophenoxy)phenyl]-4-hydroxypiperidin-4-yl}methyl)carbamate (P31, 37 mg, 0.085 mmol) in DCM (3 mL). The mixture was stirred for 1 h at RT, and then the solvent was removed under reduced pressure. The residue was charged on SCX cartridge eluting with 1M $NH_3$ in MeOH to afford 4-(aminomethyl)-1-[3-fluoro-5-(3-fluorophenoxy)phenyl]piperidin-4-ol (E14, 28 mg, y=98%) as pale yellow oil.

MS (ES) (m/z): 335.2 [M+H]+

$^1$H NMR (CHLOROFORM-d): δ ppm 7.36-7.26 (m, 1H), 6.89-6.79 (m, 2H), 6.75 (d, 1H), 6.47-6.37 (m, 2H), 6.16 (d, 1H), 3.48 (d, 2H), 3.24 (t, 2H), 2.70 (br. s., 2H), 1.74-1.54 (m, 4H)

Preparation 32: tert-butyl N-({1-[2,5-difluoro-3-(3-fluorophenoxy)phenyl]-4-hydroxypiperidin-4-yl}methyl)carbamate (P32)

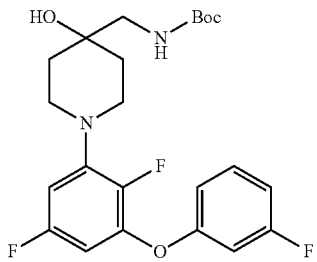 [SMILES: CC(C)(C)OC(=O)NCC1(O)CCN(c2cc(F)cc(Oc3cccc(F)c3)c2F)CC1]

To a stirred solution of tert-butyl N-[(4-hydroxypiperidin-4-yl)methyl]carbamate (P28, 50 mg, 0.217 mmol) and 1-bromo-2,5-difluoro-3-(3-fluorophenoxy)benzene (P5, 66 mg, 0.217 mmol) in DME (2 mL) at RT, DavePhos (8.5 mg, 0.0217 mmol), $Pd_2(dba)_3$ (6 mg, 0.007 mmol) and $K_3PO_4$ (92 mg, 0.434 mmol) were added and nitrogen was purged for 10 min. The reaction mixture was shaken at 110° C. overnight. The reaction mixture was partitioned between water and EtOAc, organic phase was separated, dried and concentrated under reduced pressure. Crude material was purified by FC on silica gel (eluent: Cy to Cy 70/AcOEt 30) affording tert-butyl N-({1-[2,5-difluoro-3-(3-fluorophenoxy)phenyl]-4-hydroxypiperidin-4-yl}methyl)carbamate (P32, 10 mg, y=10%), as yellow oil.

MS (ES) (m/z): 453.3 [M+H]+.

Example 15

4-(aminomethyl)-1-[2,5-difluoro-3-(3-fluorophenoxy)phenyl]piperidin-4-ol (E15)

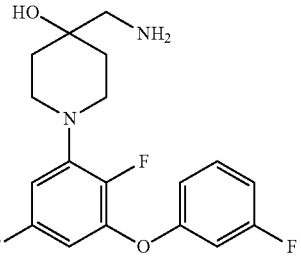

TFA (0.3 mL) was added to a solution of tert-butyl N-({1-[2,5-difluoro-3-(3-fluorophenoxy)phenyl]-4-hydroxypiperidin-4-yl}methyl)carbamate (P32, 10 mg, 0.022 mmol) in of DCM (3 mL). The mixture was stirred for 1 h at RT, and then the solvent was removed under reduced pressure. The residue was charged on SCX cartridge eluting with 1M $NH_3$ in MeOH to afford 4-(aminomethyl)-1-[2,5-difluoro-3-(3-fluorophenoxy)phenyl]piperidin-4-ol (E15, 7 mg, y=90%) as colorless oil.

MS (ES) (m/z): 353.2 [M+H]+.

$^1$H NMR (CHLOROFORM-d): δ ppm 7.33-7.23 (m, 1H), 6.87-6.75 (m, 2H), 6.71 (d, 1H), 6.55 (br. s., 1H), 6.40 (br. s., 1H), 3.28 (br. s., 2H), 3.13 (br. s., 2H), 2.68 (br. s., 2H), 1.69 (br. s., 4H)

Preparation 33: tert-butyl N-{[1-(2-fluoro-3-phenoxyphenyl)-4-hydroxypiperidin-4-yl]methyl}carbamate (P33)

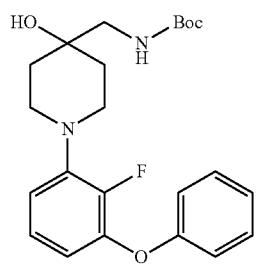

To a stirred solution of tert-butyl N-[(4-hydroxypiperidin-4-yl)methyl]carbamate (P28, 50 mg, 0.217 mmol) and 1-bromo-2-fluoro-3-phenoxybenzene (P6, 58 mg, 0.217 mmol) in DME (2 mL) at RT, DavePhos (8.5 mg, 0.0217 mmol), $Pd_2(dba)_3$ (6 mg, 0.007 mmol) and $K_3PO_4$ (92 mg, 0.434 mmol) were added and nitrogen was purged for 10 min. The reaction was then shaken at 110° C. overnight. The mixture was partitioned between water and EtOAc, organic phase was separated, dried and concentrated under reduced pressure. The crude material was purified by FC on silica gel (eluent: Cy to Cy70/AcOEt 30) affording tert-butyl N-{[1-(2-fluoro-3-phenoxyphenyl)-4-hydroxypiperidin-4-yl]methyl}carbamate (P33, 30 mg, y=33%), as yellow oil.

MS (ES) (m/z): 417.3 [M+H]+

Example 16

4-(aminomethyl)-1-(2-fluoro-3-phenoxyphenyl)piperidin-4-ol (E16)

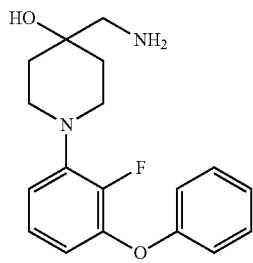 [SMILES: NCC1(O)CCN(c2cccc(Oc3ccccc3)c2F)CC1]

TFA (0.3 mL) was added to a solution of tert-butyl N-{[1-(2-fluoro-3-phenoxyphenyl)-4-hydroxypiperidin-4-yl]methyl}carbamate (P33, 30 mg, 0.72 mmol) in DCM (3 mL). The mixture was stirred at RT for 1 h, and then the solvent was removed under reduced pressure. The residue was charged on SCX cartridge eluting with 1M $NH_3$ in MeOH to afford 4-(aminomethyl)-1-(2-fluoro-3-phenoxyphenyl)piperidin-4-ol (E16, 18 mg, y=80%) as colorless oil.

MS (ES) (m/z): 317.2 [M+H]+

$^1$H NMR (CHLOROFORM-d): δ ppm 7.34 (t, 2H), 7.09 (t, 1H), 7.01 (d, 3H), 6.84 (t, 1H), 6.70 (t, 1H), 3.30 (d, 2H), 3.23-3.08 (m, 2H), 2.70 (s, 2H), 1.78-1.64 (m, 4H)

Preparation 34: tert-butyl N-({1-[2-fluoro-3-(3-fluorophenoxy)phenyl]-4-hydroxypiperidin-4-yl}methyl)carbamate (P34)

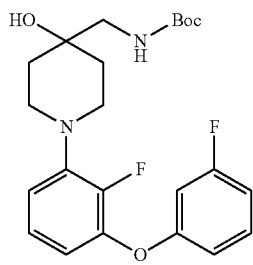 [SMILES: CC(C)(C)OC(=O)NCC1(O)CCN(c2cccc(Oc3cccc(F)c3)c2F)CC1]

To a stirred solution of tert-butyl N-[(4-hydroxypiperidin-4-yl)methyl]carbamate (P28, 50 mg, 0.217 mmol) and 1-bromo-2-fluoro-3-(3-fluorophenoxy)benzene (P7, 62 mg, 0.217 mmol) in DME (2 mL) at RT, DavePhos (8.5 mg, 0.0217 mmol), $Pd_2(dba)_3$ (6 mg, 0.007 mmol) and $K_3PO_4$ (92 mg, 0.434 mmol) were added and nitrogen was purged for 10 min. The reaction was then shaken at 110° C. overnight. The mixture was partitioned between water and EtOAc, organic phase was separated, dried and concentrated under reduced pressure. Crude material was purified by FC on silica gel (eluent: Cy to Cy 65/AcOEt 35) affording tert-butyl N-({1-[2-fluoro-3-(3-fluorophenoxy)phenyl]-4-hydroxypiperidin-4-yl}methyl)carbamate (P34, 30 mg, y=32%), as yellow oil.

MS (ES) (m/z): 435.3 [M+H]+.

Example 17

4-(aminomethyl)-1-[2-fluoro-3-(3-fluorophenoxy)phenyl]piperidin-4-ol (E17)

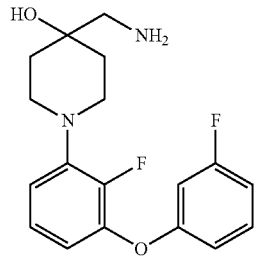

TFA (0.3 mL) was added to a solution of tert-butyl N-({1-[2-fluoro-3-(3-fluorophenoxy)phenyl]-4-hydroxypiperidin-4-yl}methyl)carbamate (P34, 30 mg, 0.069 mmol) in of DCM (3 mL). The mixture was stirred for 1 h at RT, and then the solvent was removed under reduced pressure. The residue was charged on SCX cartridge eluting with 1M $NH_3$ in MeOH to afford 4-(aminomethyl)-1-[2-fluoro-3-(3-fluorophenoxy)phenyl]piperidin-4-ol (E17, 18 mg, y=78%) as colourless oil.

MS (ES) (m/z): 335.2 [M+H]+.

$^1$H NMR (CHLOROFORM-d): δ ppm 7.29-7.23 (m, 1H), 7.09-7.00 (m, 1H), 6.87 (dd, 1H), 6.83-6.65 (m, 4H), 3.35-3.26 (m, 2H), 3.21-3.11 (m, 2H), 2.70 (br. s., 2H), 1.82 (t, 2H), 1.71 (br. s., 2H)

Preparation 35 and 36: tert-butyl N-({1-[2,3-difluoro-5-(3-fluorophenoxy)phenyl]-4-hydroxypiperidin-4-yl}methyl)carbamate (P35) and tert-butyl N-({1-[3,4-difluoro-5-(3-fluorophenoxy)phenyl]-4-hydroxypiperidin-4-yl}methyl)carbamate (P36)

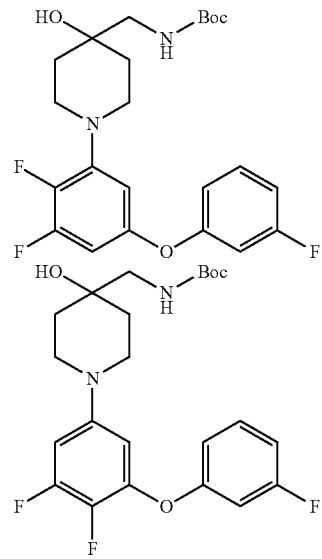

To a stirred solution of tert-butyl N-[(4-hydroxypiperidin-4-yl)methyl]carbamate (P28, 106 mg, 0.46 mmol) and a mixture ~1:1 of 1-bromo-2,3-difluoro-5-(3-fluorophenoxy)benzene and 5-bromo-1,2-difluoro-3-(3-fluorophenoxy)benzene (P4, 140 mg, 0.46 mmol) in DME (3 mL) at RT, DavePhos (18 mg, 0.046 mmol), $Pd_2(dba)_3$ (13 mg, 0.014 mmol) and $K_3PO_4$ (195 mg, 0.92 mmol) were added, then nitrogen was purged for 10 min and the mixture heated to 100° C. and stirred at that temperature overnight. The reaction mixture was partitioned between water and EtOAc, organic phase was separated, dried and concentrated under reduced pressure. The crude material was purified by FC on silica gel (eluent: Cy to Cy/AcOEt 60/40) affording tert-butyl N-({1-[2,3-difluoro-5-(3-fluorophenoxy)phenyl]-4-hydroxypiperidin-4-yl}methyl)carbamate (P35, 68 mg, y=32%), as yellow solid and tert-butyl N-({1-[3,4-difluoro-5-(3-fluorophenoxy)phenyl]-4-hydroxypiperidin-4-yl}methyl)carbamate (P36, 56 mg, y=26%) as yellow oil.
MS (ES) (m/z): 453.28 [M+H]$^+$.

Example 18

4-(aminomethyl)-1-[2,3-difluoro-5-(3-fluorophenoxy)phenyl]piperidin-4-ol (E18)

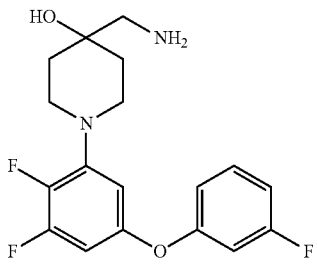 [SMILES: NCC1(O)CCN(c2cc(Oc3cccc(F)c3)cc(F)c2F)CC1]

TFA (0.5 mL) was added to a solution of tert-butyl N-({1-[2,3-difluoro-5-(3-fluorophenoxy)phenyl]-4-hydroxypiperidin-4-yl}methyl)carbamate (P35, 68 mg, 0.15 mmol) in DCM (3 mL) and the resulting mixture was stirred at RT for 1 h.
Solvent was removed in vacuum and the residue was charged on SCX cartridge eluting with MeOH and 1M NH3 in MeOH. After evaporation 4-(aminomethyl)-1-[2,3-difluoro-5-(3-fluorophenoxy)phenyl]piperidin-4-ol (E18, 50 mg, y=94%) was obtained as yellow oil.
MS (ES) (m/z): 353.26 [M+H]$^+$
$^1$H NMR (CHLOROFORM-d): δ ppm 7.37-7.30 (m, 1H), 6.90-6.76 (m, 2H), 6.72 (d, 1H), 6.53-6.39 (m, 2H), 3.38-3.22 (m, 2H), 3.12 (br. s., 2H), 2.69 (br. s., 2H), 1.69 (br. s., 4H)

Example 19

4-(aminomethyl)-1-[3,4-difluoro-5-(3-fluorophenoxy)phenyl]piperidin-4-ol (E19)

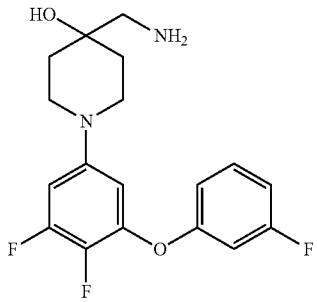 [SMILES: NCC1(O)CCN(c2cc(F)c(F)c(Oc3cccc(F)c3)c2)CC1]

TFA (0.5 mL) was added to a solution of tert-butyl N-({1-[3,4-difluoro-5-(3-fluorophenoxy)phenyl]-4-hydroxypiperidin-4-yl}methyl)carbamate (P44, 56 mg, 0.15 mmol) in DCM (3 mL), the resulting mixture was stirred at RT for 1 h. Solvent was removed in vacuum and the residue was charged on SCX cartridge eluting with MeOH and 1M NH$_3$ in MeOH. After evaporation 4-(aminomethyl)-1-[3,4-difluoro-5-(3-fluorophenoxy)phenyl]piperidin-4-ol (E19, 44 mg, y=quant) was obtained as yellow oil
MS (ES) (m/z): 353.26 [M+H]$^+$
$^1$H NMR (CHLOROFORM-d): δppm 7.36-7.23 (m, 1H), 6.89-6.76 (m, 2H), 6.73 (d, 1H), 6.60 (dd, 1H), 6.44 (br. s., 1H), 3.36 (d, 2H), 3.15 (t, 2H), 2.67 (br. s., 2H), 1.73-1.58 (m, 4H)

Preparation 37:
(4-amino-1-benzylpiperidin-4-yl)methanol (P37)

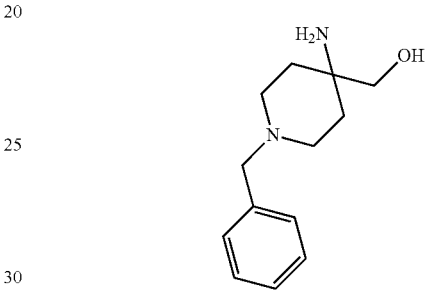

LiAlH$_4$ 2M in THF (4.27 mL, 8.54 mmol) was added to a solution of 4-amino-1-benzylpiperidine-4-carboxylic acid (500 mg, 2.13 mmol) in THF (12 mL) at 0° C. and then the mixture was refluxed for 2 hrs The stirred reaction mixture was cooled down to −10° C. and Na$_2$SO$_4$*10H$_2$O was carefully added portion-wise up to fizz end. The mixture was left stirring at RT for 30 min, then it was filtered; the solid was washed with DCM and the solvent concentrated under reduced pressure to give (4-amino-1-benzylpiperidin-4-yl)methanol (P37, 400 mg, y=85%) that was used as such.
MS (ES) (m/z): 221.2 [M+H]$^+$.

Preparation 38: tert-butyl N-[1-benzyl-4-(hydroxymethyl)piperidin-4-yl]carbamate (P38)

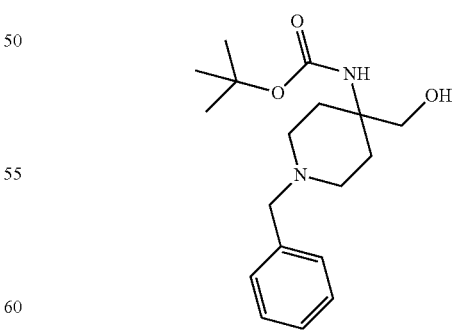

(4-amino-1-benzylpiperidin-4-yl)methanol (P37, 400 mg, 1.81 mmol) was dissolved in DCM (10 mL), TEA (0.4 mL, 2.71 mmol) was added followed by a solution of Boc$_2$O (435 mg, 1.99 mmol) in DCM (5 mL). The resulting solution was stirred at RT for 2 hrs. NH$_4$Cl was added; the organic phase was separated, dried and concentrated. The residue was purified by FC on NH column (eluent: Cy to Cy/EtOAc 40/60) affording tert-butyl N-[1-benzyl-4-(hydroxymethyl)piperidin-4-yl]carbamate (P38, 300 mg, y=52%) as white solid.

MS (ES) (m/z): 321.2 [M+H]+.

Preparation 39: tert-butyl N-[4-(hydroxymethyl)piperidin-4-yl]carbamate (P39)

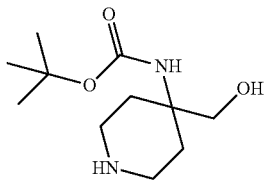 [SMILES: CC(C)(C)OC(=O)NC1(CO)CCNCC1]

To a solution of tert-butyl N-[1-benzyl-4-(hydroxymethyl)piperidin-4-yl]carbamate (P38, 300 mg, 0.936 mmol) in MeOH (7 mL) ammonium formate (354 mg, 5.62 mmol) and 10% Pd/C (90 mg) were added at RT then the mixture was stirred under reflux for 1 h. The mixture was cooled down to RT and filtered through a pad of celite washing with MeOH. Solvent was eliminated under reduced pressure affording tert-butyl N-[4-(hydroxymethyl)piperidin-4-yl]carbamate (P39, 200 mg, y=93%) as white solid.

MS (ES) (m/z): 231.2 [M+H]+.

Preparation 40: tert-butyl N-{1-[4-(3-fluorophenoxy)-6-(trifluoromethyl)pyrimidin-2-yl]-4-(hydroxymethyl)piperidin-4-yl}carbamate (P40)

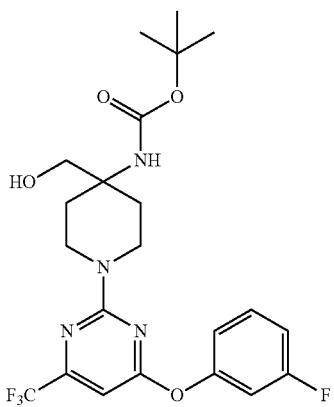 [SMILES: CC(C)(C)OC(=O)NC1(CO)CCN(c2nc(Oc3cccc(F)c3)cc(C(F)(F)F)n2)CC1]

tert-butyl N-[4-(hydroxymethyl)piperidin-4-yl]carbamate (P39, 75 mg, 0.326 mmol), 2-chloro-4-(3-fluorophenoxy)-6-(trifluoromethyl)pyrimidine (P2, 95 mg, 0.326 mmol) and K₂CO₃ (59 mg, 0.424 mmol) were mixed in dry DMSO (2 mL) and the mixture was shaken at 60° C. for 1 h. The mixture was cooled down, diluted with EtOAc and water. The organic phase was washed several times with brine, dried, filtered and evaporated. Crude material was purified by FC on silica gel (eluent: Cy to Cy/EtOAc 75/25) affording tert-butyl N-{1-[4-(3-fluorophenoxy)-6-(trifluoromethyl)pyrimidin-2-yl]-4-(hydroxymethyl)piperidin-4-yl}carbamate (P40, 90 mg, y=57%), as white solid.

MS (ES) (m/z): 487.3 [M+H]+.

Example 20

{4-amino-1-[4-(3-fluorophenoxy)-6-(trifluoromethyl)pyrimidin-2-yl]piperidin-4-yl}methanol (E20)

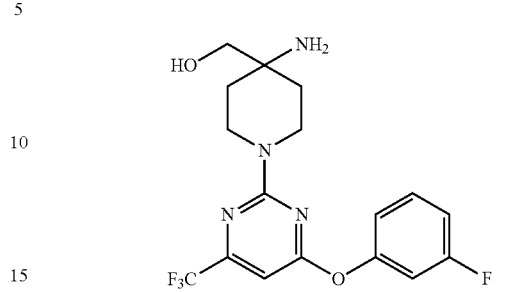

TFA (0.5 mL) was added to a solution of tert-butyl N-{1-[4-(3-fluorophenoxy)-6-(trifluoromethyl)pyrimidin-2-yl]-4-(hydroxymethyl)piperidin-4-yl}carbamate (P40, 90 mg, 0.185 mmol) in 8 mL of DCM. The mixture was stirred at RT for 1 h, and then the solvent was removed under reduced pressure. The residue was charged on SCX cartridge eluting with 1M NH₃ in MeOH to afford {4-amino-1-[4-(3-fluorophenoxy)-6-(trifluoromethyl)pyrimidin-2-yl]piperidin-4-yl}methanol (E20, 50 mg, y=70%)

MS (ES) (m/z): 387.2 [M+H]+

¹H NMR (DMSO-d₆): δ ppm 7.57-7.47 (m, 1H), 7.26 (td, 1H), 7.22-7.08 (m, 2H), 6.65-6.56 (m, 1H), 4.59 (br. s., 1H), 4.21 (br. s., 2H), 3.85 (br. s., 2H), 3.12 (br. s., 2H), 1.52 (br. s., 2H), 1.39 (br. s., 2H), 1.25 (br. s., 2H)

Example 21

N-({1-[4-(3-fluorophenoxy)-6-(trifluoromethyl)pyrimidin-2-yl]-4-hydroxypiperidin-4-yl}methyl)-2-methylpropanamide (E21)

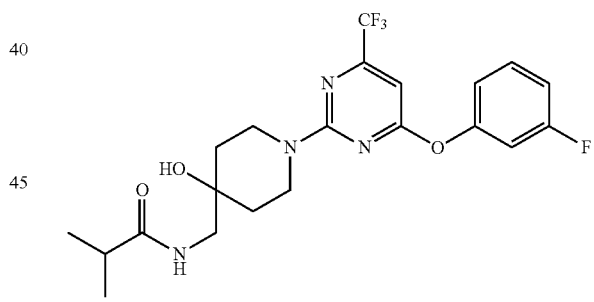

To a solution of isobutyric acid (5 μL, 0.054 mmol) in DCM (2 mL) EDC.HCl (11 mg, 0.057 mmol), HOBt (14 mg, 0.103 mmol) and TEA (14 μL, 0.103 mmol) were added. After 10 min at RT, 4-(aminomethyl)-1-[4-(3-fluorophenoxy)-6-(trifluoromethyl)pyrimidin-2-yl]piperidin-4-ol (E12, 20 mg, 0.0517 mmol) was added. The resulting solution was stirred at RT for 4 hrs. Solvent was evaporated and the residue was purified by FC on Silica gel (eluent: Cy to Cy/AcOEt 20/80) affording N-({1-[4-(3-fluorophenoxy)-6-(trifluoromethyl)pyrimidin-2-yl]-4-hydroxypiperidin-4-yl}methyl)-2-methylpropanamide (E21, 18.5 mg, y=78%) as white solid MS (ES) (m/z): 457.16 [M+H]+

¹H NMR (DMSO-d₆): δ ppm 7.65 (t, 1H), 7.57-7.47 (m, 1H), 7.25 (dd, 1H), 7.20-7.10 (m, 2H), 6.62 (s, 1H), 4.64 (s, 1H), 4.23 (br. s., 1H), 3.83 (br. s., 1H), 3.15 (br. s., 2H), 3.05 (d, 2H), 2.42 (dt, 1H), 1.36 (br. s., 4H), 0.97 (d, 6H)

Example 22

2-cyclopropyl-N-({1-[4-(3-fluorophenoxy)-6-(trifluoromethyl)pyrimidin-2-yl]-4-hydroxypiperidin-4-yl}methyl)acetamide (E22)

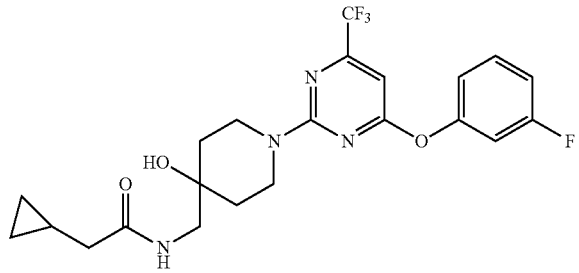 [SMILES: O=C(CC1CC1)NCC1(O)CCN(c2nc(Oc3cccc(F)c3)cc(C(F)(F)F)n2)CC1]

To a solution of cyclopropylacetic acid (7.5 μL, 0.081 mmol) in DCM (2 mL) EDC.HCl (16.5 mg, 0.086 mmol), HOBt (21 mg, 0.156 mmol) and TEA (22 μL, 0.156 mmol) were added. After 10 min at RT, 4-(aminomethyl)-1-[4-(3-fluorophenoxy)-6-(trifluoromethyl)pyrimidin-2-yl]piperidin-4-ol (E12, 30 mg, 0.078 mmol) was added. The resulting solution was stirred at RT for 4 hrs. Solvent was evaporated and the residue was purified by FC on Silica gel (eluent: Cy to Cy/AcOEt 20/80) affording 2-cyclopropyl-N-({1-[4-(3-fluorophenoxy)-6 (trifluoromethyl)pyrimidin-2-yl]-4-hydroxypiperidin-4-yl}methyl)acetamide as white solid (E22, 7.5 mg, y=21%)

MS (ES) (m/z): 469.05 [M+H]$^+$.

$^1$H NMR (CHLOROFORM-d): δ ppm 7.46-7.34 (m, 1H), 7.06-6.88 (m, 3H), 6.41 (br. s., 1H), 6.35 (s, 1H), 4.46 (br. s., 1H), 4.13 (br. s., 1H), 3.42 (br. s., 4H), 2.26 (br. s., 2H), 1.63 (br. s., 3H), 1.50 (br. s., 2H), 1.01 (br. s., 1H), 0.68 (br. s., 2H), 0.25 (br. s., 2H)

Example 23

N-({1-[4-(3-fluorophenoxy)-6-(trifluoromethyl)pyrimidin-2-yl]-4-hydroxypiperidin-4-yl}methyl)-2-(propan-2-yloxy)acetamide (E23)

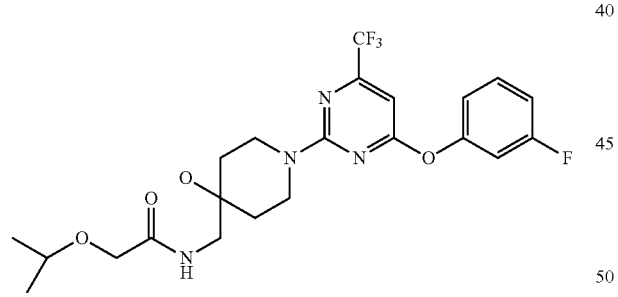

To a solution of isopropyloxyacetic acid (9.6 mg, 0.081 mmol) in DCM (2 mL) EDC.HCl (16.5 mg, 0.086 mmol), HOBt (21 mg, 0.156 mmol) and TEA (22 μL, 0.156 mmol) were added. After 10 min at RT, 4-(aminomethyl)-1-[4-(3-fluorophenoxy)-6-(trifluoromethyl)pyrimidin-2-yl]piperidin-4-ol (E11, 30 mg, 0.078 mmol) was added. The resulting solution was stirred at RT for 4 hrs. Solvent was evaporated and the residue was purified by FC on Silica gel (eluent: Cy to Cy/AcOEt 20/80) affording N-({1-[4-(3-fluorophenoxy)-6-(trifluoromethyl)pyrimidin-2-yl]-4-hydroxypiperidin-4-yl}methyl)-2-(propan-2-yloxy)acetamide as white solid (E23, 23.5 mg, y=62%)

MS (ES) (m/z): 487.07 [M+H]$^+$ $^1$H NMR (CHLOROFORM-d): δ ppm 7.44-7.31 (m, 1H), 7.06-6.88 (m, 4H), 6.35 (s, 1H), 4.41 (br. s., 1H), 4.15 (d, 1H), 3.99 (s, 2H), 3.69 (spt, 1H), 3.34 (d, J=6.0 Hz, 4H), 1.63 (d, 2H), 1.49 (br. s., 2H), 1.28-1.15 (m, 6H)

Example 24

N-({1-[4-(3-fluorophenoxy)-6-(trifluoromethyl)pyrimidin-2-yl]-4-hydroxypiperidin-4-yl}methyl)acetamide (E24)

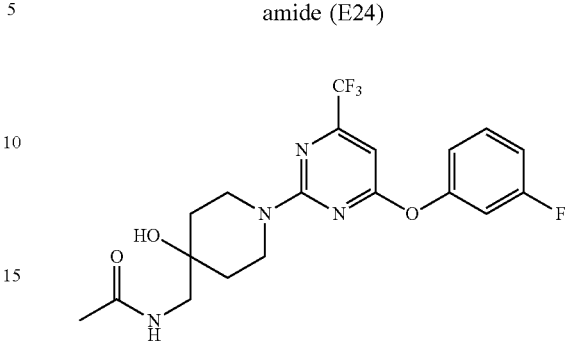

To a solution of acetic acid (4.7 μL, 0.078 mmol) in DCM (2 mL) EDC.HCl (16.5 mg, 0.086 mmol), HOBt (21 mg, 0.156 mmol) and TEA (22 μL, 0.156 mmol) were added. After 10 min at RT, 4-(aminomethyl)-1-[4-(3-fluorophenoxy)-6-(trifluoromethyl)pyrimidin-2-yl]piperidin-4-ol (E11, 30 mg, 0.078 mmol) was added. The resulting solution was stirred at RT for 4 hrs. Solvent was evaporated and the residue was purified by FC on Silica gel (eluent: Cy to Cy/AcOEt/MeOH 0/90/10) affording N-({1-[4-(3-fluorophenoxy)-6-(trifluoromethyl)pyrimidin-2-yl]-4-hydroxypiperidin-4-yl}methyl)acetamide as white solid (E24, 26 mg, y=77%)

MS (ES) (m/z): 429.05 [M+H]$^+$ $^1$H NMR (DMSO-d$_6$): δ ppm 7.74 (t, 1H), 7.47-7.58 (m, 1H), 7.22-7.31 (m, 1H), 7.09-7.22 (m, 2H), 6.62 (s, 1H), 4.61 (s, 1H), 4.24 (br. s., 1H), 3.87 (br. s., 1H), 3.19 (d, 2H), 3.06 (d, 3H), 1.84 (s, 3H), 1.39 (br. s., 4H)

Preparation 41: tert-butyl 3-[({1-[4-(3-fluorophenoxy)-6-(trifluoromethyl)pyrimidin-2-yl]-4-hydroxypiperidin-4-yl}methyl)carbamoyl]azetidine-1-carboxylate (P41)

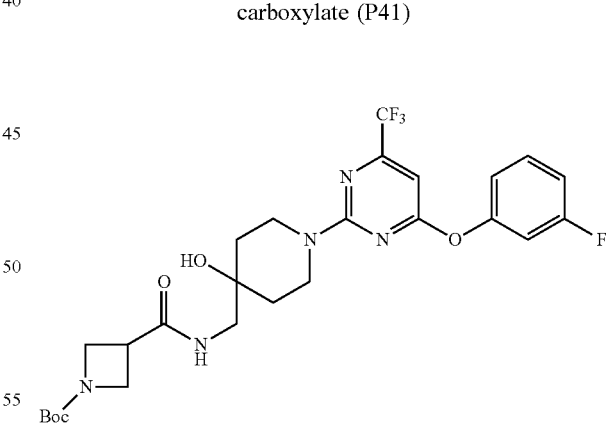

To a solution of 1-Boc-azetidine-3-carboxylic acid (82 mg, 0.4 mmol) in DCM (6 mL) EDC.HCl (82 mg, 0.423 mmol), HOBt (105 mg, 0.776 mmol) and TEA (108 μL, 0.776 mmol) were added. After 10 min at RT, 4-(aminomethyl)-1-[4-(3-fluorophenoxy)-6-(trifluoromethyl)pyrimidin-2-yl]piperidin-4-ol (E11, 150 mg, 0.388 mmol) was added. The resulting solution was stirred at RT for 12 hrs. Solvent was evaporated and the residue was purified by FC on Silica gel (eluent: Cy to AcOEt) affording tert-butyl 3-[({1-[4-(3-fluorophenoxy)-6-(trifluoromethyl)pyrimidin- 2-yl]-4-hydroxypiperidin-4-yl}methyl)carbamoyl]azetidine-1-carboxylate (P41, 90 mg, y=40%) as white foam.
MS (ES) (m/z): 570.3 [M+H]+

Example 25

N-({1-[4-(3-fluorophenoxy)-6-(trifluoromethyl)pyrimidin-2-yl]-4-hydroxypiperidin-4-yl}methyl)azetidine-3-carboxamide (E25)

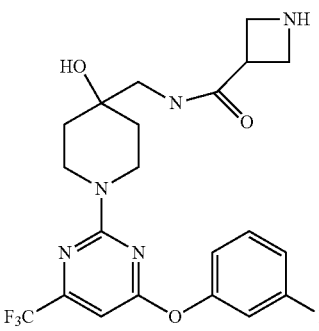

To a solution of tert-butyl 3-[({1-[4-(3-fluorophenoxy)-6-(trifluoromethyl)pyrimidin-2-yl]-4-hydroxypiperidin-4-yl}methyl)carbamoyl]azetidine-1-carboxylate (P41, 85 mg, 0.15 mmol) in DCM (5 mL). 0.8 mL of TFA was added and the solution stirred at RT for 1 h. Solvent and TFA excess was evaporated under reduced pressure and the residue was charged on SCX cartridge eluting with 1M $NH_3$ in MeOH. After evaporation N-({1-[4-(3-fluorophenoxy)-6-(trifluoromethyl)pyrimidin-2-yl]-4-hydroxypiperidin-4-yl}methyl)azetidine-3-carboxamide (E25, 70 mg, y=99%) was obtained as white solid.

MS (ES) (m/z): 470.06 [M+H]$^{30}$
$^1$H NMR (DMSO-$d_6$): δ ppm 7.65 (t, 1H), 7.59-7.46 (m, 1H), 7.31-7.22 (m, 1H), 7.22-7.10 (m, 2H), 6.62 (s, 1H), 4.62 (s, 1H), 4.25 (br. s., 1H), 3.86 (br. s., 1H), 3.726-3.56 (m, 2H), 3.46-3.36 (m, 3H), 3.18 (br. s., 2H), 3.09 (d, 2H), 1.38 (br. s., 4H)

Example 26

N-({1-[4-(3-fluorophenoxy)-6-(trifluoromethyl)pyrimidin-2-yl]-4-hydroxypiperidin-4-yl}methyl)benzamide (E26)

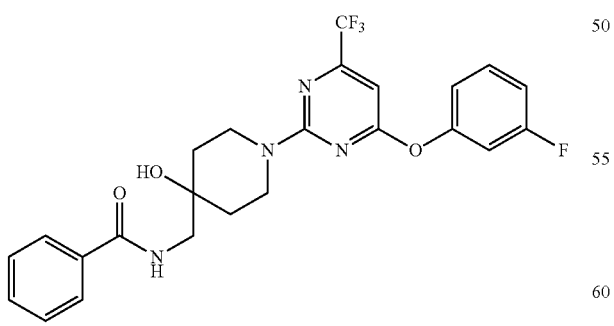

To a solution of benzoic acid (16 mg, 0.135 mmol) in DCM (2 mL) EDC.HCl (27 mg, 0.057 mmol), HOBt (35 mg, 0.258 mmol) and TEA (36 μL, 0.258 mmol) were added. After 20 min at RT, 4-(aminomethyl)-1-[4-(3-fluorophenoxy)-6-(trifluoromethyl)pyrimidin-2-yl]piperidin-4-ol (E11, 50 mg, 0.129 mmol) was added. The resulting solution was stirred at RT for 8 hrs. Solvent was evaporated and the residue was purified by FC on Silica gel (eluent: Cy to Cy/AcOEt 20/80) affording N-({1-[4-(3-fluorophenoxy)-6-(trifluoromethyl)pyrimidin-2-yl]-4-hydroxypiperidin-4-yl}methyl)benzamide (E26, 50 mg, y=79%) as white solid.

MS (ES) (m/z): 491.21 [M+H]$^+$.
$^1$H NMR (DMSO-$d_6$): δ ppm 8.31 (t, 1H), 7.85 (d, 2H), 7.58-7.41 (m, 4H), 7.25 (dt, 1H), 7.20-7.08 (m, 2H), 6.61 (s, 1H), 4.76 (s, 1H), 4.29 (br. s., 1H), 3.90 (br. s., 1H), 3.30 (d, 2H), 3.16 (br. s., 2H), 1.45 (br. s., 4H)

Example 27

N-({1-[4-(3-fluorophenoxy)-6-(trifluoromethyl)pyrimidin-2-yl]-4-hydroxypiperidin-4-yl}methyl)-1H-pyrazole-4-carboxamide (E27)

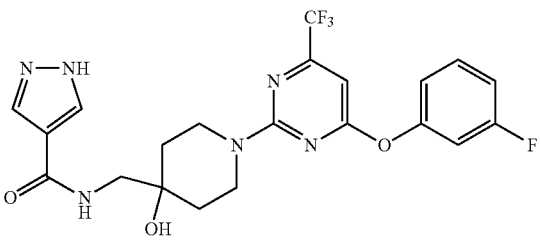 [SMILES: O=C(NCC1(O)CCN(c2nc(Oc3cccc(F)c3)cc(C(F)(F)F)n2)CC1)c1cn[nH]c1]

To a solution of 1H-pyrazole-4-carboxylic acid (14.5 mg, 0.135 mmol) in DCM (2 mL) EDC.HCl (27 mg, 0.057 mmol), HOBt (35 mg, 0.258 mmol) and TEA (36 μL, 0.258 mmol) were added. After 20 min at RT, 4-(aminomethyl)-1-[4-(3-fluorophenoxy)-6-(trifluoromethyl)pyrimidin-2-yl]piperidin-4-ol (E11, 50 mg, 0.129 mmol) was added. The resulting solution was stirred at RT for 3 hrs. Solvent was evaporated and the residue was purified by FC on Silica gel (eluent: Cy to AcOEt) affording N-({1-[4-(3-fluorophenoxy)-6-(trifluoromethyl)pyrimidin-2-yl]-4-hydroxypiperidin-4-yl}methyl)-1H-pyrazole-4-carboxamide (E27, 30 mg, y=48%)

MS (ES) (m/z): 481 [M+H]+
$^1$H NMR (DMSO-$d_6$): δ ppm 13.11 (br. s., 1H), 8.21 (br. s., 1H), 7.94 (t, J=6.0 Hz, 2H), 7.57-7.45 (m, 1H), 7.26 (d, 1H), 7.20-7.05 (m, 2H), 6.61 (s, 1H), 4.75 (s, 1H), 4.27 (br. s., 1H), 3.88 (br. s., 1H), 3.23 (d, 4H), 1.42 (br. s., 4H)

Example 28

N-({1-[4-(3-fluorophenoxy)-6-(trifluoromethyl)pyrimidin-2-yl]-4-hydroxypiperidin-4-yl}methyl)pyrazine-2-carboxamide (E28)

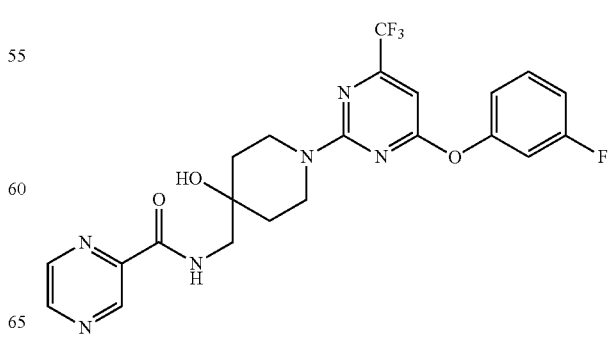

To a solution of Pyrazinecarboxylic acid (17 mg, 0.135 mmol) in DCM (2 mL) EDC.HCl (27 mg, 0.057 mmol), HOBt (35 mg, 0.258 mmol) and TEA (36 μL, 0.258 mmol) were added. After 20 min at RT, 4-(aminomethyl)-1-[4-(3-fluorophenoxy)-6-(trifluoromethyl)pyrimidin-2-yl]piperidin-4-ol (E11, 50 mg, 0.129 mmol) was added. The resulting solution was stirred at RT for 3 hrs. Solvent was evaporated and the residue was purified by FC on Silica gel (eluent: Cy to AcOEt) affording N-({1-[4-(3-fluorophenoxy)-6-(trifluoromethyl)pyrimidin-2-yl]-4-hydroxypiperidin-4-yl}methyl)pyrazine-2-carboxamide (E28, 17 mg, y=27%)

MS (ES) (m/z) 493.02 [M+H]$^+$ $^1$H NMR (DMSO-d$_6$): δ ppm 9.20 (d, 1H), 8.89 (d, 1H), 8.75 (s, 1H), 8.63 (t, 1H), 7.57-7.44 (m, 1H), 7.25 (d, 1H), 7.21-7.10 (m, 2H), 6.62 (s, 1H), 4.89 (s, 1H), 4.27 (br. s., 1H), 3.86 (br. s., 1H), 3.37 (br. s., 2H), 3.18 (br. s., 2H), 1.46 (br. s., 4H)

Preparation 42: tert-butyl N-{[({1-[4-(3-fluorophenoxy)-6-(trifluoromethyl)pyrimidin-2-yl]-4-hydroxypiperidin-4-yl}methyl)carbamoyl]methyl}carbamate (P42)

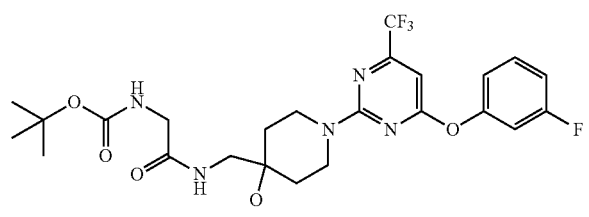 [SMILES: CC(C)(C)OC(=O)NCC(=O)NCC1(O)CCN(c2nc(Oc3cccc(F)c3)cc(C(F)(F)F)n2)CC1]

To a solution of N-Boc-Gly (22.6 mg, 0.129 mmol) in DCM (2 mL) EDC.HCl (27 mg, 0.057 mmol), HOBt (35 mg, 0.258 mmol) and TEA (36 μL, 0.258 mmol) were added. After 20 min at RT, 4-(aminomethyl)-1-[4-(3-fluorophenoxy)-6-(trifluoromethyl)pyrimidin-2-yl]piperidin-4-ol (E11, 50 mg, 0.129 mmol) was added. The resulting solution was stirred at RT for 3 hrs. Solvent was evaporated and the residue was purified by FC on Silica gel (eluent: Cy to AcOEt) affording tert-butyl N-{[({1-[4-(3-fluorophenoxy)-6-(trifluoromethyl)pyrimidin-2-yl]-4-hydroxypiperidin-4-yl}methyl)carbamoyl]methyl}carbamate (P42, 26 mg, y=37%)

MS (ES) (m/z): 544.1 [M+H]$^+$.

Example 29

2-amino-N-({1-[4-(3-fluorophenoxy)-6-(trifluoromethyl)pyrimidin-2-yl]-4-hydroxypiperidin-4-yl}methyl)acetamide (E29)

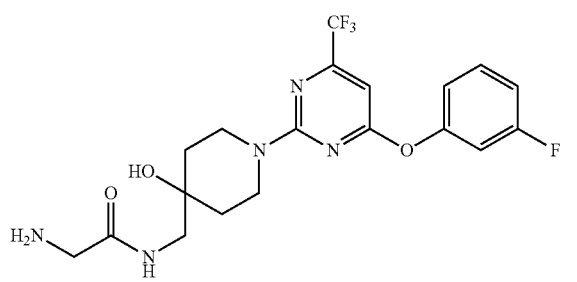 [SMILES: NCC(=O)NCC1(O)CCN(c2nc(Oc3cccc(F)c3)cc(C(F)(F)F)n2)CC1]

To a solution of tert-butyl N-{[({1-[4-(3-fluorophenoxy)-6-(trifluoromethyl)pyrimidin-2-yl]-4-hydroxypiperidin-4-yl}methyl)carbamoyl]methyl}carbamate (P42, 26 mg, 0.048 mmol) in DCM (2 mL) TFA was added and the solution was stirred at RT for 1 hr. Solvent and excess of TFA were removed under reduced pressure and the residue was dissolved in MeOH and loaded on a SCX cartridge washing with MeOH and eluting with NH$_3$ 2M in MeOH. Affording 2-amino-N-({1-[4-(3-fluorophenoxy)-6-(trifluoromethyl)pyrimidin-2-yl]-4-hydroxypiperidin-4-yl}methyl)acetamide (E29, 18 mg, y=84%).

MS (ES) (m/z): 444.01 [M+H]$^{30}$ $^1$H NMR (DMSO-d$_6$): δ ppm 7.81 (br. s., 1 H) 7.58-7.45 (m, 1 H) 7.25 (t, 1 H) 7.27 (t, 1 H) 7.22-7.09 (m, 2 H) 6.62 (s, 1 H) 4.71 (s, 1 H) 4.21 (br. s., 2 H) 3.83 (br. s., 2 H), 3.17-2.96 (m, 4 H) 1.99 (br. s., 2H) 1.39 (br. s., 4 H)

Preparation 43:
5-benzyl-1-oxa-5-azaspiro[2.4]heptane (P43)

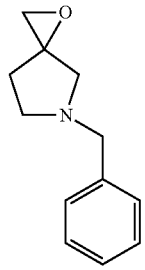 [SMILES: c1ccc(CN2CCC3(CO3)C2)cc1]

To an ice-cooled mixture of NaH 60% dispersion in mineral oil (0.297 g, 7.42 mmol.) and trimethylsulfoxonium iodide (1.38 g, 6.28 mmol) was added DMSO (5 mL) keeping the mixture at 10° C. After stirred for 10 min at 10° C., it was allowed to reach RT and left stirring at that temperature for 1 h. A solution of 1-benzylpyrrolidin-3-one (0.92 mL, 5.71 mmol.) in DMSO (5 mL) was added via syringe. The mixture was stirred for 3 hrs at RT, diluted with Et$_2$O and quenched by the addition of saturated aqueous NH$_4$Cl. Phases were separated and aqueous one was back-extracted with Et$_2$O. Combined organics were dried, filtered and concentrated under reduced pressure. Crude 5-benzyl-1-oxa-5-azaspiro[2.4]heptane (P43, 850 mg, y=79%) was used as such in next step.

MS (ES) (m/z): 427.2 [M+H]$^+$.

Preparation 44: 1-benzyl-3-[(cyclopropylamino)methyl]pyrrolidin-3-ol (P44)

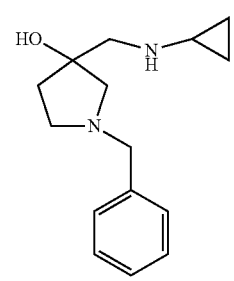 [SMILES: OC1(CNC2CC2)CCN(Cc2ccccc2)C1]

To a stirred solution of 5-benzyl-1-oxa-5-azaspiro[2.4]heptane (P43, 200 mg, 1.06 mmol) in MeOH (1 mL), at 0° C., cyclopropylamine (0.15 mL, 2.11 mmol) was added dropwise. Once the addition was complete, the ice-bath was removed and the resulting reaction mixture was stirred at RT overnight. Then, reaction mixture was concentrated under reduced pressure, the residue was taken up with DCM, the aqueous phase was extracted and then the combined organics were dried and concentrated under reduced pressure to afford 1-benzyl-3-[(cyclopropylamino)methyl]pyrrolidin-3-ol (P44, 160 mg, y=61%).

MS (ES) (m/z): 247.1 [M+H]$^+$.

Preparation 45: tert-butyl N-[(1-benzyl-3-hydroxypyrrolidin-3-yl)methyl]-N-cyclopropylcarbamate (P45)

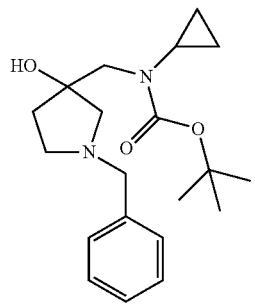 [SMILES: CC(C)(C)OC(=O)N(CC1(O)CCN(Cc2ccccc2)C1)C1CC1]

1-benzyl-3-[(cyclopropylamino)methyl]pyrrolidin-3-ol (P44, 160 mg, 0.649 mmol) was dissolved in DCM (2 mL), TEA (0.14 mL, 0.974 mmol) was added followed by a solution of Boc$_2$O (170 mg, 0.779 mmol) in DCM (1 mL). The resulting solution was stirred at RT for 2 hrs. NH$_4$Cl was added; the organic phase was separated, dried and concentrated. The residue was purified by FC on Silica gel (eluent: Cy to Cy/AcOEt 70/30) affording tert-butyl N-[(1-benzyl-3-hydroxypyrrolidin-3-yl)methyl]-N-cyclopropylcarbamate (P45, 110 mg, y=50%) as colorless oil.

MS (ES) (m/z): 347.2 [M+H]$^+$.

Preparation 46: tert-butyl N-cyclopropyl-N-[(3-hydroxypyrrolidin-3-yl)methyl]carbamate (P46)

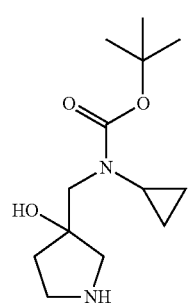

To a solution of tert-butyl N-[(1-benzyl-3-hydroxypyrrolidin-3-yl)methyl]-N-cyclopropylcarbamate (P45, 110 mg, 0.317 mmol) in MeOH (3 mL) ammonium formate (120 mg, 1.90 mmol) and 10% Pd/C (32 mg) were added at RT, then the mixture was stirred under reflux for 1 h. The mixture was then cooled down to RT and filtered through a pad of celite washing with MeOH. Solvent was eliminated under reduced pressure affording tert-butyl N-cyclopropyl-N-[(3-hydroxypyrrolidin-3-yl)methyl]carbamate (P46, 75 mg, y=75%), as colourless oil.

MS (ES) (m/z): 257.2 [M+H]$^+$.

Preparation 47: tert-butyl N-cyclopropyl-N-({1-[4-(3-fluorophenoxy)-6-(trifluoromethyl)pyrimidin-2-yl]-3-hydroxypyrrolidin-3-yl}methyl)carbamate (P47)

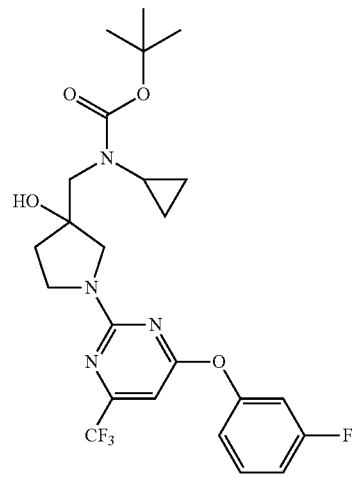 [SMILES: CC(C)(C)OC(=O)N(CC1(O)CCN(c2nc(Oc3cccc(F)c3)cc(C(F)(F)F)n2)C1)C1CC1]

2-chloro-4-(3-fluorophenoxy)-6-(trifluoromethyl)pyrimidine (P2, 85 mg, 0.293 mmol), tert-butyl N-cyclopropyl-N-[(3-hydroxypyrrolidin-3-yl)methyl]carbamate (P46, 75 mg, 0.293 mmol) and K$_2$CO$_3$ (53 mg, 0.381 mmol) were mixed in dry DMSO (2 mL) and the mixture was shaken at 60° C. for 1 hr. The mixture was diluted with EtOAC and water. The organic phase was washed several times with brine, dried, filtered and evaporated. Crude material was purified by FC on NH column (eluent: Cy to Cy/AcOEt 85/15) affording tert-butyl N-cyclopropyl-N-({1-[4-(3-fluorophenoxy)-6-(trifluoromethyl)pyrimidin-2-yl]-3-hydroxypyrrolidin-3-yl}methyl)carbamate (P47, 80 mg, y=53%).

MS (ES) (m/z): 513.2 [M+H]$^+$.

Example 30

3-[(cyclopropylamino)methyl]-1-[4-(3-fluorophenoxy)-6-(trifluoromethyl)pyrimidin-2-yl]pyrrolidin-3-ol (E30)

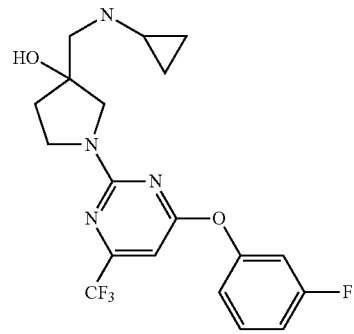 [SMILES: OC1(CNC2CC2)CCN(c2nc(Oc3cccc(F)c3)cc(C(F)(F)F)n2)C1]

TFA (0.3 mL) was added to a solution of tert-butyl N-cyclopropyl-N-({1-[4-(3-fluorophenoxy)-6-(trifluoromethyl)pyrimidin-2-yl]-3-hydroxypyrrolidin-3-yl}methyl) carbamate (P47, 60 mg, 0.117 mmol) in 3 mL of DCM. The mixture was stirred at RT for 1 h, and then the solvent was removed under reduced pressure. The residue was charged on SCX cartridge eluting with 1M NH$_3$ in MeOH to afford 3-[(cyclopropylamino)methyl]-1-[4-(3-fluorophenoxy)-6-(trifluoromethyl)pyrimidin-2-yl]pyrrolidin-3-ol (E30, 40 mg, y=83%) as colorless oil.

MS (ES) (m/z): 413.18 [M+H]$^+$ $^1$H NMR (CHLOROFORM-d): δ ppm 7.44-7.33 (m, 1H), 7.05-6.89 (m, 3H), 6.37 (d, 1H), 3.91-3.66 (m, 2H), 3.60-3.40 (m, 2H), 3.26 (d, 1H), 3.04-2.86 (m, 2H), 2.34-2.18 (m, 1H), 2.02-1.78 (m, 3H), 0.60- 0.35 (m, 4H)

Examples 31 and 32

(3S or 3R)-3-[(cyclopropylamino)methyl]-1-[4-(3-fluorophenoxy)-6-(trifluoromethyl)pyrimidin-2-yl]pyrrolidin-3-ol (E31) and (3R or 3S)-3-[(cyclopropylamino)methyl]-1-[4-(3-fluorophenoxy)-6-(trifluoromethyl)pyrimidin-2-yl]pyrrolidin-3-ol (E32)

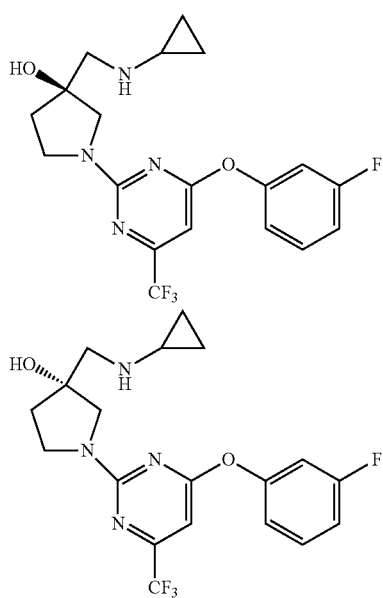

3-[(cyclopropylamino)methyl]-1-[4-(3-fluorophenoxy)-6-(trifluoromethyl)pyrimidin-2-yl]pyrrolidin-3-ol (E30, 30 mg) was submitted to chiral prep HPLC to separate single enantiomers.

Preparative HPLC Conditions and Results:

| Column | Chiralpak AD-H (25 × 2.0 cm), 5µ |
|---|---|
| Mobile phase | n-Hexane/(Ethanol + 0.1% isopropylamine) 75/25% v/v |
| Flow rate (mL/min) | 14 mL/min |
| DAD detection | 220 nm |
| Loop | 2000 µL |
| Total amount | 30 mg |
| Solubilization | 30 mg in 3.5 mL (Ethanol/Methanol 1/1)/n-Hex 70/30% v/v = 8.6 mg/mL |
| Injection | 17 mg/injection |

Affording:

(3S or 3R)-3-[(cyclopropylamino)methyl]-1-[4-(3-fluorophenoxy)-6-(trifluoromethyl)pyrimidin-2-yl]pyrrolidin-3-ol (E31, single enantiomer: enantiomer 1, 8.4 mg, y=28%) 100% ee (3R or 3S)-3-[(cyclopropylamino)methyl]-1-[4-(3-fluorophenoxy)-6-(trifluoromethyl)pyrimidin-2-yl]pyrrolidin-3-ol (E32, single enantiomer: enantiomer 2, 7.3 mg, y=24%) 100% ee Preparation 48:
3-(aminomethyl)-1-benzylpyrrolidin-3-ol (P48)

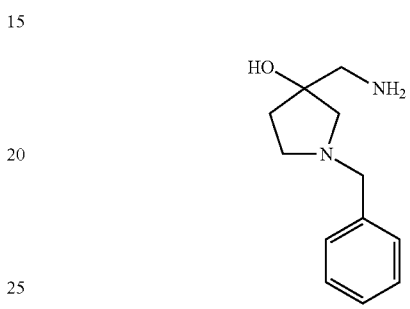

To a stirred solution of 5-benzyl-1-oxa-5-azaspiro[2.4]heptane (P43, 850 mg, 4.49 mmol) in MeOH (5 mL), at 0° C., 28% aq. NH$_4$OH (10 mL) was added dropwise. Once the addition was complete, the ice-bath was removed and the resulting reaction mixture was stirred at RT overnight. Then, reaction mixture was concentrated under reduced pressure, the residue was taken up with DCM, aqueous phase was back extracted with DCM, combined organics were dried and concentrated under reduced pressure to obtain 3-(aminomethyl)-1-benzylpyrrolidin-3-ol (P56, 900 mg, y=quant.).

MS (ES) (m/z): 207.1 [M+H]$^+$.

Preparation 49: tert-butyl N-[(1-benzyl-3-hydroxy-pyrrolidin-3-yl)methyl]carbamate (P49)

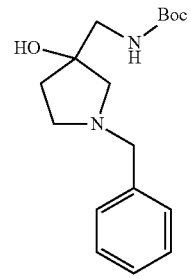 [SMILES: CC(C)(C)OC(=O)NCC1(O)CCN(Cc2ccccc2)C1]

3-(aminomethyl)-1-benzylpyrrolidin-3-ol (P48, 900 mg, 4.49 mmol) was dissolved in DCM (10 mL), TEA (0.94 mL, 6.74 mmol) was added followed by a solution of Boc$_2$O (1.18 g, 5.39 mmol) in DCM (5 mL). The resulting solution was stirred at RT for 2 hrs. NH$_4$Cl was added; the organic phase was separated, dried and concentrated. The residue was purified by FC on Silica gel (eluent: Cy to AcOEt) affording tert-butyl N-[(1-benzyl-3-hydroxypyrrolidin-3-yl)methyl]carbamate (P49, 470 mg, y=34%) as colorless oil.

MS (ES) (m/z): 307.2 [M+H]$^+$.

Preparation 50: tert-butyl N-[(3-hydroxypyrrolidin-3-yl)methyl]carbamate (P50)

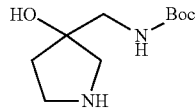

To a solution of tert-butyl N-[(1-benzyl-3-hydroxypyrrolidin-3-yl)methyl]carbamate (P49, 470 mg, 1.53 mmol) in MeOH (10 mL) ammonium formate (580 mg, 9.20 mmol) and 10% Pd/C (155 mg) were added at RT then the mixture was stirred under reflux for 3 hrs. The mixture was cooled down to RT and filtered through a pad of celite washing with MeOH. Solvent was eliminated under reduced pressure affording tert-butyl N-[(3-hydroxypyrrolidin-3-yl)methyl]carbamate (P50, 350 mg, y=quant.), as colourless oil.
MS (ES) (m/z): 217.1 [M+H]$^+$.

Preparation 51: tert-butyl N-({1-[4-(3-fluorophenoxy)-6-(trifluoromethyl)pyrimidin-2-yl]-3-hydroxypyrrolidin-3-yl}methyl)carbamate (P51)

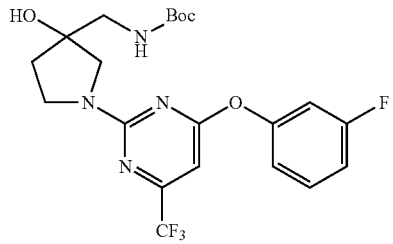 [SMILES: CC(C)(C)OC(=O)NCC1(O)CCN(c2nc(Oc3cccc(F)c3)cc(C(F)(F)F)n2)C1]

2-chloro-4-(3-fluorophenoxy)-6-(trifluoromethyl)pyrimidine (P2, 200 mg, 0.925 mmol), tert-butyl N-[(3-hydroxypyrrolidin-3-yl)methyl]carbamate (P50, 291 mg, 0.925 mmol) and K$_2$CO$_3$ (166 mg, 1.203 mmol) were mixed in dry DMSO (4 mL) and the mixture was shaken at 60° C. for 2 hr. The mixture was diluted with EtOAC and water. The organic phase was washed several times with brine, dried, filtered and concentrated. Crude material was purified by FC on Silica gel (eluent: Cy to Cy/AcOEt 80/20) affording tert-butyl N-({1-[4-(3-fluorophenoxy)-6-(trifluoromethyl)pyrimidin-2-yl]-3-hydroxypyrrolidin-3-yl}methyl)carbamate (P51, 200 mg, y=46%), as white solid.
MS (ES) (m/z): 473.2 [M+H]$^+$.

Example 33

3-(aminomethyl)-1-[4-(3-fluorophenoxy)-6-(trifluoromethyl)pyrimidin-2-yl]pyrrolidin-3-ol (E33)

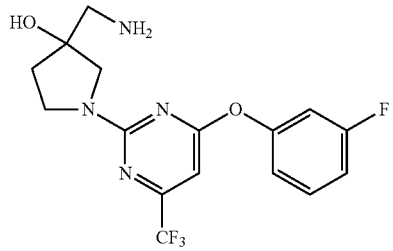 [SMILES: NCC1(O)CCN(c2nc(Oc3cccc(F)c3)cc(C(F)(F)F)n2)C1]

TFA (0.32 mL) was added to a solution of tert-butyl N-({1-[4-(3-fluorophenoxy)-6-(trifluoromethyl)pyrimidin-2-yl]-3-hydroxypyrrolidin-3-yl}methyl)carbamate (P51, 200 mg, 0.423 mmol) in 8 mL of DCM. The mixture was stirred at RT for 1 h, and then the solvent was removed under reduced pressure. The residue was charged on SCX cartridge eluting with 1M NH$_3$ in MeOH to afford 3-(aminomethyl)-1-[4-(3-fluorophenoxy)-6-(trifluoromethyl)pyrimidin-2-yl]pyrrolidin-3-ol (E33, 160 mg, y=quant.) as colorless oil.
MS (ES) (m/z): 373.2 [M+H]$^+$.

Example 34

N-({1-[4-(3-fluorophenoxy)-6-(trifluoromethyl)pyrimidin-2-yl]-3-hydroxypyrrolidin-3-yl}methyl)-2-methylpropanamide (E34)

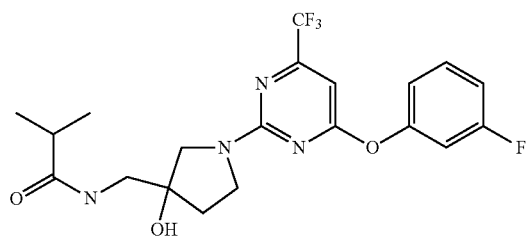 [SMILES: CC(C)C(=O)NCC1(O)CCN(c2nc(Oc3cccc(F)c3)cc(C(F)(F)F)n2)C1]

To a solution of isobutyric acid (13 μL, 0.141 mmol) in DCM (4 mL) EDC HCl (30 mg, 0.155 mmol), HOBt (36 mg, 0.268 mmol) and TEA (37 μL, 0.268 mmol) were added. After 10 min at RT, 3-(aminomethyl)-1-[4-(3-fluorophenoxy)-6-(trifluoromethyl)pyrimidin-2-yl]pyrrolidin-3-ol (E33, 50 mg, 0.134 mmol) was added. The resulting solution was stirred at RT for 4 hrs. Solvent was evaporated and the residue was purified by FC on Silica gel (eluent: Cy to Cy/AcOEt 30/70) affording N-({1-[4-(3-fluorophenoxy)-6-(trifluoromethyl)pyrimidin-2-yl]-3-hydroxypyrrolidin-3-yl}methyl)-2-methylpropanamide (E34, 59 mg, y=95%) as colourless oil.
MS (ES) (m/z): 443.24 [M+H]$^+$.
$^1$H NMR (CHLOROFORM-d): δ ppm 7.43-7.33 (m, 1H), 7.04-6.88 (m, 3H), 6.41 (s, 1H), 5.97 (br. s., 1H), 3.78 (m, 7H), 2.64 (s, 1H), 2.44 (br. s., 1H), 1.98 (br. s., 2H), 1.26-1.12 (m, 6H)

Preparation 52: tert-butyl 3-[({1-[4-(3-fluorophenoxy)-6-(trifluoromethyl)pyrimidin-2-yl]-3-hydroxypyrrolidin-3-yl}methyl)carbamoyl]azetidine-1-carboxylate (P52)

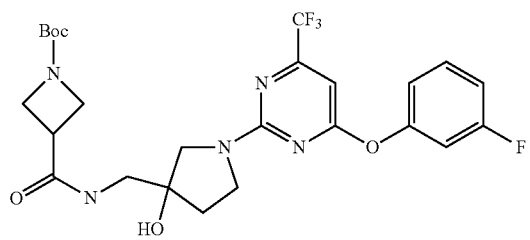 [SMILES: CC(C)(C)OC(=O)N1CC(C(=O)NCC2(O)CCN(c3nc(Oc4cccc(F)c4)cc(C(F)(F)F)n3)C2)C1]

To a solution of 1-Boc-azetidine-3-carboxylic acid (28 mg, 0.141 mmol) in DCM (4 mL) EDC HCl (30 mg, 0.155 mmol), HOBt (36 mg, 0.268 mmol) and TEA (0.037 mL, 0.268 mmol) were added. After 10 min at RT, 3-(aminomethyl)-1-[4-(3-fluorophenoxy)-6-(trifluoromethyl)pyrimidin-2-yl]pyrrolidin-3-ol (E33, 50 mg, 0.134 mmol) was added. The resulting solution was stirred at the same temperature overnight. Solvent was evaporated and the residue was purified by FC on Silica gel (eluent: Cy to AcOEt) affording tert-butyl 3-[({1-[4-(3-fluorophenoxy)-6-(trifluoromethyl)pyrimidin-2-yl]-3-hydroxypyrrolidin-3-yl}methyl)carbamoyl]azetidine-1-carboxylate (P52, 45 mg, y=61%) as white solid.

MS (ES) (m/z): 556.10 [M+H]$^+$

Example 35

N-({1-[4-(3-fluorophenoxy)-6-(trifluoromethyl)pyrimidin-2-yl]-3-hydroxypyrrolidin-3-yl}methyl)azetidine-3-carboxamide (E35)

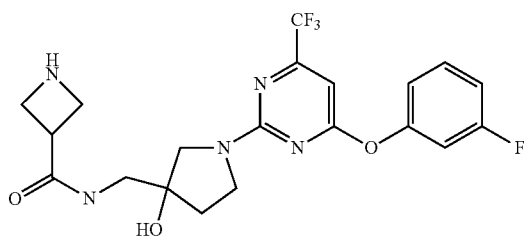 [SMILES: O=C(NCC1(O)CCN(c2nc(Oc3cccc(F)c3)cc(C(F)(F)F)n2)C1)C1CNC1]

TFA (0.3 mL) was added to a solution of tert-butyl 3-[({1-[4-(3-fluorophenoxy)-6-(trifluoromethyl)pyrimidin-2-yl]-3-hydroxypyrrolidin-3-yl}methyl)carbamoyl]azetidine-1-carboxylate (P52, 45 mg, 0.081 mmol) in 3 mL of DCM. The mixture was stirred at RT for 1 h, and then the solvent was removed under reduced pressure. The residue was charged on SCX cartridge eluting with 1M NH$_3$ in MeOH to afford N-({1-[4-(3-fluorophenoxy)-6-(trifluoromethyl)pyrimidin-2-yl]-3-hydroxypyrrolidin-3-yl}methyl)azetidine-3-carboxamide as white solid (E35, 36 mg, y=98%).

MS (ES) (m/z): 456.21 [M+H]$^+$
$^1$H NMR (DMSO-d$_6$): δ ppm 7.91-7.80-(m, 1H), 7.57-7.46 (m, 1H), 7.32-7.20 (m, 1H), 7.20-7.08 (m, 2H), 6.68-6.59-(m, 1H), 5.04 (d, 1H), 3.69-3.45 (m, 3H), 3.45-3.28 (m, 6H), 3.21-3.08 (m, 1H), 1.93- 1.68 (m, 2H)

Example 36

4-(3-fluorophenoxy)-2-{3H,4H,5H,6H,7H-imidazo[4,5-c]pyridin-5-yl}-6-(trifluoromethyl)pyrimidine (E36)

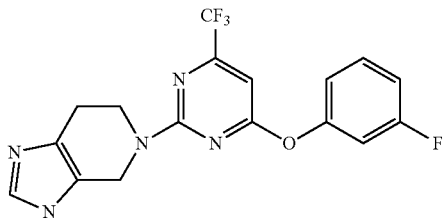 [SMILES: Fc1cccc(Oc2cc(C(F)(F)F)nc(N3CCc4nc[nH]c4C3)n2)c1]

A mixture of 3H,4H,5H,6H,7H-imidazo[4,5-c]pyridine hydrochloride (50 mg, 0.31 mmol), 2-chloro-4-(3-fluorophenoxy)-6-(trifluoromethyl)pyrimidine (P2, 91 mg, 0.31 mmol) and K$_2$CO$_3$ (98 mg, 0.713 mmol) in DMSO (0.5 mL) was heated at 100° C. for 1 h. After cooling at RT, EtOAc and water were added and the product was extracted in organic phase. The organic phase was dried and evaporated, and the residue was purified by FC on NH column (eluent: DCM to DCM/MeOH 90/10) affording 4-(3-fluorophenoxy)-2-{3H,4H,5H,6H,7H-imidazo[4,5-c]pyridin-5-yl}-6-(trifluoromethyl)pyrimidine (E36, 18 mg, y=15%) as a white solid.

MS (ES) (m/z): 380.11 [M+H]$^+$
$^1$H NMR (DMSO-d$_6$): δ ppm 11.70 (br. s., 1H), 7.61-7.48 (m, 1H), 7.45 (s, 1H), 7.32-7.11 (m, 3H), 6.66 (s, 1H), 4.54 (br. s., 2H), 3.95 (br. s., 2H), 2.63 (br. s., 2H)

Preparation 53: 1-benzyl-6-[4-(3-fluorophenoxy)-6-(trifluoromethyl)pyrimidin-2-yl]-decahydro-1,6-naphthyridine (P53)

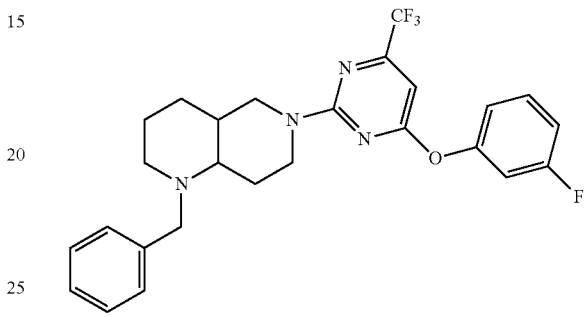

In a close vessel a mixture of 1-benzyl-decahydro-1,6-naphthyridine (51 mg, 0.22 mmol), 2-chloro-4-(3-fluorophenoxy)-6-(trifluoromethyl)pyrimidine (P2, 65 mg, 0.22 mmol) and K$_2$CO$_3$ (39 mg, 0.29 mmol) in DMSO (0.9 mL) was heated at 90° C. and shaken 1.5 h at this temperature. After cooling at RT, EA and water were added, the organic phase was washed with water, dried and evaporated; crude product was purified by FC on NH column (eluent: Cy to Cy/EA 90/10) affording 1-benzyl-6-[4-(3-fluorophenoxy)-6-(trifluoromethyl)pyrimidin-2-yl]-decahydro-1,6-naphthyridine (P53, 56 mg, y=52%)

MS (ES) (m/z): 487.2 [M+H]$^+$.

Example 39

6-[4-(3-fluorophenoxy)-6-(trifluoromethyl)pyrimidin-2-yl]-decahydro-1,6-naphthyridine hydrochloride (E39)

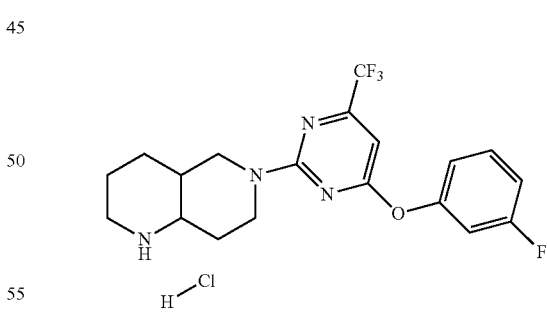

Step a

To a solution of 1-benzyl-6-[4-(3-fluorophenoxy)-6-(trifluoromethyl)pyrimidin-2-yl]-decahydro-1,6-naphthyridine (P53, 56 mg, 0.11 mmol) in MeOH (3.5 mL), HCOONH$_4$ (44 mg) and 10% Pd/C (15 mg) were added at RT then the mixture was stirred under reflux. After 1.5 h the reaction mixture was filtered on celite and the solvent removed under vacuum. The residue was dissolved in DCM, the organic solution washed with water twice, dried over Na$_2$SO$_4$ and the solvent removed under reduced pressure to give a crude material which was purified by FC on NH cartridge (eluent:

Cy to Cy/EA 60/40) to give 6-[4-(3-fluorophenoxy)-6-(trifluoromethyl)pyrimidin-2-yl]-decahydro-1,6-naphthyridine (24 mg)

Step b

6-[4-(3-fluorophenoxy)-6-(trifluoromethyl)pyrimidin-2-yl]-decahydro-1,6-naphthyridine (from step a, 24 mg,) was dissolved in DCM (0.1 mL) and 2N HCl (0.031 mL) was added. The mixture was concentrated under reduced pressure, the residue was triturated with ether and dried under vacuum to give 6-[4-(3-fluorophenoxy)-6-(trifluoromethyl)pyrimidin-2-yl]-decahydro-1,6-naphthyridine hydrochloride (E39, 24 mg, y=46%)

MS (ES) (m/z): 397.17 [M+H]$^+$.

$^1$H NMR (DMSO-d$_6$): δ ppm 9.29 (br. s., 1 H), 9.04 (br. s., 1 H), 7.59-7.43 (m, 1 H), 7.33-7.03 (m, 3H), 6.76-6.64 (m, 1 H), 4.76-3.15 (m, 6H), 3.10-2.81 (m, 2 H), 2.17-1.05 (m, 6 H)

Biological Methods

The ability of the compounds of formula I to inhibit dopamine transporters may be determined using the following biological assays:

Measure of Affinity to the Human Transporters DAT, NET and SERT

The affinities of the compounds of the invention for the human dopamine transporter (DAT), human norepinephrine transporter (NET) and for the human serotonin transporter (SERT) may be determined by the assays described below. Affinity is expressed in terms of inhibition constant (Ki) of the compounds of the invention for DAT, NET and SERT, and it is typically calculated from the IC$_{50}$ values obtained in competition experiments using Cheng and Prusoff equation (Cheng and Prusoff, *Biochem. Pharmacol.* 22:3099, 1973). In the context of the present invention pKi values (corresponding to the antilogarithm of Ki) are used instead of Ki; pKi are only estimated to be accurate to about 0.3 log unit.

Scintillation Proximity Assay (SPA) for Human DAT, NET and SERT Binding a) Membrane Preparation Chinese Hamster Ovary (CHO) cells stably expressing either human DAT (hDAT-CHO) or human NET (hNET-CHO) or human SERT (hSERT-CHO) are used for the membrane preparations for radioligand binding assays using Scintillation proximity Assay (SPA) technique. Each cell line is cultured independently in F-12K Nutrient Mixture containing 10% of Fetal Bovine Serum (FBS) supplemented with 450 µg/ml G-418. When cells are at 70-80% of confluence 3 mM Na Butyrate was added to the cell culture medium. After 24 h of incubation, the culture medium was removed and the cells detached with Versene (DAT) or by scraping (NET and SERT). Cell suspension is centrifuged at 41,000 g for 10 minutes at 4° C. The resultant pellets are re-suspended in 15 volumes of Ice-cold buffer (20 mM HEPES, 145 mM NaCl, 5 mM KCl, pH7.3), homogenized using an Ultra Turrax homogeniser and centrifuged as before. The resultant membrane pellets are re-suspended in up to 15 volume of ice-cold buffer, incubated for 20 minutes at 37° C and centrifuged as before at 41,000 g. The final membrane pellets are re-suspended into 5-10 volumes of ice-cold buffer, dispensed into 0.5 ml aliquots and stored at −80° C. until use. Protein concentration for each preparation is determined using Bio-Rad Protein Assay Kit.

b) Competition Binding Experiments Using Scintillation Proximity Assay (SPA) for Human DAT, NET and SERT The affinity of the compounds of the invention to the human DAT or NET or SERT transporters is assessed by using the [$^3$H]WIN-35,428 or [$^3$H]nisoxetine or [$^3$H]citalopram binding assays in recombinant human DAT, NET and SERT membranes with the SPA technology. The final assay volume is 50 µL in 384 well plates.

Briefly, 0.5 µL of test compound in neat DMSO or 0.5 µL of DMSO for total binding (TB) or 0.5 µL of indatraline 1 mM (10 µM final concentration) for non specific binding (NSB) are added to the assay plate. 50 µL of the SPA mixture is added to each well, containing: 30 µg/mL or 10 µg/mL or 25 µg/mL DAT, NET, SERT membranes, respectively; 5 nM [$^3$H]WIN-35,428 or 5 nM [$^3$H]nisoxetine or 1 nM [$^3$H]citalopram, for DAT, NET, SERT assay, respectively; 2.5 mg/mL or 1 mg/mL or 4 mg/mL WGA-PVT SPA beads (PerkinElmer RPNQ0001, for DAT, NET, SERT assay, respectively). All components are added to Assay Buffer (20 mM HEPES pH 7.4, 145 mM NaCl, 5 mM KCl, 0.01% Pluronic F-127). 0.02% BSA was used for DAT binding only. Plates are sealed with Topseal A and centrifuged 1 min, 800 rpm. Plates are loaded into a 1450 Microbeta TriLux (Perkin-Elmer) plate reader and the radioactivity counted after at least 4 hrs or overnight incubation at room temperature. Curve fitting and IC$_{50}$ estimations are performed using a four parameter model in XLfit (IDBS, Guilford, UK) for Microdoft Excel (Microsoft, Redmond, Wash.).

Uptake Functional Assay on hDAT-CHO Cells

The potency of the compounds of the invention in blocking the DAT function is measured using an uptake assay in a recombinant CHO cell line expressing human DAT (hDAT-CHO). Potency is measured in terms of pIC$_{50}$ by testing the compounds of invention for the inhibition of [$^3$H]-dopamine uptake in DAT-CHO cells using a SPA technology in 384 well format.

Briefly, on the days of the experiment hDAT-CHO cells are detached using Versene and added (75,000 cells/mL) to the SPA Mixture, which contains the following components in Assay Buffer (20 mM HEPES, 145 mM NaCl, 5 mM KCl, 2 mM CaCl$_2$, 1 mM MgCl$_2$ and 1 g/L glucose, pH 7.3): 0.02% w/v of Pluronic F127, 2 mg/mL SPA Imaging beads (RPNQ0260, PerkinElmer), 10 µM pargyline and 80 nM of [$^3$H]-dopamine. The SPA Mixture is added 50 µl/well to 384 well plates containing 0.5 µL/well of test compound in neat DMSO or 0.5 µL of DMSO (control uptake) or 0.5 µL of the standard inhibitor indatraline (at 10 µM final in the assay). Plates are sealed with a Top-seal A and read using Viewlux instrument (Perkin-Elmer) at 15-30 min time intervals. The first highest signal is used for data analysis.

Measure of the Effect on hERG Channel by Tail Current Recording Using In Vitro Rapid ICE™

The potency of the compounds of the invention in inhibiting human ERG potassium channel (hERG) tail current is assessed in a recombinant HEK293 cell line stably transfected with hERG cDNA using Rapid ICE™ (Rapid Ion Channel Electrophysiology) assay. Rapid ICE™ is an automated patch-clamp assay utilizing the PatchXpress 7000A system (Molecular Devices Corporation) or the QPatch HTX system (Sophion Bioscience A/S).

Briefly cells are cultivated for 24 to 72 hours before recordings in minimum essential medium supplemented with 10% FBS, 1% non-essential amino acids, 1% sodium pyruvate, 2 mM L-glutamine. The day of the experiment cells are detached with TrypLE and prepared to be loaded on the instrument. For PatchXpress cells are finally resuspended in 150 µl of Extracellular Buffer whereas for QPatch cells are resuspended in 7 ml Serum-Free Media containing 25 mM Hepes and Soybean trypsin inhibitor and immediately placed in the cell storage tank of the machine. The composition of the Extracellular Buffer is (mM): NaCl 137; KCl 4; CaCl2 1.8; MgCl2 1.0; D-glucose 10; N 2 hydroxyethylpiperazine-N'-2-ethanesulfonic acid (HEPES) 10; pH 7.4 with 1 M NaOH. The composition of the pipette solution is (mM): KCl 130; MgCl2 1.0; Ethylene glycol-bis(β-aminoethyl ether)-N,N,N',N'-tetraacetic acid (EGTA) 5; MgATP 5; HEPES 10; pH 7.2 with 1 M KOH. The voltage protocol includes the following steps: step from −80 mV to −50 mV for 200 ms, +20 mV for 4.8 s, step to −50 mV for 5 s then step to the holding potential of −80 mV. Compounds of the invention are dissolved in DMSO and diluted in Extracellular Buffer to achieve final test concentrations (0.1, 1 and 10 μM) in 0.1% DMSO. The voltage protocol is run and recorded continuously during the experiment. The vehicle, corresponding to 0.1% DMSO in Extracellular Buffer, is then applied for 3 min followed by the test substance in triplicate. The standard combined exposure time is 5 min. The average of tail current amplitude values recorded from 4 sequential voltage pulses is used to calculate for each cell the effect of the test substance by calculating the residual current (% control) compared with vehicle pre-treatment. Data are reported as % inhibition for each concentration tested and $IC_{50}$ values are estimated using DataXpress or QPatch software. At least two cells are tested, more if results diverge.

Representative compounds of the present invention were tested according to the procedure described above, with results as listed in Table 1 below.

TABLE 1

| Example | $pIC_{50}$ | | | |
| --- | --- | --- | --- | --- |
| | DAT | NET | SERT | hERG |
| 1 | 8.46 | 7.00 | 4.87 | 6.6 |
| 2 | 8.80 | 7.57 | 4.77 | 6.7 |
| 3 | 8.13 | 6.42 | 4.67 | 6.0 |
| 4 | 7.38 | 6.19 | <4 | 6.1 |
| 5 | 8.33 | 6.61 | 4.63 | 5.7 |
| 6 | 6.89 | 5.94 | 4.49 | <5 |
| 7 | 8.06 | 6.53 | 5.53 | 5.8 |
| 8 | 7.66 | 6.29 | 5.22 | 6.8 |
| 9 | 7.91 | 6.02 | 4.95 | — |
| 10 | 7.18 | 5.33 | <4 | — |
| 11 | 8.72 | 6.46 | 5.12 | 5.8 |
| 12 | 8.56 | 6.84 | 5.06 | — |
| 13 | 8.31 | 6.40 | 5.14 | 5.4 |
| 14 | 8.82 | 6.93 | 6.22 | — |
| 15 | 9.04 | 7.24 | 6.18 | — |
| 16 | 7.81 | 6.01 | 5.84 | — |
| 17 | 8.17 | 6.49 | 5.68 | — |
| 18 | 9.05 | 7.51 | 5.21 | 6.0 |
| 19 | 8.02 | 6.10 | 6.44 | 6.1 |
| 20 | 8.39 | 6.50 | 5.29 | — |
| 21 | 7.84 | 4.75 | <4 | <5 |
| 22 | 7.58 | 5.76 | <4 | — |
| 23 | 7.75 | 5.55 | <4 | — |
| 24 | 7.42 | 5.04 | <4 | — |
| 25 | 8.30 | 5.70 | 4.45 | <5 |
| 26 | 7.65 | <4 | <4 | 5.5 |
| 27 | 7.72 | 5.65 | 4.46 | 5.3 |
| 28 | 7.86 | 5.96 | <4 | 5.5 |
| 29 | 8.22 | 5.77 | 4.72 | 5.4 |
| 30 | 8.72 | 6.78 | 4.46 | — |
| 31, 32 | 8.75 | 6.86 | 4.46 | 5.7 |
| | 8.47 | 6.63 | 4.36 | — |
| 33 | 8.86 | 6.52 | 4.72 | 5.8 |
| 34 | 6.50 | 4.72 | <4 | — |
| 35 | 8.25 | 6.56 | 4.48 | — |
| 36 | 7.90 | 6.01 | <4 | 5.6 |
| 39 | 8.90 | 7.51 | 5.52 | 6.2 |

While the foregoing specification teaches the principles of the present invention, with examples provided for the purpose of illustration, it will be understood that the practice of the invention encompasses all of the usual variations, adaptations and/or modifications as come within the scope of the following claims.

REFERENCES

1 Wise R A, Annu Rev Neurosci. 1996; 19: 319-340
2 Cohen N J et al., Psychopharmacologia. 1971; 22(3): 282-294
3 Leibowitz S F et al., Brain Res Bull. 1986; 17(5): 681-689.
4 Hartmann E et al., Psychopharmacology (Berl). 1976 10; 50(2): 171-175
5 Lader M H, J Clin Psychiatry. 1996; 57 Suppl 2: 39-44
6 Montejo-Gonzalez A L et al., J Sex Marital Ther. 1997; 23(3): 176-194
7 Olfson M et al., Arch Gen Psychiatry. 2006 August; 63(8): 865-872
8 Dworkin N, J Am Acad Child Adolesc Psychiatry. 2005; 44(6): 510
9 Denolle T et al., Clin Pharmacol Ther. 1999; 66(3): 282-287
10 Nieoullon A, Prog Neurobiol. 2002; 67(1): 53-83
11 Cornish R S et al., Pharm Res. 2005; 22(4): 603-612
12 Cook E H Jr et al., Am J Hum Genet. 1995; 56(4): 993-998
13 Van Gaalen M M et al., Biol Psychiatry. 2006; 60(1): 66-73
14 Yoon et al., J Neurol Sci. 2007; 255(1-2): 50-56
15 Cheon et al., Psychiatry Res. 2004; 130(1): 85-95
16 Kim C H et al., Eur J Nucl Med Mol Imaging. 2003; 30(12): 1637-1643
17 Grigorenko E L et al., Aggress Behav. 2010; 36(3): 158-176
18 Amsterdam et al., J Affect Disord. 2012; 141(2-3): 425-431
19 Hsiao et al., Psychiatry Res. 2013; 211(1): 72-77
20 Baldwin D S et al., Br J Psychiatry. 2013; 202: 396-397
21 Abler B et al., Neuropsychopharmacology. 2011; 36(9): 1837-1847
22 Segman et al., Mol Psychiatry. 2002; 7(8): 903-7
23 Devos D et al., J Neurol Neurosurg Psychiatry. 2007; 78(5): 470-475
24 Espay et al., Neurology. 2011; 76(14): 1256-1262
25 Auriel et al., Clin Neuropharmacol. 2006; 29(1): 15-17
26 Baumann M H et al., J Pharmacol Exp Ther. 1994; 271(3): 1216-1222
27 Rothman R B et al., Pharmacol Biochem Behav. 1991; 40(2): 387-397
28 Wang G J et al., Obesity (Silver Spring) 2011; 19(8): 1601-1608
29 Michaelides M et al., Int Rev Psychiatry. 2012; 24(3): 211-218
30 Bello et al., Brain Res Bull. 2006; 70(4-6): 422-429
31 Shinohara M et al., J Psychiatry Neurosci. 2004; 29(2): 134-137
32 Slama et al., Diabete Metab. 1978; 4(3): 193-199
33 Remy P et al., Curr Opin Neurol. 2003; 16 Suppl 2: S37-41
34 Berrios G E, Compr Psychiatry 1990; 31(2): 140-151
35 Harris J D, Curr Opin Support Palliat Care 2008; 2(3): 180-186
36 Lacerda et al., J Cardiovasc Electrophysiol. 2010; 21(3): 301-310
37 Campbell V C et al., J Pharmacol Exp Ther. 2005; 315(2): 631-640
38 Zou M F et al., J Med Chem. 2006; 49(21): 6391-6399
39 Li S M et al., J Pharmacol Exp Ther. 2011; 336(2): 575-585

The invention claimed is:
1. A compound according to formula I,

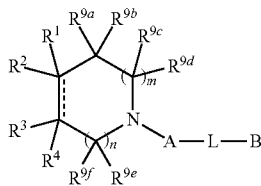

wherein:
A is selected from phenyl and heteroaryl;
B is selected from phenyl and heteroaryl;
L is a linker selected from alkylene and O;
$R^1$ is selected from H, alkyl, alkoxy, S-alkyl, $S(O)_q$alkyl, $COR^5$, $CONR^5R^6$, $COOR^5$, $CH_2OH$, OH, F and Cl;
$R^2$ is selected from $NR^7R^8$, $CR^{11}R^{12}NR^7R^8$, $CONR^7R^8$, $(CR^{11}R^{12})_2NR^7R^8$ and $(CR^{11}R^{12})_3NR^7R^8$, wherein $R^1$ is alkyl, alkoxy, $CH_2OH$, $COR^5$, $CONR^5R^6$ or $COOR^5$ when $R^2$ is $NR^7R^8$;
$R^3$ is selected from H, alkyl, alkoxy, $NR^7R^8$, $CH_2OH$, OH, F and Cl;
or $R^2$ and $R^3$ come together with the carbon atoms to which they are attached to form heterocyclyl or heteroaryl, wherein the heterocyclyl or heteroaryl contains at least one ring member selected from N and $NR^{13}$; provided that when $R^2$ and $R^3$ come together with the carbon atoms to which they are attached to form heterocyclyl or heteroaryl, L is O;
provided that when $R^1$ is H, either
$R^2$ and $R^3$ come together with the carbon atoms to which they are attached to form heterocyclyl; or
$R^3$ is selected from alkyl, alkoxy, $NR^7R^8$, $CH_2OH$, OH, F and Cl;
$R^4$, $R^5$ and $R^6$ are each independently selected from H and alkyl;
$R^7$ and $R^8$ are independently selected from H, alkyl, cycloalkyl, heterocyclyl, and $C(O)R^{10}$, wherein when $R^7$ is $C(O)R^{10}$, $R^8$ is H or alkyl; or $R^7$ and $R^8$ may come together with the nitrogen atom to which they are attached to form heterocyclyl;
$R^{9a}$, $R^{9b}$, $R^{9c}$, $R^{9d}$, $R^{9e}$ and $R^{9f}$ are independently selected from H and alkyl;
$R^{10}$ is selected from alkyl, aryl, heterocyclyl and heteroaryl;
---- is absent or represents a bond, wherein when ---- is a bond le and $R^4$ are absent;
m is 0, 1 or 2, wherein when m is 2, n is 0;
n is 0, 1 or 2, wherein when n is 2, m is 0;
q is 1 or 2;
alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1, 2, 3, 4 or 5 substituents selected from S-alkyl, S(O)alkyl, $S(O)_2$alkyl, cycloalkyl, heterocyclyl, alkoxy, OH, —CN, $CF_3$, $COOR^{13}$, $CONR^{13}R^{14}$, F, Cl, $NR^{13} COR^{14}$ and $NR^{13} R^{14}$;
cycloalkyl is a monocyclic saturated hydrocarbon of between 3 and 7 carbon atoms ($C_3$-$C_7$);
cycloalkyl may optionally be substituted with 1, 2, 3, 4 or 5 substituents independently selected from S-alkyl, S(O)alkyl, $S(O)_2$alkyl, alkyl, alkoxy, OH, —CN, $CF_3$, $COOR^{13}$, $CONR^{13}R^{14}$, F, Cl, and $NR^{13}R^{14}$;
phenyl may be optionally substituted with 1, 2 or 3 substituents independently selected from alkyl, cycloalkyl, heterocyclyl, alkoxy, S-alkyl, S(O)alkyl, $S(O)_2$alkyl, OH, F, Cl, —CN, $OCF_3$, $CF_3$, $NR^{13}COR^{14}$ and $NR^{13}R^{14}$;
alkylene is a bivalent $C_{1-3}$ straight-chained alkyl radical or a bivalent $C_{3-4}$ branched alkyl radical, wherein alkylene may optionally be substituted with 1 or 2 substituents selected from S-alkyl, S(O)alkyl, $S(O)_2$alkyl, heterocyclyl, alkoxy, OH, —CN, $CF_3$, $COOR^{13}$, $CONR^{13}R^{14}$, F, Cl, $NR^{13}COR^{14}$ and $NR^{13}R^{14}$;
heterocyclyl is a monocyclic ring which is saturated or partially unsaturated, containing, where possible, 1 or 2 ring members independently selected from N, S, O and $NR^{13}$ and 2 to 5 carbon atoms; heterocyclyl may optionally be substituted with 1,2 or 3 substituents independently selected from alkyl, cycloalkyl, alkoxy, S-alkyl, S(O)alkyl, $S(O)_2$alkyl, oxo, OH, F, Cl, —CN, $OCF_3$, $CF_3$, $NR^{13}COR^{14}$ and $NR^{13}R^{14}$;
heteroaryl is a 5 or 6 membered aromatic ring, containing, where possible, 1, 2 or 3 ring members independently selected from N, $NR^{13}$, S and O; heteroaryl may be optionally substituted with 1, 2 or 3 substituents independently selected from alkyl, cycloalkyl, heterocyclyl, alkoxy, S-alkyl, S(O)alkyl, $S(O)_2$alkyl, OH, F, Cl, —CN, $OCF_3$, $CF_3$, $NR^{13}COR^{14}$ and $NR^{13}R^{14}$;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1, 2, 3, 4 or 5 substituents independently selected from S-alkyl, S(O)alkyl, $S(O)_2$alkyl, alkyl, OH, —CN, $CF_3$, $COOR^{13}$, $CONR^{13}R^{14}$, F, Cl, $NR^{13}COR^{14}$ and $NR^{13}R^{14}$;
$R^{11}$, $R^{12}$, $R^{13}$ and $R^{14}$ are independently selected from H and alkyl;
and tautomers, stereoisomers, pharmaceutically acceptable salts and solvates thereof;
wherein the compound of formula I is not:

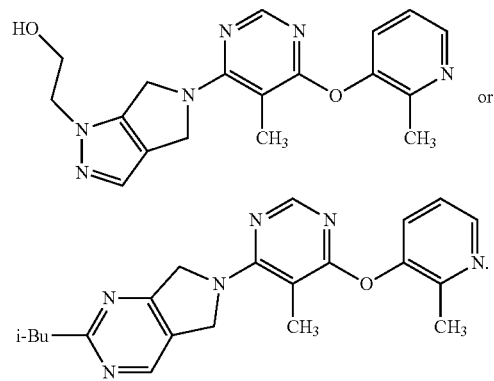

2. The compound of claim 1 wherein when $R^2$ and $R^3$ come together with the carbon atoms to which they are attached to form heterocyclyl or heteroaryl, the sum of m and n is 2.

3. The compound of claim 1 wherein:
$R^1$ is selected from alkyl, alkoxy, S-alkyl, $S(O)_q$alkyl, $COR^5$, $CONR^5R^6$, $COOR^5$, $CH_2OH$, OH, F and Cl;
$R^2$ is selected from $NR^7R^8$, $CONR^7R^8$, $CR^{11}R^{12}NR^7R^8$, $(CR^{11}R^{12})_2NR^7R^8$ and $(CR^{11}R^{12})_3NR^7R^8$;
$R^3$ is selected from H and alkyl;
$R^4$, $R^5$ and $R^6$ are each independently selected from H and alkyl;
---- is absent.

4. The compound of claim 1 wherein n is 1 and m is 0 or 1.

5. The compound of claim 1 wherein $R^{9a}$, $R^{9b}$, $R^{9c}$, $R^{9d}$, $R^{9e}$, $R^{9f}$, $R^{11}$ and $R^{12}$ are all H.

6. The compound of claim 1, according to formula IA,

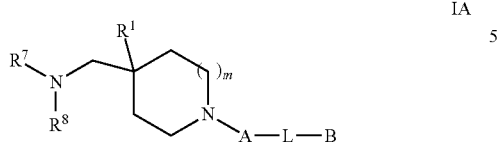

wherein:
A is selected from phenyl and heteroaryl;
B is selected from phenyl and heteroaryl;
L is a linker selected from alkylene and O;
$R^1$ is selected from $CH_2OH$, OH, F and Cl;
$R^7$ and $R^8$ are independently selected from H, alkyl, cycloalkyl, heterocyclyl, and $C(O)R^{10}$, wherein when $R^7$ is $C(O)R^{10}$, $R^8$ is H or alkyl; or $R^7$ and $R^8$ may come together with the nitrogen atom to which they are attached to form heterocyclyl;
$R^{10}$ is selected from alkyl, aryl, heterocyclyl and heteroaryl;
m is 0 or 1;
alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1, 2, 3, 4 or 5 substituents selected from cycloalkyl, heterocyclyl, S-alkyl, S(O)alkyl, S(O)$_2$alkyl, alkoxy, OH, —CN, $CF_3$, $COOR^{13}$, $CONR^{13}R^{14}$, F, Cl $NR^{13}COR^{14}$ and $NR^{13}R^{14}$,
cycloalkyl is a monocyclic saturated hydrocarbon of between 3 and 7 carbon atoms ($C_3$-$C_7$);
cycloalkyl may optionally be substituted with 1, 2, 3, 4 or 5 substituents independently selected from S-alkyl, S(O)alkyl, S(O)$_2$alkyl, alkyl, alkoxy, OH, —CN, $CF_3$, $COOR^{13}$, $CONR^{13}R^{14}$, F, Cl, $NR^{13}COR^{14}$ and $NR^{13}R^{14}$;
phenyl may be optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, $OCF_3$, $CF_3$, $NR^{13}COR^{14}$ and $NR^{13}R^{14}$;
heterocyclyl is a monocyclic ring which is saturated or partially unsaturated, containing, where possible, 1 or 2 ring members independently selected from N, S, O and NH and 2 to 5 carbon atoms; heterocyclyl may optionally be substituted with 1, 2 or 3 substituents independently selected from alkyl, cycloalkyl, alkoxy, S-alkyl, S(O)alkyl, S(O)$_2$alkyl, oxo, OH, F, Cl, —CN, $OCF_3$, $CF_3$, $NR^{13}COR^{14}$ and $NR^{13}R^{14}$;
heteroaryl is a 5 or 6 membered aromatic ring, containing, where possible, 1, 2 or 3 ring members independently selected from N, $NR^{13}$, S and O; heteroaryl may be optionally substituted with 1, 2 or 3 substituents independently selected from alkyl, cycloalkyl, alkoxy, S-alkyl, S(O)alkyl, S(O)$_2$alkyl, OH, F, Cl, —CN, $OCF_3$, $CF_3$, $NR^{13}COR^{14}$ and $NR^{13}R^{14}$;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1, 2, 3, 4 or 5 substituents independently selected from S-alkyl, S(O)alkyl, S(O)$_2$alkyl, alkyl, OH, —CN, $CF_3$, $COOR^{13}$, $CONR^{13}R^{14}$, F, Cl, $NR^{13}COR^{14}$ and $NR^{13}R^{14}$;

$R^{13}$ and $R^{14}$ are independently selected from H and alkyl;
and tautomers, stereoisomers, pharmaceutically acceptable salts and solvates thereof.

7. The compound of claim 6 wherein m is 1.

8. The compound of claim 1 wherein $R^1$ is OH.

9. The compound of claim 1 wherein L is O.

10. The compound of claim 1 wherein A is phenyl, pyridyl or pyrimidinyl, optionally substituted with 1, 2 or 3 substituents independently selected from alkyl, cycloalkyl, heterocyclyl, alkoxy, S-alkyl, S(O)alkyl, S(O)$_2$alkyl, OH, F, Cl, —CN, $OCF_3$, $CF_3$, $NR^{13}COR^{14}$ and $NR^{13}R^{14}$.

11. The compound of claim 1 wherein A is phenyl, 2-pyridyl or 1,3-pyrimidinyl, optionally substituted with 1, 2 or 3 substituents independently selected from alkyl, F, Cl, —CN and $CF_3$.

12. The compound of claim 1 wherein A is selected from the group consisting of:

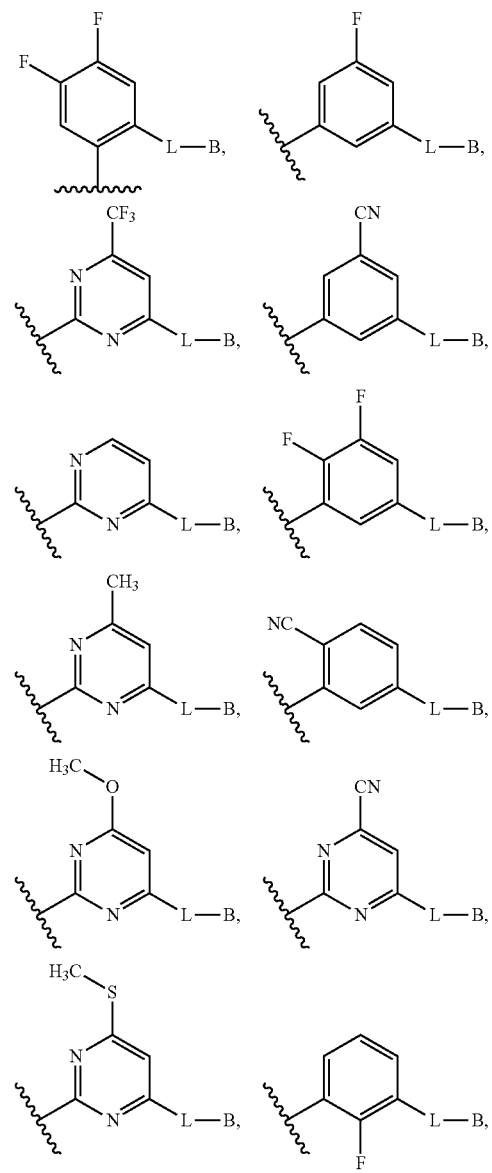

-continued

[chemical structures with L—B substituents]

13. The compound of claim 1 wherein B is phenyl, optionally substituted with 1, 2 or 3 substituents independently selected from alkyl, cycloalkyl, heterocyclyl, alkoxy, S-alkyl, S(O)alkyl, S(O)₂alkyl, OH, F, Cl, —CN, OCF₃, CF₃, NR$^{13}$COR$^{14}$ and NR$^{13}$R$^{14}$.

14. The compound of claim 1 wherein B is selected from the group consisting of:

[chemical structures]

15. A compound of claim 1 selected from:
4-[(dimethylamino)methyl]-1-[4-(3-fluorophenoxy)-6-(trifluoromethyl)pyrimidin-2-yl]piperidin-4-ol;
1-[4-(3-fluorophenoxy)-6-(trifluoromethyl)pyrimidin-2-yl]-4-(pyrrolidin-1-ylmethyl)piperidin-4-ol;
4-[(cyclopropylamino)methyl]-1-[4-(3-fluorophenoxy)-6-(trifluoromethyl)pyrimidin-2-yl]piperidin-4-ol;
4-{[cyclopropyl(methyl)amino]methyl}-1-[4-(3-fluorophenoxy)-6-(trifluoromethyl)pyrimidin-2-yl]piperidin-4-ol;
1-[4-(3-fluorophenoxy)-6-(trifluoromethyl)pyrimidin-2-yl]-4-[(methylamino)methyl]piperidin-4-ol;
4-[(3,3-difluoropyrrolidin-1-yl)methyl]-1-[4-(3-fluorophenoxy)-6-(trifluoromethyl)pyrimidin-2-yl]piperidin-4-ol;
4-(1,4-diazepan-1-ylmethyl)-1-[4-(3-fluorophenoxy)-6-(trifluoromethyl)pyrimidin-2-yl]piperidin-4-ol;
4-[(2, 5-dimethylpyrrolidin-1-yl)methyl]-1-[4-(3-fluorophenoxy)-6-(trifluoromethyl)pyrimidin-2-yl]piperidin-4-ol;
4-[(tert-butylamino)methyl]-1-[4-(3-fluorophenoxy)-6-(trifluoromethyl)pyrimidin-2-yl]piperidin-4-ol;
1-({1-[4-(3-fluorophenoxy)-6-(trifluoromethyl)pyrimidin-2-yl]-4-hydroxypiperidin-4-yl}methyl)pyrrolidin-2-one;
4-(aminomethyl)-1-[4-(3-fluorophenoxy)-6-(trifluoromethyl)pyrimidin-2-yl]piperidin-4-ol;
{4-fluoro-1-[4-(3-fluorophenoxy)-6-(trifluoromethyl)pyrimidin-2-yl]piperidin-4-yl}methanamine;
4-(aminomethyl)-1-[3-fluoro-5-(3-fluorophenoxy)phenyl]piperidin-4-ol;
4-(aminomethyl)-1-[2,5-difluoro-3-(3-fluorophenoxy)phenyl]piperidin-4-ol;
4-(aminomethyl)-1-(2-fluoro-3-phenoxyphenyl)piperidin-4-ol;
4-(aminomethyl)-1-[2-fluoro-3-(3-fluorophenoxy)phenyl]piperidin-4-ol;
4-(aminomethyl)-1-[2,3-difluoro-5-(3-fluorophenoxy)phenyl]piperidin-4-ol;
4-(aminomethyl)-1-[3,4-difluoro-5-(3-fluorophenoxy)phenyl]piperidin-4-ol;
{4-amino-1-[4-(3-fluorophenoxy)-6-(trifluoromethyl)pyrimidin-2-yl]piperidin-4-yl}methanol;
N-({1-[4-(3-fluorophenoxy)-6-(trifluoromethyl)pyrimidin-2-yl]-4-hydroxypiperidin-4-yl}methyl)-2-methylpropanamide;
2-cyclopropyl-N-({1-[4-(3-fluorophenoxy)-6-(trifluoromethyl)pyrimidin-2-yl]-4-hydroxypiperidin-4-yl}methyl)acetamide;
N-({1-[4-(3-fluorophenoxy)-6-(trifluoromethyl)pyrimidin-2-yl]-4-hydroxypiperidin-4-yl}methyl)-2-(propan-2-yloxy)acetamide;
N-({1-[4-(3-fluorophenoxy)-6-(trifluoromethyl)pyrimidin-2-yl]-4-hydroxypiperidin-4-yl}methyl)acetamide;
N-({1-[4-(3-fluorophenoxy)-6-(trifluoromethyl)pyrimidin-2-yl]-4-hydroxypiperidin-4-yl}methyl)azetidine-3-carboxamide;
N-({1-[4-(3-fluorophenoxy)-6-(trifluoromethyl)pyrimidin-2-yl]-4-hydroxypiperidin-4-yl}methyl)benzamide;
N-({1-[4-(3-fluorophenoxy)-6-(trifluoromethyl)pyrimidin-2-yl]-4-hydroxypiperidin-4-yl}methyl)-1H-pyrazole-4-carboxamide;
N-({1-[4-(3-fluorophenoxy)-6-(trifluoromethyl)pyrimidin-2-yl]-4-hydroxypiperidin-4-yl}methyl)pyrazine-2-carboxamide;
2-amino-N-({1-[4-(3-fluorophenoxy)-6-(trifluoromethyl)pyrimidin-2-yl]-4-hydroxypiperidin-4-yl}methyl)acetamide;
3-[(cyclopropylamino)methyl]-1-[4-(3-fluorophenoxy)-6-(trifluoromethyl)pyrimidin-2-yl]pyrrolidin-3-ol;
(3 S)-3-[(cyclopropylamino)methyl]-1-[4-(3-fluorophenoxy)-6-(trifluoromethyl)pyrimidin-2-yl]pyrrolidin-3-ol;
(3R)-3-[(cyclopropylamino)methyl]-1-[4-(3-fluorophenoxy)-6-(trifluoromethyl)pyrimidin-2-yl]pyrrolidin-3-ol;
3-(aminomethyl)-1-[4-(3-fluorophenoxy)-6-(trifluoromethyl)pyrimidin-2-yl]pyrrolidin-3-ol;

N-({1-[4-(3-fluorophenoxy)-6-(trifluoromethyl)pyrimidin-2-yl]-3-hydroxypyrrolidin-3-yl}methyl)-2-methylpropanamide;
N-({1-[4-(3-fluorophenoxy)-6-(trifluoromethyl)pyrimidin-2-yl]-3-hydroxypyrrolidin-3-yl}methyl)azetidine-3-carboxamide;
4-(3-fluorophenoxy)-2-{3H,4H,5H,6H,7H-imidazo[4,5-c]pyridin-5-yl}-6-(trifluoromethyl)pyrimidine;
6-[4-(3-fluorophenoxy)-6-(trifluoromethyl)pyrimidin-2-yl]-decahydro-1,6-naphthyridine;
and pharmaceutically acceptable salts and solvates thereof.

16. A compound of claim 15 selected from:
4-[(cyclopropylamino)methyl]-1-[4-(3-fluorophenoxy)-6-(trifluoromethyl)pyrimidin-2-yl]piperidin-4-ol;
1-[4-(3-fluorophenoxy)-6-(trifluoromethyl)pyrimidin-2-yl]-4-[(methylamino)methyl]piperidin-4-ol;
4-(1,4-diazepan-1-ylmethyl)-1-[4-(3-fluorophenoxy)-6-(trifluoromethyl)pyrimidin-2-yl]piperidin-4-ol;
4-[(tert-butylamino)methyl]-1-[4-(3-fluorophenoxy)-6-(trifluoromethyl)pyrimidin-2-yl]piperidin-4-ol;
4-(aminomethyl)-1-[4-(3-fluorophenoxy)-6-(trifluoromethyl)pyrimidin-2-yl]piperidin-4-ol;
{4-fluoro-1-[4-(3-fluorophenoxy)-6-(trifluoromethyl)pyrimidin-2-yl]piperidin-4-yl}methanamine;
4-(aminomethyl)-1-[3-fluoro-5-(3-fluorophenoxy)phenyl]piperidin-4-ol;
4-(aminomethyl)-1-[2,5-difluoro-3-(3-fluorophenoxy)phenyl]piperidin-4-ol;
4-(aminomethyl)-1-(2-fluoro-3-phenoxyphenyl)piperidin-4-ol;
4-(aminomethyl)-1-[2-fluoro-3-(3-fluorophenoxy)phenyl]piperidin-4-ol;
4-(aminomethyl)-1-[2,3-difluoro-5-(3-fluorophenoxy)phenyl]piperidin-4-ol;
4-(aminomethyl)-1-[3,4-difluoro-5-(3-fluorophenoxy)phenyl]piperidin-4-ol;
{4-amino-1-[4-(3-fluorophenoxy)-6-(trifluoromethyl)pyrimidin-2-yl]piperidin-4-yl}methanol;
N-({1-[4-(3-fluorophenoxy)-6-(trifluoromethyl)pyrimidin-2-yl]-4-hydroxypiperidin-4-yl}methyl)-2-methylpropanamide;
2-cyclopropyl-N-({1-[4-(3-fluorophenoxy)-6-(trifluoromethyl)pyrimidin-2-yl]-4-hydroxypiperidin-4-yl}methyl)acetamide;
N-({1-[4-(3-fluorophenoxy)-6-(trifluoromethyl)pyrimidin-2-yl]-4-hydroxypiperidin-4-yl}methyl)-2-(propan-2-yloxy)acetamide;
N-({1-[4-(3-fluorophenoxy)-6-(trifluoromethyl)pyrimidin-2-yl]-4-hydroxypiperidin-4-yl}methyl)acetamide;
N-({1-[4-(3-fluorophenoxy)-6-(trifluoromethyl)pyrimidin-2-yl]-4-hydroxypiperidin-4-yl}methyl)azetidine-3-carboxamide;
N-({1-[4-(3-fluorophenoxy)-6-(trifluoromethyl)pyrimidin-2-yl]-4-hydroxypiperidin-4-yl}methyl)benzamide;
N-({1-[4-(3-fluorophenoxy)-6-(trifluoromethyl)pyrimidin-2-yl]-4-hydroxypiperidin-4-yl}methyl)-1H-pyrazole-4-carboxamide;
N-({1-[4-(3-fluorophenoxy)-6-(trifluoromethyl)pyrimidin-2-yl]-4-hydroxypiperidin-4-yl}methyl)pyrazine-2-carboxamide;
2-amino-N-({1-[4-(3-fluorophenoxy)-6-(trifluoromethyl)pyrimidin-2-yl]-4-hydroxypiperidin-4-yl}methyl)acetamide;
3-[(cyclopropylamino)methyl]-1-[4-(3-fluorophenoxy)-6-(trifluoromethyl)pyrimidin-2-yl]pyrrolidin-3-ol;
(3S)-3-[(cyclopropylamino)methyl]-1-[4-(3-fluorophenoxy)-6-(trifluoromethyl)pyrimidin-2-yl]pyrrolidin-3-ol;
(3R)-3-[(cyclopropylamino)methyl]-1-[4-(3-fluorophenoxy)-6-(trifluoromethyl)pyrimidin-2-yl]pyrrolidin-3-ol;
3-(aminomethyl)-1-[4-(3-fluorophenoxy)-6-(trifluoromethyl)pyrimidin-2-yl]pyrrolidin-3-ol;
N-({1-[4-(3-fluorophenoxy)-6-(trifluoromethyl)pyrimidin-2-yl]-3-hydroxypyrrolidin-3-yl}methyl)azetidine-3-carboxamide;
4-(3-fluorophenoxy)-2-{3H,4H,5H,6H,7H-imidazo[4,5-c]pyridin-5-yl}-6-(trifluoromethyl)pyrimidine;
and pharmaceutically acceptable salts and solvates thereof.

17. A pharmaceutical composition comprising a compound of claim 1 and a pharmaceutically acceptable excipient.

18. A method of treating a condition, disease or disorder ameliorated by inhibition of a dopamine transporter, wherein said condition, disease or disorder is selected from sexual dysfunction, affective disorders, anxiety, depression, Tourette syndrome, Angelman syndrome, attention deficit disorder (ADD), attention deficit hyperactivity disorder (ADHD), obesity, pain, obsessive-compulsive disorder, movement disorders, CNS disorders, sleep disorders, narcolepsy, conduct disorder, substance abuse, smoking cessation, eating disorders, chronic or persistent fatigue and impulse control disorder, the method comprising administering the compound of claim 1 to a subject in need thereof.

19. The method of claim 18 wherein said condition, disease or disorder is selected from attention deficit disorder (ADD), attention deficit hyperactivity disorder (ADHD), binge-eating disorder, or fatigue associated with a condition selected from the group consisting of chronic fatigue syndrome, post-viral fatigue syndrome, HIV, multiple sclerosis, amyotrophic lateral sclerosis (ALS), myasthenia gravis, sarcoidosis, cancer, chemotherapy treatment, celiac disease, irritable bowel syndrome, spondyloarthropathy, fibromyalgia, arthritis, infectious diseases, diabetes, eating disorders, Parkinson's disease, sleep disorders, stroke, mood disorders, drug abuse and alcohol abuse.

20. The compound of claim 1, wherein the stereoisomers comprise enantiomers, diastereoisomers, or racemic or scalemic mixtures thereof.

21. The compound of claim 6, wherein the stereoisomers comprise enantiomers, diastereoisomers, or racemic or scalemic mixtures thereof.

* * * * *

UNITED STATES PATENT AND TRADEMARK OFFICE
CERTIFICATE OF CORRECTION

PATENT NO. : 9,920,053 B2
APPLICATION NO. : 15/511515
DATED : March 20, 2018
INVENTOR(S) : Susanna Cremonesi et al.

Page 1 of 1

It is certified that error appears in the above-identified patent and that said Letters Patent is hereby corrected as shown below:

In the Claims

Column 97 in Claim 1, Line 5, please delete "S(O)$_q$ alkyl" and insert -- S(O)$_q$ alkyl -- therefore.

Column 97 in Claim 1, Line 32, please delete "R$^{9a}$, R$^{9b}$, R$^{9c}$, R$^{9d}$, R$^{9e}$ and R$^{9f}$" and insert -- R$^{9a}$, R$^{9b}$, R$^{9c}$, R$^{9d}$, R$^{9e}$ and R$^{9f}$ -- therefore.

Column 97 in Claim 1, Line 37, please delete "1e and R$^4$ are absent" and insert -- R$^1$ and R$^4$ are absent -- therefore.

Column 97 in Claim 1, Line 47, please delete "NR$^{13}$ COR$^{14}$" and insert -- NR$^{13}$COR$^{14}$ -- therefore.

Column 98 in Claim 3, Line 63, please delete "_ _ _ _ is absent" and insert -- - - - - is absent -- therefore.

Column 98 in Claim 6, Line 32, please delete "NR$^{13}$R$^{14}$," and insert -- NR$^{13}$R$^{14}$; -- therefore.

Column 102 in Claim 15, Line 6, please delete "4-[(2, 5-dimethylpyrrolidin-" and insert -- 4-[(2,5-dimethylpyrrolidin -- therefore.

Column 102 in Claim 15, Line 60, please delete "(3 S)-3-" and insert -- (3S)-3- -- therefore.

Signed and Sealed this
Fifth Day of March, 2019

Andrei Iancu
*Director of the United States Patent and Trademark Office*